(12) United States Patent
Ghosh et al.

(10) Patent No.: US 7,335,632 B2
(45) Date of Patent: Feb. 26, 2008

(54) BETA-SECRETASE INHIBITORS AND METHODS OF USE THEREOF

(75) Inventors: Arun K. Ghosh, West LaFayette, IN (US); Hui Lei, Edmond, OK (US); Thippeswamy Devasamudram, Edmond, OK (US); Chunfeng Liu, Oklahoma City, OK (US); Jordan J. N. Tang, Edmond, OK (US); Geoffrey Bilcer, Edmond, OK (US)

(73) Assignee: CoMentis, Inc., South San Francisco, CA (US)

( * ) Notice: Subject to any disclaimer, the term of this patent is extended or adjusted under 35 U.S.C. 154(b) by 138 days.

(21) Appl. No.: 10/944,117

(22) Filed: Sep. 17, 2004

(65) Prior Publication Data

US 2005/0239684 A1   Oct. 27, 2005

Related U.S. Application Data

(63) Continuation-in-part of application No. 10/493,439, filed as application No. PCT/US02/34324 on Oct. 23, 2002.

(60) Provisional application No. 60/397,619, filed on Jul. 19, 2002, provisional application No. 60/397,557, filed on Jul. 19, 2002, provisional application No. 60/390,804, filed on Jun. 20, 2002, provisional application No. 60/348,615, filed on Jan. 14, 2002, provisional application No. 60/348,464, filed on Jan. 14, 2002, provisional application No. 60/333,545, filed on Nov. 27, 2001, provisional application No. 60/335,952, filed on Oct. 23, 2001.

(51) Int. Cl.
  *A61K 38/00*  (2006.01)
  *A61K 47/06*  (2006.01)
  *A61K 49/00*  (2006.01)

(52) U.S. Cl. ............................ 514/2; 514/18; 530/300; 424/9.2; 424/1.65; 424/9.1

(58) Field of Classification Search ............... None
See application file for complete search history.

(56) References Cited

U.S. PATENT DOCUMENTS

| | | | |
|---|---|---|---|
| 4,713,445 A | 12/1987 | Szelke et al. |
| 4,801,575 A | 1/1989 | Pardridge |
| 4,861,760 A | 8/1989 | Mazuel et al. |
| 4,911,920 A | 3/1990 | Jani et al. |
| 4,923,967 A | 5/1990 | Bobbitt et al. |
| 5,200,339 A | 4/1993 | Abraham |
| 5,212,162 A | 5/1993 | Missel et al. |
| 5,221,607 A | 6/1993 | Cordell et al. |
| 5,235,043 A | 8/1993 | Collins et al. |
| 5,252,463 A | 10/1993 | Nelson et al. |
| 5,403,841 A | 4/1995 | Lang et al. |
| 5,643,878 A | 7/1997 | Bold et al. |
| 5,733,768 A | 3/1998 | Dixon et al. |
| 5,744,346 A | 4/1998 | Chrysler et al. |
| 5,942,400 A | 8/1999 | Anderson et al. |
| 5,978,740 A | 11/1999 | Armistead et al. |
| 5,986,054 A | 11/1999 | St. George-Hyslop et al. |
| 6,077,682 A | 6/2000 | Inouye et al. |
| 6,207,710 B1 | 3/2001 | Audia et al. |
| 6,245,884 B1 | 6/2001 | Hook |
| 6,287,792 B1 | 9/2001 | Pardridge et al. |
| 6,291,223 B1 | 9/2001 | Christie et al. |
| 6,313,268 B1 | 11/2001 | Hook |
| 6,319,689 B1 | 11/2001 | Powell et al. |
| 6,329,163 B1 | 12/2001 | Anderson et al. |
| 6,361,975 B1 | 3/2002 | Christie et al. |
| 6,420,534 B1 | 7/2002 | Gurney et al. |
| 6,545,127 B1 | 4/2003 | Tang et al. |
| 2002/0037315 A1 | 3/2002 | Gurney et al. |
| 2002/0055459 A1 | 5/2002 | Chopra et al. |
| 2002/0072050 A1 | 6/2002 | Hook |
| 2002/0081634 A1 | 6/2002 | Gurney et al. |
| 2002/0115600 A1 | 8/2002 | Koelsch et al. |
| 2003/0092629 A1 | 5/2003 | Tang et al. |
| 2004/0121947 A1 | 6/2004 | Ghosh et al. |
| 2004/0167075 A1 | 8/2004 | Tang et al. |
| 2004/0220079 A1 | 11/2004 | Koelsch et al. |
| 2006/0234944 A1 | 10/2006 | Ghosh et al. |

FOREIGN PATENT DOCUMENTS

| | | |
|---|---|---|
| EP | 0 302 469 A2 | 8/1988 |
| EP | 0 302 469 A3 | 8/1988 |
| EP | 0 855 444 A2 | 7/1998 |

(Continued)

OTHER PUBLICATIONS

Cronin NB; Badasso MO, Tickle IJ, Dreyer T, Hoover DJ, Rosati RL, Humblet, CC, Lunney EA, Cooper JB, X-ray Structures of Five Renin Inhibitors Bound to Saccharopepsin: Exploration of Active-site Specificity, Journal of Molecular Biology, 2000, 303(5):745-760.*

(Continued)

*Primary Examiner*—Anish Gupta
*Assistant Examiner*—Julie Ha
(74) *Attorney, Agent, or Firm*—Morrison & Foerster LLP

(57) ABSTRACT

The present invention provides novel beta-secretase inhibitors and methods for their use, including methods of treating of Alzheimer's disease.

25 Claims, No Drawings

FOREIGN PATENT DOCUMENTS

| | | |
|---|---|---|
| EP | 0 855 444 A3 | 7/1998 |
| JP | 10 108 681 A | 4/1998 |
| WO | WO-96/05309 A2 | 2/1996 |
| WO | WO-96/05309 A3 | 2/1996 |
| WO | WO-96/40885 A2 | 12/1996 |
| WO | WO-96/40885 A3 | 12/1996 |
| WO | WO-97/27296 A1 | 7/1997 |
| WO | WO-98/13488 A2 | 4/1998 |
| WO | WO-98/13488 A3 | 4/1998 |
| WO | WO-98/15828 A1 | 4/1998 |
| WO | WO-98/21589 A1 | 5/1998 |
| WO | WO-98/26059 A1 | 6/1998 |
| WO | WO-99/51752 A1 | 10/1999 |
| WO | WO-99/64587 A1 | 12/1999 |
| WO | WO-00/17369 A2 | 3/2000 |
| WO | WO-00/17369 A3 | 3/2000 |
| WO | WO-00/23576 A2 | 4/2000 |
| WO | WO-00/23576 A3 | 4/2000 |
| WO | WO-00/47618 A2 | 8/2000 |
| WO | WO-00/47618 A3 | 8/2000 |
| WO | WO-00/58479 A1 | 10/2000 |
| WO | WO-00/77030 A1 | 12/2000 |
| WO | WO-01/00663 A2 | 1/2001 |
| WO | WO-01/00663 A3 | 1/2001 |
| WO | WO-01/00665 A2 | 1/2001 |
| WO | WO-01/00665 A3 | 1/2001 |
| WO | WO-01/23533 A2 | 4/2001 |
| WO | WO-01/23533 A3 | 4/2001 |
| WO | WO-01/70672 A2 | 9/2001 |
| WO | WO-01/70672 A3 | 9/2001 |
| WO | WO-02/25276 A1 | 3/2002 |
| WO | WO-02/053594 A2 | 7/2002 |
| WO | WO-02/053594 A3 | 7/2002 |
| WO | WO-03/039454 A2 | 5/2003 |
| WO | WO-03/039454 A3 | 5/2003 |

OTHER PUBLICATIONS

Hom, Roy K., et al. "Design and Synthesis of Hydroxyethylene-Based Peptidomimetic Inhibitors of Human β-Secretase", *J. Med. Chem.* (2004) 47:158-164.

Tung, Jay S., et al. "Design of Substrate-Based Inhibitors of Human β-Secretase", *J. Med. Chem.* (2002) 45:259-262.

Ghosh, Arun K., et al. "Design of Potent Inhibitors for Human Brain Memapsin 2 (β-Secretase)", *J. Am. chem., Soc.* (2002) 122:3522-3523.

Hong, Lin, et al. "Structure of the Protease Domain of Memapsin 2 (β-Secretase) Complexed with Inhibitor" *Science*, (2000) 290:150-153.

Shearman, Mark S., et al., "L-685, 458, an Aspartyl Protease Transition State Mimic, Is a Potent Inhibitor of Amyloid β-Protein Precursor γ-Secretase Activity", Biochemistry (2000) 39:8698-8704.

Abad-Zapatero, C. et al. (1996). "Structure of a Secreted Aspartic Protease From *C. Albicans* Complexed with a Potent Inhibitor: Implications for the Design of Antifungal Agents," *Protein Science* 5:640-652.

Abbenate, G. et al. (Feb. 5, 2000). "Inhibitors of β-Amyloid Formation Based on the β-Secretase Cleavage Site," *Biochemical and Biophysical Research Communications* 268(1):133-135.

Askew, B. et al. (Jan. 4, 1989). "Molecular Recognition with Convergent Functional Groups. 6. Synthetic and Structural Studies with a Model Receptor for Nucleic Acid Components," *Journal of the American Chemical Society* 111:1082-1090.

Australian Office Action mailed on Jan. 14, 2005, for AU Application No. 2002239727 filed Dec. 28, 2001, 2 pages.

Australian Office Action mailed on Jun. 5, 2007 for AU Application No. 2002359301 filed Oct. 23, 2002, 2 pages.

Azami, H. et al. (1997). "Studies on β-Lactum Antibiotics. Synthesis and Antibacterial Activity of Novel 1 β-Methylcarbapenems Related to FR21818: 5-Membered Ring Analogs," *Bioorganic & Medicinal Chemistry Letters* 7(11):1409-1414.

Bailey, D. et al. (1994). "A Structural Comparison of 21 Inhibitor Complexes of the Aspartic Proteinase From *Endothia parasitica*," *Protein Science* 3:2129-2143.

Bergman, E.D. et al. (1963). "Organic Fluorine Compounds. Part XXVII. Fluorinated α-Aminoisobutyric Acids," *Journal of the Chemical Society* Part III, pp. 3462-3463.

Berkowitz, D.B. et al. (2000). "Enzyme-Assisted Asymmetric Total Synthesis of (-)-, Podophyllotoxin and (-)-Picropodophyllin," *Journal of Organic Chemistry* 65(3):847-860.

Bieth, J. (1974). "Some Kinetic Consequences of the Tight Binding of Protein-Proteinase-Inhibitors to Proteolytic Enzymes and Their Application to the Determination of Dissociation Constants" In *Bayer-Symposium Proteinase Inhibitors Proceedings of the 2nd International Research Conference.* H. Fritz et al. eds. Springer-Verlag: Berlin, Germany, pp. 463-469.

Bradbury, R.H. et al. (Sep. 1990). "1,2,4-Triazolo [4,3-*a*]pyrazine Derivatives with Human Renin Inhibitory Activity. 2. Synthesis, Biological Properties and Molecular Modeling of Hydroxyethylene Isostere Derivatives," *Journal of Medicinal Chemistry* 33(9):2335-2342.

Brightman, M.W. et al. (1995). "Penetration of Solutes, Viruses, and Cells Across the Blood-Brain Barrier" In *HIV and Dementia: Proceedings of the NIMH-Sponsored Conference Pathogenesis of HIV Infection of the Brain: Impact on Function and Behavior.* Oldstone, M.B.A. et al. eds. Springer-Verlag: Berlin, pp. 63-78.

Brünger, A.T. et al. (1998). "Crystallography & NMR System: A New Software Suite for Macromolecular Structure Determination," *Acta Crystallographica Section D Biological Crystallography* D54:905-921.

Capell, A. et al. (Feb. 6, 1998). "The Proteolytic Fragement of the Alzheimer's Disease-Associated Presenilin-1 Form Heterodimers and Occur as a 100-150-kDA Molecular Mass Complex," *The Journal of Biological Chemistry* 273(6):3205-3211.

Chartier-Harlin, M.C. et al. (Oct. 31, 1991). "Early-Onset Alzheimer's Disease Caused by Mutations at Codon 717 of the β-Amyloid Precursor Protein Gene," *Nature* 353(6347):844-846.

Chen, P. et al. (Sep. 24, 1998). "Strategies to Target Kyotorphin Analogues to the Brain," *Journal of Medicinal Chemistry* 41(20):3773-3781.

Ciapetti, P. et al. (1998). "Nucleophilic Substitution of Protected 2-Amino-4-Butanoic Acid. An Easy Route to Exotic Amino Acids and Conformationally Constrained Peptides," *Tetrahedron Letters* 39:3843-3846.

Citron, M. et al. (Dec. 17, 1992). "Mutation of the β-Amyloid Precursor Protein in Familial Alzheimer's Disease Increases β-Protein Production," *Nature* 360(6405):672-674.

Cohen, B.A. et al. (Nov. 1998). "An Artificial Cell-Cycle Inhibitor Isolated From a Combinatorial Library," *Proc. Natl. Acad. Sci. USA* 95:14272-14277.

Corder, E.H. et al. (Aug. 13, 1993). "Gene Dose of Apolipoprotein E Type 4 Allele and the Risk of Alzheimer's Disease in Late Onset Families," *Science* 261:921-923.

Cowley, G. (Jan. 31, 2000). "Alzheimer's Unlocking the Mystery," *Newsweek* pp. 46-51.

Crane, E.J. ed. (Jul. 20-Nov. 20, 1946). 40:1946 (Column 4066).

Cutfield, S.M. et al. (Nov. 15, 1995). "The Crystal Structure of a Major Secreted Aspartic Proteinase From *Candida albicans* in Complexes with Two Inhibitors," *Structure* 3(11):1261-1271.

Davies, D.R. (1990). "The Structure and Function of the Aspartic Proteinases," *Annual Review of Biophysics and Biophysical Chemistry* 19:189-215.

De Strooper, B. et al. (Jan. 22, 1998). "Deficiency of Presenilin-1 Inhibits the Normal Cleavage of Amyloid Precursor Protein," *Nature* 391:387-390.

De Vleeschauwer, M. et al. (Apr. 1997). "Remarkably Mild and Simple Preparations of Sulfinates, Sulfonyl Chlorides and Sulfonamides From Thioanisoles," *Synlett*, pp. 375-377.

Dealwis, C.G. et al. (Feb. 11, 1994). "X-Ray Analysis at 2.0 Å Resolution of Mouse Submaxillary Renin Complexed with a Decapeptide Inhibitor CH-66, Based on the 4-16 Fragment of Rat Angiotensinogen," *Journal of Molecular Biology* 236(1):342-360.

Egleton, R.D. et al. (1997). "Bioavailability and Transport of Peptides and Peptide Drugs into the Brain," *Peptides* 18(9):1431-1439.

Ellington, A.D. et al. (Aug. 30, 1990). "In Vitro Selection of RNA Molecules That Bind Specific Ligands," *Nature* 346(6287):818-822.

Ermolieff, J. et al. (Oct. 10, 2000). "Proteolytic Activation of Recombinant Pro-memapsin 2 (Pro-β-secretase) Studied with New Fluorogenic Substrates," *Biochemistry* 39(40):12450-12456.

Ezzell, C. (Mar. 7, 1992). "Alzheimer's Alchemy," *Science News* 141(10):152-153.

Farzan, M. et al. (Aug. 15, 2000). "BACE2, a β-secretase Homolog, Cleaves at the β Site and Within the Amyloid-β Region of the Amyloid-Beta Precursor Protein," *Proc. Natl. Acad. Sci. USA* 97(17):9712-9717.

Fersht, A. (1985). *Enzyme Structure and Mechanism. 2nd edition.* W.H. Freeman and Company: New York, pp. xi-xxi. (Table of Contents).

Fields, S. et al. (Jul. 20, 1989). "A Novel Genetic System to Detect Protein-Protein Interactions," *Nature* 340(6230):245-246.

Fray, A.H. et al. (1986). "A Short, Stereoselective Synthesis of the lactone Precursor to 2R, 4S, 5SHydroxyethylene Dipeptide Isosteres," *The Journal of Organic Chemistry* 51(25):4828-4833.

Ghersi-Egea, J.-F. et al. (Aug. 1996). "Fate of Cerebrospinal Fluid-Borne Amyloid Beta-peptide: Rapid Clearance into Blood and Appreciable Accumulation by Cerebral Arteries," *Journal of Neurochemistry* 67(2):880-883.

Ghosh, A.K. et al. (1992). "N,N'-Disuccinimidyl Carbonate; A Useful Reagent for Alkoxycarbonylation of Amines," *Tetrahedron Letters* 33(20):2781-2784.

Ghosh, A.K. et al. (1993). "Potent HIV Protease Inhibitors: The Development of Tetrahydrofuranylglycines as Novel $P_2$-Ligands and Pyrazine Amides as $P_3$-Ligands," *Journal of Medicinal Chemistry* 36(16):2300-2310.

Ghosh, A.K. et al. (1998). "Transition-State Mimetics for HIV Protease Inhibitors: Stereocontrolled Synthesis of Hydroxyethylene and Hydroxyethylamine Isosteres by Ester-Derived Titanium Enolate Syn and Anti-Aldol Reactions," *The Journal of Organic Chemistry* 63(18):6146-6152.

Ghosh, A.K. et al. (2001). "Structure-Based Design: Potent Inhibitors of Human Brain Memapsin 2 (β-Secretase)," *J. Med. Chem.* 44(18):2865-2868.

Glenner, G.G. et al. (May 16, 1984). "Alzheimer's Disease: Initial Report of the Purification and Characterization of a Novel Cerebrovascular Amyloid Protein," *Biochemical and Biophysical Research Communications* 120(3):885-890.

Goate, A. et al. (Feb. 21, 1991). "Segregation of a Missense Mutation in the Amyloid Precursor Protein Gene with Familial Alzheimer's Disease," *Nature* 349(6311):704-706.

Goldgaber, D. et al. (Feb. 20, 1987). "Characterization and Chromosomal Localization of a cDNA Encoding Brain Amyloid of Alzheimer's Disease," *Science* 235(4791):877-880.

Grandberg, I.I. (Feb. 1963), "Ultraviolet Spectra of Pyrazole Systems," *Journal of General Chemistry of the USSR* 33(2):511-516.

Grindley, R. et al. (Oct. 1927). "The Condensation of Glyoxalines with Formaldehyde," *Journal of the Chemical Society*, pp. 3128-3136.

Haass, C. et al. (Oct. 29, 1999). "The Presenilins in Alzheimer's Disease-Proteolysis Holds the Key," *Science* 286:916-919.

Hong, L. et al. (2002). "Crystal Structure of Memapsin 2 (β-secretase) in Complex with an Inhibitor OM00-3," *Biochemistry* 41:10963-10967.

Howarth, N.M. et al. (1997). "α-PNA: A Novel Peptide Nucleic Acid Analogue of DNA," *Journal of Organic Chemistry* 62(16):5441-5450.

Hsiao, K. et al. (Oct. 4, 1996). "Correlative Memory Deficits, Aβ Elevation, and Amyloid Plaques in Transgenic Mice," *Science* 274:99-102.

Hussain, I. et al. (Jun. 29, 2001). "Prodomain Processing of Asp1 (BACE2) is Autocatalytic," *The Journal of Biological Chemistry* 276(26):23322-23328.

International Preliminary Examination Report mailed on Jul. 15, 2004, for PCT Application No. PCT/US01/50826 filed Dec. 28, 2001, five pages.

International Search Report mailed on Jul. 24, 2003, for PCT Application No. PCT/US02/34324 filed Oct. 23, 2002, nine pages.

International Search Report mailed on Mar. 28, 2003, for PCT Application No. PCT/US01/50826 filed Dec. 28, 2001, seven pages.

Jones, T.A. et al. (Mar. 1, 1991). "Improved Methods for Binding Protein Models in Electron Density Maps and the Location of Errors in These Models," *Acta Crystallographica* A47(Part 2):110-119.

Kaga, H. et al. (1996). "A General and Stereoselective Synthesis of the Capsaicinoids via the Orthoester Claisen Rearrangement," *Tetrahedron* 52(25):8451-8470.

Kang, J. et al. (Feb. 19, 1987). "The Precursor of Alzheimer's Disease Amyloid A4 Protein Resembles a Cell-Surface Receptor," *Nature* 325(6106):733-736.

Kassel, D.B. et al. (Jul. 1, 1995). "HIV-1 protease Specificity Derived From a Complex Mixture of Synthetic Substrates," *Analytical Biochemistry* 228(2):259-266.

Kawarabayashi, T. et al. (Jan. 15, 2001). "Age-Dependent Changes in Brain, CSF, and Plasma Amyloid Beta Protein in the Tg2576 Transgenic Mouse Model of Alzheimer's Disease," *The Journal of Neuroscience* 21(2):372-381.

Kearney, B.P. et al. (Nov. 1999). "The Penetration of Anti-Infectives Into the Central Nervous System," *Neurologic Clinics* 17(4):883-900.

Kelly, D.J. et al. (Dec. 1984). "Microbial Differentiation: The Role of Cellular Asymmetry," *Microbiological Sciences* 1(9):214-219.

Khan, A.R. et al. (Dec. 1, 1998). "Lowering the Entropic Barrier for Binding Conformationally Flexible Inhibitors to Enzymes," *Biochemistry* 37(48):16839-16845.

Kirst, H.A. et al. (1981). "Control of Site-Specific Substitution of Aminoglycosides by Transition Metal Cations," *Tetrahedron Letters* 22(4):295-298.

Knops, J. et al. (Feb. 10, 1995). "Cell-Type and Amyloid Precursor Protein-Type Specific Inhibition of Aβ Release by Bafilmoycin A1, a Selective Inhibitor of Vacuolar ATPases," *The Journal of Biological Chemistry* 270(6):2419-2422.

Koelsch, G. et al. (2000). "Enzymic Characteristics of Secreted Aspartic Proteases of *Candida albicans*," *Biochemica et Biophysica Acta* 1480:117-131.

Koga, H. et al. (Jul. 1976). "Novel Rearrangement of Pyrazole N-Imines with Acetic Anhydride," *Chemical & Pharmaceutical Bulletin* 24(9):2267-2269.

Kolata, G. (Oct. 22, 1999). "Scientists Find Enzyme Linked to Alzheimer's," located at <http://www.query.nytimes.com/gst/fullpage.html?res=9C05E2D81139F931A15753C...>, last visited on Jul. 17, 2007, 2 pages.

Kreuter, J. (Mar. 23, 2001). "Nanoparticulate Systems for Brain Delivery of Drugs," *Advanced Drug Delivery Review* 47(1):65-81.

Ksander, G.M. et al. (Feb. 1997). "Ortho-Substituted Benzofused Macrocyclic Lactams as Zinc Metalloprotease Inhibitors," *Journal of Medicinal Chemistry* 40(4):495-505.

Lam, K.S. et al. (Nov. 7, 1991). "A New Type of Synthetic Peptide Library for Identifying Ligand-Binding Activity," *Nature* 354(6348):82-84.

Laskowski, R.A. et al. (1993). "Procheck: A Program to Check the Stereochemical Quality of Protein Structures," *Journal of Applied Crystallography* 26:283-291.

Lemaire, H.G. et al. (1989). "The $PreA4_{695}$ Precursor Protein of Alzheimer's Disease A4 Amyloid is Encoded by 16 Exons," *Nucleic Acids Research* 17(2):517-522.

Levy, E. et al. (Jun. 1, 1990). "Mutation of the Alzheimer's Disease Amyloid Gene in Hereditary Cerebral Hemorrhage, Dutch Type," *Science* 248(4959):1124-1126.

Levy-Lahad, E. et al. (Aug. 18, 1995). "Candidate Gene for the Chromosome 1 Familial Alzheimer's Disease Locus," *Science* 269:973-977.

Lewis, R.A. et al. (Mar. 22, 1989). "Automated Site-Directed Drug Design: The Formation Molecular Template in primary Structure Generation," *Proceedings of the Royal Society of London. B. Biological Sciences* 236(1283):141-162.

Lin, X. et al. (Aug. 1993). "Intracellular Diversion of Glycoprotein GP160 of Human Immunodeficiency Virus to Lysosomes as a Strategy of AIDS Gene Therapy," *FASEB J.* 7:1070-1080.

Lin, X. et al. (1994). "Relationships of Human Immunodeficiency Virus Protease with Eukaryotic Aspartic Proteases," *Methods in Enzymology* 241:195-224.

Lin, X. et al. (Feb. 15, 2000). "Human Aspartic Protease Memapsin 2 Cleaves the β-Secretase Site of β-Amyloid Precursor Protein," *Proc. Natl. Acad. Sci. USA* 97(4):1456-1460.

Liu, K. et al. (2002). "Glu11 Site Cleavage and N-Terminally Truncated AβProduction Upon BACE Overexpression," *Biochemistry* 41(9):3128-3136.

Majer, P. et al. (1997). "Structure-Based Subsite Specificity Mapping of Human Cathepsin D Using Statine-Based Inhibitors," *Protein Science* 6:1458-1466.

Mann, D.M.A. (Sep./Oct. 1989). "Cerebral Amyloidosis, Ageing and Alzheimer's Disease; A Contribution From Studies on Down's Syndrome," *Neurobiology of Aging* 10(5):397-399.

Marciniszyn, Jr., J. et al. (Nov. 25, 1976). "Mode of Inhibition of Acid Proteases by Pepstatin," *The Journal of Biological Chemistry* 251(22):7088-7094.

Martin, C. et al. (1999). "Indinavir-based Treatment of HIV-1 Infected Patients: Efficacy in the Central Nervous System," *AIDS* 13(10):1227-1232.

Martson, F.A.O. et al. (1990). "Solubilization of Protein Aggregrates," *Methods in Enzymology* 182:264-267.

Matsumoto, A. et al. (May 1995). "Molecular Cloning of Human cDNA with a Sequence Highly Similar to That of the Dihydrofolate Reductase Gene in Brain Libraries Derived From Alzheimer's Disease Patients," *European Journal of Biochemistry* 230(1):337-343.

McKinlay, M.A. et al. (1989). "Rational Design of Antiviral Agents," *Annual Review of Pharmacology Toxicology* 29:111-122.

Meckelein, B. et al. (1998). "Identification of a Novel Serine Protease-Like Molecular in Human Brain," *Molecular Brain Research* 55(2):181-197.

Mullan, M. et al. (Aug. 1992). "A Pathogenic Mutation for Probable Alzheimer's Disease in the APP Gene at the N-Terminus of βAmyloid," *Nature Genetics* 1(5):345-347.

Mullan, M. et al. (Dec. 1992). "A Locus for Familial Early-Onset Alzheimer's Disease on the Long Arm of Chromosome 14, Proximal to the α1-Antichmotryspin Gene," *Nature Genetics* 2(4):340-342.

Murrell, J. et al. (Oct. 4, 1991). "A Mutation in the Amyloid Precursor Protein Associated with Hereditary Alzheimer's Disease," *Science* 254(5028):97-99.

Navaza, J. (Mar. 1, 1994). "AMoRe: An Automated Package for Molecular Replacement," *Acta Crystallographica Section A Fundamentals of Crystallography* A50(Part 2):157-163.

Noland, W.E. et al. (Jun. 20, 1954). "The Nitroethylation of Indole. A New Synthesis of Tryptamine," *The Journal of the American Chemical Society* 124:3227-3228.

Oefner, C. et al. (Mar. 1999). "Renin Inhibition by Substituted Piperdines: A Novel Paradigm for the Inhibition of Monomeric Apsartic Proteinases?" *Chemistry & Biology* 6(3):127-131.

Otwinowski, Z. et al. (1997). "Processing of X-Ray Diffraction Data Collected in Oscillation Mode," *Methods in Enzymology* 276:307-326.

Overman, L.E. et al. (Aug. 9, 1985). "A Convenient Method for Obtaining trans-2-Aminocyclohexanol and trans-2-Aminocyclopentanol in Enantiomerically Pure Form," *The Journal of Organic Chemistry* 50(16-21):4154-4155.

Pardridge, W.M. (1999). "Vector-mediated Drug Delivery to the Brain," *Advanced Drug Delivery Reviews* 36(2-3):299-321.

Paris, N. et al. (Aug. 1990). "Bacterial Production and Purfication of Recombinant Human Prolactin," *Biotechnology & Applied Biochemistry* 12(4):436-449.

Pegorier, L. et al. (1995). "A General Stereocontrolled Synthesis of Hydroxyethylene Dipeptide Isoteres," *Tetrahedron Letters* 36(16):2753-2756.

Perez, R.G. et al. (Apr. 12, 1996). "Enhanced Release of Amyloid β-Protein From Codon 670/671 'Swedish' Mutant β-Amyloid Precursor Protein Occurs in Both Secretory and Endocytic Pathways," *The Journal of Biological Chemistry* 271(15):9100-9107.

Perry, N.C. et al. (1989). "The Use of 3D Modelling Databases for Identifying Structure Activity Relationships" In *QSAR: Quantitative Structure-Activity Relationships in Drug Design*. J.L. Fauchère ed., Alan R. Liss, Inc.: NY, pp. 189-193.

Phimister, B. (Jan. 2000). "Four Companies Announce Discovery of β-Secretase Gene," *Nature Biotechnology* 18:16.

Podlisny, M.B. et al. (1997). "Presenilin Proteins Undergo Heterogeneous Endoproteolysis Between $Thr_{291}$ and $Ala_{299}$ and Occur as Stable N- and C-Terminal Fragments in Normal and Alzheimer Brain Tissue," *Neurobiology of Disease* 3(4):325-337.

Reetz, M.T. et al. (Nov. 1987). "Stereoselective Synthesis of β-Amino Alcohols From Optically Active α-Amino Acids," *Agnew. Chem. Int. Ed. Engl.* 26(11):1141-1143.

Ripka, W. (Jun. 16, 1988). "Computers Picture the Perfect Drug," *New Scientist* 118(1617):54-58.

Robakis, N.K. et al. (Jun. 1987). "Molecular Cloning and Characterization of a cDNA Encoding the Cerebrovascular and the Neuritic Plaque Amyloid Peptides," *Proc. Natl. Acad. Sci. USA* 84 4190-4194.

Roberts, R.W. et al. (Nov. 1997). "RNA-Peptide Fusions for the in Vitro Selection of Peptides and Proteins," *Proc. Natl. Acad. Sci. USA* 94:12297-12302.

Rogaev, E.I. et al. (Aug. 31, 1995). "Familial Alzheimer's Disease in Kindreds with Missense Mutations in a Gene on Chromosome 1 Related to the Alzheimer's Disease Type 3 Gene," *Nature* 376:775-778.

Rouvinen, J. et al. (1988). "Computer-Aided Drug Design," *Acta Pharmaceutica Fennica* 97:159-166.

Rumble, B. et al. (Jun. 1, 1989). "Amyloid A4 Protein and its Precursor in Down's Syndrome and Alzheimer's Disease," *The New England Journal of Medicine* 320(22):1446-1452.

Saunders, A.J. et al. (Nov. 12, 1999). "*BACE* Maps to Chromosome 11 and a *BACE* Homolog, *BACE2*, Reside in the Obligate Down Syndrome Region of Chromosome 21," *Science* 286:1255a-1255a (two pages).

Schechter, I. et al. (1967). "On the Size of the Active Site in Proteases I. Papain," *Biochemical and Biophysical Research Communications* 27(2):157-162.

Schwarze, S.R. et al. (Sep. 3, 1999). "In Vivo Protein Transduction: Delivery of a Biologically Active Protein into the Mouse," *Science* 285:1569-1572.

Selkoe, D.J. (Jun. 24, 1999). "Translating Cell Biology into Therapeutic Advances in Alzheimer's Disease," *Nature* 399(Suppl):A23-A31.

Selkoe, D.J. (Apr. 2001). "Alzheimer's Disease: Genes, Proteins, and Therapy," *Physiological Reviews* 81(2):741-766.

Sherrington, R. et al. (Jun. 29, 1995). "Cloning of a Gene Bearing Missense Mutation in Early-Onset Familial Alzheimer's Disease," *Nature* 375:754-760.

Sinha, S. et al. (Sep. 1999). "Cellular Mechanisms of β-Amyloid Production and Secretion," *Proc. Natl. Acad. Sci. USA* 96:11049-11053.

Sinha, S. et al. (Dec. 2, 1999). "Purification and Cloning of Amyloid Precursor Protein β-Secretase From Human Brain," *Nature* 402:537-540.

Soliman, R. et al. (Nov. 1983). "Antidiabetic Activity of Some 1-Substituted 3,5-Dimethylpyrazoles," *Journal of Medicinal Chemistry* 26(11):1659-1663.

Stachel, S.J. et al. (2004). "Structure-Based Design of Potent and Selective Cell-Permeable Inhibitors of Human β-Sectrease (BACE-1)," *Journal of Medicinal Chemistry* 47(26):6447-6450.

Steiner, H. et al. (Nov. 27, 1998). "Expression of Alzheimer's Disease-Associated Presenilin-1 is Controlled by Proteolytic Degradation and Complex Formation," *The Journal of Biological Chemistry* 273(48):32322-32331.

Stoner, E.J. et al. (2000). "Synthesis of HIV Protease Inhibitor ABT-378 (Lopinavir)," *Organic Process Research & Development* 4:264-269.

Suzuki, N. et al. (May 27, 1994). "An Increased Percentage of Long Amyloid β Protein Secreted by Familial Amyloid β Protein Precursor ($βAPP_{717}$) Mutants," *Science* 264:1336-1340.

Symersky, J. et al. (Oct. 21, 1997). "High-Resolution Structure of the Extracellular Aspartic Proteinase From *Candida tropicalis* Yeast," *Biochemistry* 36(42):12700-12710.

Szostak, J.W. (Mar. 1992). "In Vitro Genetics," *Trends in Biochemical Sciences* 17(3):89-93.

Tagawa, K. et al. (May 31, 1991). "Alzheimer's Disease Amyloid β-Clipping Enzyme (APP Secretase): Identification, Purification, and Characterization of the Enzyme," *Biochemical and Biophysical Research Communications* 177(1):377-387.

Tang, J. et al. (Feb. 16, 1978). "Structural Evidence for Gene Duplication in the Evolution of the Acid Proteases," *Nature* 271(5646):618-621.

Tanzi, R.E. et al. (Feb. 1, 1988). "Protease Inhibitor Domain Encoded by an Amyloid Protein Precursor mRNA Associated with Alzheimer's Disease," *Nature* 331(6156):528-530.

Thinakaran, G. et al. (Jul. 1996). "Endoproteolysis of Presenilin 1 and Accumulation of Processed Derivatives In Vivo," *Neuron* 17(1):181-190.

Thinakaran, G. et al. (Nov. 7, 1997). "Evidence That Levels of Presenilins (PS1 and PS2) Are Coordinately Regulated by Competition for Limiting Cellular Factors," *The Journal of Biological Chemistry* 272(45):28415-28422.

Thinakaran, G. et al. (1998). "Stable Association of Presenilin Derivatives and Absence of Presenilin Interactions with APP," *Neurobiology of Disease* 4(6):438-453.

Turner, R.T. et al. (Mar. 7, 2001). "Substrate Specify of Memapsin 2 (β-Secretase): Basis for Inhibitor Drug Design for Alzheimer's Disease," *The FASEB Journal Abstracts* 15(4):A538 (Abstract No. 443.12).

U.S. Appl. No. 09/603,713, filed Jun. 27, 2000, by Tang et al.

U.S. Appl. No. 09/795,903, filed Feb. 28, 2001, by Lin et al.

U.S. Appl. No. 09/796,264, filed Feb. 28, 2001, by Tang.

U.S. Appl. No. 10/383,161, filed Mar. 5, 2003, by Tang et al.

Van Broeckhoven, C. et al. (Jun. 1, 1990). "Amyloid β Protein Precursor Gene and Hereditary Cerebral Hemorrhage with Amyloidosis (Dutch)," *Science* 248(4959):1120-1122.

van de Waterbeemd, H. et al. (1998). "Estimation of Blood-Brain Barrier Crossing of Drugs Using Molecular Size and Shape, and H-Bonding Descriptors," *Journal of Drug Targeting* 6(2):151-165.

Varon, S. et al. (1983/1984). "Neuronotrophic and Neurite-Promoting Factors and Their Clinical Potentials," *Developmental Neuroscience* 6:73-100.

Vassar, R. et al. (Oct. 22, 1999). "β-Secretase Cleavage of Alzheimer's Amyloid Precursor Protein by the Transmembrane Asparatic Protease BACE," *Science* 286:735-741.

Walsh, D.M. et al. (Sep. 3, 1999). "Amyloid β-Protein Fibrillogenesis," *The Journal of Biological Chemistry* 274(36):25945-25952.

Wender, P.A. et al. (Nov. 21, 2000). "The Design, Synthesis, and Evaluation of Molecules That Enable or Enhance Cellular Uptake: Peptoid Molecular Transporters," *Proc. Natl. Acad. Sci. USA* 97(24):13003-13008.

Williams, R.M. et al. (Mar. 1988). "Practical Asymmetric Synthesis of α-Amino Acids Through Carbon-Carbon Bond Constructions on Electrophillic Glycine Templates," *Journal of the American Chemical Society* 110(5):1547-1557.

Wolfe, M.S. et al. (Apr. 8, 1999). "Two Transmembrane Asparates in Presenilin-1 Required for Presenlin Endoproteolysis and y-Secretase Activity," *Nature* 398:513-517.

Yamamoto, K. et al. (1991). "Biological Significance and Activity Control of Cathepsin E Compared with Cathepsin D" *In Structure and Function of the Aspartic Proteinases*. B.M. Dunn ed., Plenum Press: New York, NY, pp. 297-306.

Yang, J. et al. (Mar. 1999). "Structure of the *Rhizomucor miehei* Aspartic Proteinase Complexed with the Inhibitor Pepstatin A at 2.7 Å Resolution," *Acta Crystallographica Section D Biological Crystallography* 55(Part 3):625-630.

Yin, J. et al. (1998). "Synthesis and Immobilization of Ceramide Analogs on Silica Particles," *Bioorgranic & Medicinal Chemistry Letters* 8:179-182.

Yoshikai, S. et al. (1990). "Genomic Organization of the Human-Amyloid Beta-Protein Precursor Gene," *Gene* 87(2):257-263.

Yu, G.S.P. et al. (Oct. 2, 1998). "Inhibition of β-Amyloid Cytotoxicity by Midkine," *Neuroscience Letters* 254(3):125-128.

Zhao, M. et al. (1998). "A Novel Chromium Trioxide Catalyzed Oxidation of Primary Alcohols to the Carboxylic Acids," *Tetrahedron Letters* 39:5323-5326.

Zlokovic, B. (1997). "Can Blood-Brain Barrier Play a Role in the Development of Cerebral Amyloidosis and Alzheimer's Disease Pathology," *Neurobiology & Diseases* 4(1):23-26.

\* cited by examiner

BETA-SECRETASE INHIBITORS AND METHODS OF USE THEREOF

CROSS-REFERENCES TO RELATED APPLICATIONS

This application is a continuation-in-part of U.S. application Ser. No. 10/493,439, which claims the benefit of International Application No. PCT/US02/34324, filed Oct. 23, 2002, which claims the benefit of U.S. Provisional Application Nos. 60/335,952, filed Oct. 23, 2001; 60/333,545, filed Nov. 27, 2001; 60/348,464, filed Jan. 14, 2002; 60/348,615, filed Jan. 14, 2002; 60/390,804, filed Jun. 20, 2002; 60/397,557, filed Jul. 19, 2002; and 60/397,619, filed Jul. 19, 2002, all of which are herein incorporated by reference in their entirety for all purposes.

STATEMENT AS TO RIGHTS TO INVENTIONS MADE UNDER FEDERALLY SPONSORED RESEARCH OR DEVELOPMENT

The invention was supported, in whole or in part, by a National Institutes of Health grants AG-18933 and AI-38189. The Government has certain rights in the invention.

BACKGROUND OF THE INVENTION

Alzheimer's disease is a progressive mental deterioration in a human resulting, inter alia, in loss of memory, confusion and disorientation. Alzheimer's disease accounts for the majority of senile dementias and is a leading cause of death in adults (Anderson, R. N., *Natl. Vital Stat. Rep.* 49:1-87 (2001), the teachings of which are incorporated herein in their entirety). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease (Selkoe, D. J., *Nature* 399: 23-31 (1999)) and is a proteolytic fragment of amyloid precursor protein (APP). APP is cleaved initially by β-secretase followed by γ-secretase to generate Aβ (Lin, X., et al., *Proc. Natl. Acad. Sci. USA* 97:1456-1460 (2000); De Stropper, B., et al., *Nature* 391:387-390 (1998)).

There is a need to develop effective compounds and methods for the treatment of Alzheimer's disease. The present invention fulfills these and other needs.

BRIEF SUMMARY OF THE INVENTION

The present invention provides novel beta-secretase inhibitors and methods for their use, including methods of treating of Alzheimer's disease.

In one aspect, the present invention provides a β-secretase inhibitor compound represented by the following structural formula:

In the formula above, Y is a carrier moiety. Z is selected from a bond, $-OP(O)_2O-$, $-C(O)OR_{33}-$, $-C(O)NHR_{33}-$, $-S(O)_2NHR_{33}-$, substituted or unsubstituted aliphatic, or substituted or unsubstituted heteroalkylene. $R_{33}$ is a bond or an alkylene. The symbol "k" is selected from 0 to 5.

$A_1$ is a moiety represented by the following structural formula:

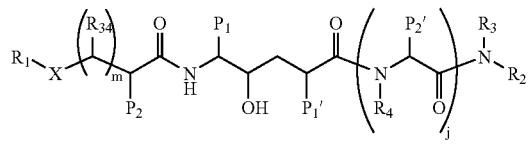

or optical isomers, diastereomers, or pharmaceutically acceptable salts of $A_1$.

X is $-C(O)-$, $-S(O)_n-$, or $-NH-C(O)-$. The symbol "n" represents 1 or 2, "m" is 0, 1, 2, 3, 4, or 5, and "j" is 0 or 1.

$P_1$ is selected from a substituted or unsubstituted aliphatic, substituted or unsubstituted hydroxyalkyl, substituted or unsubstituted aryl, substituted or unsubstituted aralkyl, substituted or unsubstituted heteroaryl, substituted or unsubstituted heteroaralkyl, substituted or unsubstituted heterocycloalkyl, or substituted or unsubstituted alkylsulfanylalkyl.

$P_1'$, and $P_2'$ are each, independently, a substituted or unsubstituted aliphatic, substituted or unsubstituted heteroalkyl, substituted or unsubstituted aryl, substituted or unsubstituted aralkyl, substituted or unsubstituted heteroaryl, substituted or unsubstituted heteroaralkyl, substituted or unsubstituted heterocycle, or substituted or unsubstituted heterocycloalkyl.

$R_1$ is selected from a substituted or unsubstituted aliphatic, substituted or unsubstituted alkoxy, substituted or unsubstituted aryl, substituted or unsubstituted aralkyl, substituted or unsubstituted heterocycle, substituted or unsubstituted heterocycloalkyl, substituted or unsubstituted heterocyclooxy, substituted or unsubstituted heterocycloalkoxy, substituted or unsubstituted heteroaryl, substituted or unsubstituted heteroaralkyl, substituted or unsubstituted heteroaralkoxy, or $-NR_5R_6$; or $R_1$, together with X, is a peptide or Y-Z-.

$R_4$ is hydrogen or a substituted or unsubstituted aliphatic.

$R_2$ and $R_3$ are each, independently, hydrogen, a substituted or unsubstituted aliphatic, substituted or unsubstituted aryl, substituted or unsubstituted aralkyl, substituted or unsubstituted heterocycle, substituted or unsubstituted heterocycloalkyl, substituted or unsubstituted heteroaryl, and substituted or unsubstituted heteroaralkyl; or one of $R_2$ and $R_3$, together with the nitrogen to which it is attached, is a peptide or a Y-Z-; or $R_2$ and $R_3$, together with the nitrogen to which they are attached, form a substituted or unsubstituted heterocycle or substituted or unsubstituted heteroaryl.

$R_5$ and $R_6$ are each, independently, hydrogen, substituted or unsubstituted aliphatic, substituted or unsubstituted aryl, substituted or unsubstituted aralkyl, substituted or unsubstituted heterocycle, substituted or unsubstituted heterocycloalkyl, substituted or unsubstituted heteroaryl, or substituted or unsubstituted heteroaralkyl. $R_5$ and $R_6$ are optionally joined with the nitrogen with which they are attached to form a 5-, 6-, or 7-membered substituted or unsubstituted heterocycle or substituted or unsubstituted heteroaryl ring.

$R_{34}$ is hydrogen, substituted or unsubstituted aliphatic, substituted or unsubstituted heteroalkyl, substituted or unsubstituted heterocycle, substituted or unsubstituted aryl, substituted or unsubstituted heteroaryl.

$P_2$ has the formula: $-C(R_{35})(R_{36})-S(O)_t-L-R_{12}$.

The symbol "t" represents an integer selected from 0, 1, or 2.

L is a bond, —C(O)—, -L¹-O—, —C(O)NH—, —NH—, —C(O)O—, substituted or unsubstituted alkylene, or substituted or unsubstituted heteroalkylene.

$L^1$ is a bond, substituted or unsubstituted alkylene, or substituted or unsubstituted heteroalkylene.

$R_{12}$ is hydrogen, substituted or unsubstituted aliphatic, substituted or unsubstituted heteroalkyl, substituted or unsubstituted heterocycle, substituted or unsubstituted aryl, or substituted or unsubstituted heteroaryl.

$R_{35}$ and $R_{36}$ are each, independently, hydrogen, halogen, substituted or unsubstituted aliphatic, substituted or unsubstituted heteroalkyl, substituted or unsubstituted heterocycle, substituted or unsubstituted aryl, or substituted or unsubstituted heteroaryl.

In another aspect of the present invention, the β-secretase inhibitor compounds of the invention can be employed in methods to decrease memapsin 2 β-secretase activity, decrease hydrolysis of a β-secretase site of a memapsin 2 β-secretase substrate, and/or decrease the accumulation of β-amyloid protein relative to the amount of memapsin 2 β-secretase activity, hydrolysis of a β-secretase site, and accumulation of β-amyloid protein, respectively, in the absence of the β-secretase inhibitor.

In another aspect, the present invention provides pharmaceutical compositions comprising a memapsin 2 β-secretase inhibitor compound of the invention or a memapsin 2 β-secretase inhibitor compound in combination with a pharmaceutically acceptable carrier.

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

DETAILED DESCRIPTION OF THE INVENTION

Abbreviations and Definitions

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The term "aliphatic" as used herein means straight-chain, branched $C_1$-$C_{12}$ or cyclic $C_3$-$C_{12}$ hydrocarbons which are completely saturated or which contain one or more units of unsaturation but which are not aromatic. For example, suitable aliphatics include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", used alone or as part of a larger moiety, includes both straight, branched, or cyclic saturated hydrocarbon chains containing one to twelve carbon atoms. Preferably, alkyl groups are straight chain hydrocarbons having from one to about four carbons.

An "alkylene," as used herein, is an alkyl group that has two points of attachment to another moiety, such as methylene.

A "heteroalkyl," as used herein, is an alkyl group in which one or more carbon atoms is replaced by a heteroatom.

A "hydroxyalkyl," as used herein, is an alkyl group that is substituted with one or more hydroxy groups.

The term "aryl" used alone or as part of a larger moiety as in "aralkyl" or "aralkoxy", are carbocyclic aromatic ring systems (e.g. phenyl), fused polycyclic aromatic ring systems (e.g., naphthyl and anthracenyl) and aromatic ring systems fused to carbocyclic non-aromatic ring systems (e.g., 1,2,3,4-tetrahydronaphthyl and indanyl) having five to about fourteen carbon atoms.

The term "heteroatom" refers to any atom other than carbon or hydrogen. Preferred heteroatoms are nitrogen, oxygen, sulfur, and phosphorus and includes, for example, any oxidized form of nitrogen and sulfur, and the quaternized form of any basic nitrogen.

The term "heterocycle", as used herein includes non-aromatic ring systems having five to fourteen members, preferably five to ten, in which one or more ring carbons, preferably one to four, are each replaced by a heteroatom. Examples of heterocyclic rings include, tetrahydrofuranyl, tetrahydropyrimidin-2-one, pyrrolidin-2-one, hexahydro-cyclopenta[b]furanyl, hexahydrofuro[2,3-b]furanyl, tetrahydropyranyl, tetrahydropyranone, [1,3]-dioxanyl, [1,3]-dithianyl, tetrahydrothiophenyl, morpholinyl, thiomorpholinyl, pyrrolidinyl, pyrrolidinone, piperazinyl, piperidinyl, and thiazolidinyl. Also included within the scope of the term "heterocycle", as it is used herein, are groups in which a non-aromatic heteroatom-containing ring is fused to one or more aromatic or non-aromatic rings, such as in an indolinyl, chromanyl, phenantrhidinyl, or tetrahydroquinolinyl, where the radical or point of attachment is on the non-aromatic heteroatom-containing ring. Preferred heterocycles are tetrahydrofuranyl, tetrahydropyranyl, pyrrolidinyl, tetrahydropyrimidin-2-one, and pyrrolidin-2-one.

The term "heteroaryl", used alone or as part of a larger moiety as in "heteroaralkyl" or "heteroarylalkoxy", refers to aromatic ring system having five to fourteen members and having at least one heteroatom. Preferably a heteroaryl has from one to about four heteroatoms. Examples of heteroaryl rings include pyrazolyl, furanyl, imidazolyl, isoxazolyl, oxadiazolyl, oxazolyl, pyrrolyl, pyridyl, pyrimidinyl, purinyl, pyridazinyl, pyrazinyl, thiazolyl, thiadiazolyl, isothiazolyl, triazolyl, thienyl, 4,6-dihydro-thieno[3,4-c]pyrazolyl, 5,5-dioxide-4,6-dihydrothieno[3,4-c]pyrazolyl, thianaphthenyl, 1,4,5,6,-tetrahydrocyclopentapyrazolyl, carbazolyl, benzimidazolyl, benzothienyl, benzofuranyl, indolyl, azaindolyl, indazolyl, quinolinyl, benzotriazolyl, benzothiazolyl, benzothiadiazolyl, benzooxazolyl, benzimidazolyl, isoquinolinyl, isoindolyl, acridinyl, and benzoisazolyl. Preferred heteroaryl groups are pyrazolyl, furanyl, pyridyl, quinolinyl, indolyl and imidazolyl.

A "heteroazaaryl" is a heteroaryl in which at least one of the heteroatoms is nitrogen. Exemplary heteroazaaryl groups are pyrazolyl, imidazolyl, isoxazolyl, oxadiazolyl, oxazolyl, pyrrolyl, pyridyl, pyrimidyl, pyridazinyl, thiazolyl, triazolyl, benzimidazolyl, quinolinyl, benzotriazolyl, benzooxazolyl, benzimidazolyl, isoquinolinyl, indolyl, isoindolyl, and benzoisazolyl. Pyrazolyl is an exemplary heteroazaaryl.

An "aralkyl" group, as used herein, is an aryl substituent that is linked to a compound by a straight chain or branched alkyl group having from one to twelve carbon atoms.

Exemplary aralkyl groups are benzyl and indanylmethyl.

A "heterocycloalkyl" group as used herein, is a heterocycle substituent that is linked to a compound by a straight chain or branched alkyl group having from one to twelve carbon atoms. Exemplary heterocycloalkyl groups are tetrahydrofuranylmethyl and pyrrolidinylmethyl.

A "heteroaralkyl" group, as used herein, is a heteroaryl substituent that is linked to a compound by a straight chain or branched alkyl group having from one to twelve carbon atoms. Exemplary heteroaralkyl groups are pyrazolylmethyl, 2-pyrazolylethyl, 2-pyrazolyl-1-methylethyl, and 2-pyrazolyl-1-isopropylethyl.

An "alkoxy" group, as used herein, is a straight chain or branched or cyclic $C_1$-$C_{12}$ or a cyclic $C_3$-$C_{12}$ alkyl group that is connected to a compound via an oxygen atom. Examples of alkoxy groups include but are not limited to methoxy, ethoxy, propoxy, isopropoxy, and t-butoxy.

A "heterocyclooxy," as used herein, is a heterocyclic group that is attached to a molecule via an oxygen substituent.

An "aralkoxy" group, as used herein, is a aralkyl group that is attached to a compound via an oxygen substituent on the $C_1$-$C_{12}$ alkyl portion of the aralkyl. An exemplary arylalkoxy is phenylmethoxy.

A "heteroaralkoxy" group, as used herein, is a heteroaralkyl group that is attached to a compound via an oxygen substituent on the $C_1$-$C_{12}$ alkyl portion of the heteroaralkyl. Exemplary arylalkoxy inlcude pyrazolylmethoxy and 2-pyrazolylethoxy.

A "heterocycloalkoxy" group, as used herein, is a heterocycloalkyl group that is attached to a compound via an oxygen substituent on the $C_1$-$C_{12}$ alkyl portion of the heteroaralkyl.

An "alklysulfanylalkyl" group, as used herein, is a sulfur atom that is linked to two $C_1$-$C_{12}$ alkyl groups, wherein one of the alkyl groups is also linked to a compound.

A halogen is a —F, —Cl, —Br, or —I.

A "haloalkyl" is an alkyl group that is substituted by one or more halogens.

A "haloalkoxy" is an alkoxy group that is substituted with one or more halogens.

An "aryl" (including aralkyl, aralkoxy and the like) or heteroaryl (including heteroaralkyl and heteroaralkoxy and the like) may contain one or more substituents. Examples of suitable substituents include aliphatic groups, aryl groups, haloalkoxy groups, heteroaryl groups, halo, hydroxy, $OR_{24}$, $COR_{24}$, $COOR_{24}$, $NHCOR_{24}$, $OCOR_{24}$, benzyl, haloalkyl (e.g., trifluoromethyl and trichloromethyl), cyano, nitro, $SO_3^-$, SH, $SR_{24}$, $NH_2$, $NHR_{24}$, $NR_{24}R_{25}$, $NR_{24}S(O)_2$—$R_{25}$, and COOH, wherein $R_{24}$ and $R_{25}$ are each, independently, an aliphatic group, an aryl group, or an aralky group. Other substituents for an aryl or heteroaryl group include —$R_{26}$, —$OR_{26}$, —$SR_{26}$, 1,2-methylene-dioxy, 1,2-ethylenedioxy, protected OH (such as acyloxy), phenyl (Ph), substituted Ph, —O(Ph), substituted —O(Ph), —$CH_2$(Ph), substituted —$CH_2CH_2$(Ph), substituted —$CH_2CH_2$(Ph), —$NR_{26}R_{27}$, —$NR_{26}CO_2R_{27}$, —$NR_{26}NR_{27}C(O)R_{28}$, —$NR_{26}R_{27}C(O)NR_{28}R_{29}$, —$NR_{26}NR_{27}CO_2R_{28}$, —$C(O)C(O)R_{26}$, —$C(O)CH_2C(O)R_{26}$, —$CO_2R_{26}$, —$C(O)R_{26}$, —$C(O)NR_{26}R_{27}$, —$OC(O)NR_{16}R_{27}$, —$S(O)_2R_{26}$, —$SO_2NR_{26}R_{27}$, —$S(O)R_{26}$, —$NR_{26}SO_2NR_{26}R_{27}$, —$NR_{26}SO_2R_{27}$, —$C(=S)NR_{26}R_{27}$, —$C(=NH)$—$NR_{26}R_{27}$, —$(CH_2)_yNHC(O)R_{26}$, wherein $R_{26}$, $R_{27}$ and $R_{28}$ are each, independently, hydrogen, a substituted or unsubstituted heteroaryl or heterocycle, phenyl (Ph), substituted Ph, —O(Ph), substituted —O(Ph), —$CH_2$ (Ph), or substituted —$CH_2$ (Ph); and y is 0-6.

Examples of substituents on the aliphatic group or the phenyl group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Preferred substitutents for a heteroaryl group such as a pyrazole group, are a substituted or unsubstituted aliphatic, —$OR_9$, —$R_{23}$—O—$R_9$, a halogen, a cyano, a nitro, $NR_9R_{10}$, guanidino, —$OPO_3^{-2}$, —$PO_3^{-2}$, —$OSO_3^-$, —$S(O)_gR_9$, —$OC(O)R_9$, —$C(O)R_9$, —$C(O)_2R_9$, —$NR_9C(O)R_{10}$, —$C(O)NR_9R_{10}$, —$OC(O)NR_9R_{10}$, —$NR_9C(O)_2R_{10}$ a substituted or unsubstituted aryl, a substituted or unsubstituted aralkyl, a substituted or unsubstituted heteroaryl, a substituted or unsubstituted heteroaralkyl, a substituted or unsubstituted heterocycle, or a substituted or unsubstituted heterocycloalkyl, wherein $R_9$ and $R_{10}$ are each, independently, H, an aliphatic group, an aryl, an aralkyl, a heterocycle, a heterocycloalkyl, a heteroaryl or a heteroaralkyl, wherein the aliphatic group, aryl, aralkyl, heterocycle, heterocyclalkyl, heteroaryl or heteroaralkyl are optionally substituted with one or more aliphatics.

An aliphatic, an alkylene, the carbon atoms of a heteroalkyl, and a heterocycle (including heterocycloalkyl, hetorcyclooxy, and heterocycloalkoxy) may contain one or more substituents. Examples of suitable substituents on the saturated carbon of an aliphatic group of a heterocycle include those listed above for an aryl or heteroaryl group and the following: =O, =S, =$NNHR_{29}$, =$NNR_{29}R_{30}$, =$NNHC(O)R_{29}$, =$NNHCO_2$(alkyl), =$NNHSO_2$(alkyl), or =$NR_{29}$, where each $R_{29}$ and $R_{30}$ are each, independently, selected from hydrogen, an unsubstituted aliphatic or a substituted aliphatic. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, thioalkyl, nitro, cyano, carboxy, alkoxycarbonyl, alkylcarbonyl, hydroxy, haloalkoxy, or haloalkyl.

Suitable substitutents on the nitrogen of a non-aromatic heterocycle or on an unsaturated nitrogen of a heteroaryl include —$R_{31}$, —$NR_{31}R_{32}$, —$C(O)R_{31}$, —$CO_2R_{31}$, —$C(O)C(O)R_{31}$, —$C(O)CH_2C(O)R_{31}$, —$SO_2R_{31}$, —$SO_2NR_{31}R_{32}$, —$C(=S)NR_{31}R_{32}$, —$C(=NH)$—$NR_{31}R_{32}$, and —$NR_{31}SO_2R_{32}$; wherein $R_{31}$ and $R_{32}$ are each, independently, hydrogen, an aliphatic, a substituted aliphatic, phenyl (Ph), substituted Ph, —O(Ph), substituted —O(Ph), —$CH_2$(Ph), or a heteroaryl or heterocycle. Examples of substituents on the aliphatic or the phenyl ring include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

A "hydrophobic" group is a group that does not reduce the solubility of a compound in octane or increases the solubility of a compound in octane. Examples of hydrophobic groups include aliphatic groups, aryl groups, and aralkyl groups.

As used herein, the term "natural amino acid" refers to the twenty-three natural amino acids known in the art, which are as follows (denoted by their three letter acronym): Ala, Arg, Asn, Asp, Cys, Cys-Cys, Glu, Gln, Gly, His, Hyl, Hyp, Ile, Leu, Lys, Met, Phe, Pro, Ser, Thr, Trp, Tyr, and Val. The term "side-chain of an amino acid", as used herein, is the substituent on the alpha-carbon of a natural amino acid.

The term "non-natural amino acid" refers to compounds of the formula $NH_2$—$C(R_{32})_2$—COOH, where $R_{32}$ for each occurrence is, independently, any side chain moiety recognized by those skilled in the art; examples of non-natural amino acids include, but are not limited to: hydroxyproline, homoproline, 4-amino-phenylalanine, norleucine, cyclohexylalanine, α-aminoisobutyric acid, N-methyl-alanine, N-methyl-glycine, N-methyl-glutamic acid, tert-butylglycine, α-aminobutyric acid, tert-butylalanine, ornithine, α-aminoisobutyric acid, 2-aminoindane-2-carboxylic acid, etc. and the derivatives thereof, especially where the amine nitrogen has been mono- or di-alkylated.

A peptide substituent is a sequence of natural or non-natural amino acids that are linked together via an amide bond which is formed by reaction of the α-amine of one amino acid with the α-carboxylic acid of an adjacent amino acid. Preferably, a peptide sequence includes only natural amino acids. In one embodiment, a peptide substituent is a sequence of about 6 natural amino acids. In another embodiment, a peptide substituent is a sequence of 2 natural amino acids. In yet another embodiment, a peptide substituent is 1 natural amino acid.

A "transition state isostere," or "isostere," as used herein, is a compound having peptidyl component where at least one amide linkage between two consecutive natural or non-natural amino acids has been modified such that the —NH— group of the amide has been replaced with a —CH$_2$— and the carbonyl of the amide group has been replaced with a —CH(OH)—. This isostere is also referred to herein as a "hydroxyethylene isostere" because the amide linkage between a pair of amino acids of a peptide is modified to form a hydroxyethylene linkage between the amino acids. A hydroxyethylene group is an isostere of the transition state of hydrolysis of an amide bond. Preferably, an isostere has only one modified amide linkage.

The compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The compounds of the present invention which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

The compounds of the present invention may contain one or more chiral centers, and exist in different optically active forms. When compounds contain one chiral center, the compounds exist in two or more enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the present invention contains more than one chiral center, it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer and mixtures thereof.

"Memapsin-2," as used herein, refers to proteins identified by National Center for Biotechnology Information ("NCBI") accession number NP_036236 (sometimes referred to as "β-site APP-cleaving enzyme 1" or "BACE-1"), including homologs, isoforms and subdomains thereof that retain proteolytic activity. Sequence identities of active memapsin 2 proteins and protein fragments (and nucleic acid coding sequences thereof) have been previously disclosed and discussed in detail in copending U.S. Application No. 20040121947, and International Application No. PCT/US02/34324 (Publication No. WO 03/039454), which are herein incorporated by reference for all purposes in their entirety.

"Memapsin-1," as used herein, refers to proteins identified by the National Center for Biotechnology Information ("NCBI") accession number NP_036237 (sometimes referred to as "β-site APP-cleaving enzyme 2" or "BACE-2") and/or those previously disclosed and discussed in detail in copending U.S. Application No. 20040121947, and International Application No. PCT/USO2/34324 (Publication No. WO 03/039454), incorporated by reference herein in their entirety for all purposes, including homologs, isoforms and subdomains thereof that retain proteolytic activity.

"Cathepsin D," as used herein, refers to proteins identified by National Center for Biotechnology Information ("NCBI") accession number NP_036236 (sometimes referred to as "β-site APP-cleaving enzyme 1" or "BACE-1") and or proteins identified by Enzyme Structure Database subclass EC 3.4.23.5., including homologs, isoforms and subdomains thereof that retain proteolytic activity.

A "β-secretase site" is an amino acid sequence that is cleaved by an active memapsin 2 or active fragment thereof. Specific β-secretase sites have also been previously set forth and discussed in detail in copending U.S. Application No. 20040121947, and International Application No. PCT/US02/34324 (Publication No. WO 03/039454), which are herein incorporated by reference for all purposes in their entirety, and include the Swedish mutation sequence, and the native β-amyloid precursor protein cleavage sequence. Thus, β-secretase inhibitors may be tested for their ability to decrease the hydrolysis of the β-secretase site of a substrate, such as the β-amyloid precursor protein, analogs of β-amyloid precursor protein, or fragments of β-amyloid precursor protein.

A "beta-secretase inhibitor" (i.e. β-secretase inhibitor) refers to a compound capable of reducing the proteolytic activity of memapsin-2 relative to the proteolytic activity in the absence of inhibitor.

The terms "a" or "an," as used in herein means one or more. In addition, the phrase "substituted with a[n]," as used herein, means the specified group may be substituted with one or more of any or all of the named substituents. For example, where a group, such as an aliphatic is "substituted with an oxy, halogen, —CN, —OH, acetyl, aliphatic, heteroalkyl, heterocycle, aryl, or heteroaryl;" the group may contain one or more oxy, halogen, —CN, —OH, acetyl, aliphatic, heteroalkyl, heterocycle, aryl, and/or heteroaryl group.

Where a substituent is attached to the remainder of a molecule by a "bond," the "bond" is a bond.

β-Secretase Inhibitors

In one aspect, the present invention provides a β-secretase inhibitor compound represented by the following structural formula:

In the Formula (I) above, Y is a carrier moiety. Z is selected from a bond, —OP(O)$_2$O—, —C(O)OR$_{33}$—, —C(O)NHR$_{33}$—, —S(O)$_2$NHR$_{33}$—, substituted or unsubstituted aliphatic, or substituted or unsubstituted heteroalkylene. $R_{33}$ is a bond or an alkylene. The symbol "k" is 0 or an integer from 1 to 5.

$A_1$ is a moiety represented by the following structural formula:

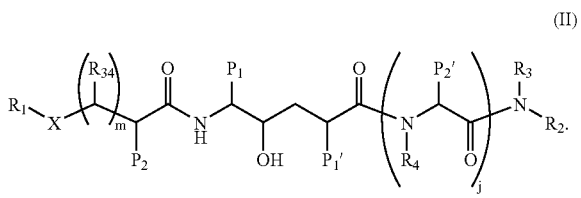

or optical isomers, diastereomers, or pharmaceutically acceptable salts of $A_1$.

In Formula (II), X is —C(O)—, —S(O)$_n$—, or —NH—C(O)—. The symbol "n" represents 1 or 2, "m" is 0, 1, 2, 3, 4, or 5, and "j" is 0 or 1.

$P_1$ is selected from a substituted or unsubstituted aliphatic, substituted or unsubstituted hydroxyalkyl, substituted or unsubstituted aryl, substituted or unsubstituted aralkyl, substituted or unsubstituted heteroaryl, substituted or unsubstituted heteroaralkyl, substituted or unsubstituted heterocycloalkyl, or substituted or unsubstituted alkylsulfanylalkyl.

$P_1'$, and $P_2'$ are each, independently, a substituted or unsubstituted aliphatic, substituted or unsubstituted heteroalkyl, substituted or unsubstituted aryl, substituted or unsubstituted aralkyl, substituted or unsubstituted heteroaryl, substituted or unsubstituted heteroaralkyl, substituted or unsubstituted heterocycle, or substituted or unsubstituted heterocycloalkyl.

$R_1$ is selected from a substituted or unsubstituted aliphatic, substituted or unsubstituted alkoxy, substituted or unsubstituted aryl, substituted or unsubstituted aralkyl, substituted or unsubstituted heterocycle, substituted or unsubstituted heterocycloalkyl, substituted or unsubstituted heterocyclooxy, substituted or unsubstituted heterocycloalkoxy, substituted or unsubstituted heteroaryl, substituted or unsubstituted heteroaralkyl, substituted or unsubstituted heteroaralkoxy, or —NR$_5$R$_6$; or $R_1$, together with X, is a peptide or Y-Z-.

$R_4$ is hydrogen or a substituted or unsubstituted aliphatic.

$R_2$ and $R_3$ are each, independently, hydrogen, a substituted or unsubstituted aliphatic, substituted or unsubstituted aryl, substituted or unsubstituted aralkyl, substituted or unsubstituted heterocycle, substituted or unsubstituted heterocycloalkyl, substituted or unsubstituted heteroaryl, and substituted or unsubstituted heteroaralkyl; or one of $R_2$ and $R_3$, together with the nitrogen to which it is attached, may optionally form a peptide or Y-Z-. $R_2$ and $R_3$, together with the nitrogen to which they are attached, may also form a substituted or unsubstituted heterocycle or substituted or unsubstituted heteroaryl.

$R_5$ and $R_6$ are each, independently, hydrogen, substituted or unsubstituted aliphatic, substituted or unsubstituted aryl, substituted or unsubstituted aralkyl, substituted or unsubstituted heterocycle, substituted or unsubstituted heterocycloalkyl, substituted or unsubstituted heteroaryl, or substituted or unsubstituted heteroaralkyl. $R_5$ and $R_6$ are optionally joined with the nitrogen with which they are attached to form a 5-, 6-, or 7-membered substituted or unsubstituted heterocycle or substituted or unsubstituted heteroaryl ring.

$R_{34}$ is hydrogen, substituted or unsubstituted aliphatic, substituted or unsubstituted heteroalkyl, substituted or unsubstituted heterocycle, substituted or unsubstituted aryl, substituted or unsubstituted heteroaryl.

$P_2$ has the formula: —C(R$_{35}$)(R$_{36}$)—S(O)$_t$-L-R$_{12}$.

The symbol "t" represents an integer selected from 0, 1, or 2.

L is a bond, —C(O)—, -L$^1$-O—, —C(O)NH—, —NH—, —C(O)O—, substituted or unsubstituted alkylene, or substituted or unsubstituted heteroalkylene.

L$^1$ is a bond, substituted or unsubstituted alkylene, or substituted or unsubstituted heteroalkylene.

$R_{12}$ is hydrogen, substituted or unsubstituted aliphatic, substituted or unsubstituted heteroalkyl, substituted or unsubstituted heterocycle, substituted or unsubstituted aryl, or substituted or unsubstituted heteroaryl.

$R_{35}$ and $R_{36}$ are each, independently, hydrogen, halogen, substituted or unsubstituted aliphatic, substituted or unsubstituted heteroalkyl, substituted or unsubstituted heterocycle, substituted or unsubstituted aryl, or substituted or unsubstituted heteroaryl.

In some embodiments, if "t" is 1 or 2, then L is a bond, -L$^1$-O—, —NH—, substituted or unsubstituted alkylene, or substituted or unsubstituted heteroalkylene.

In an exemplary embodiment, L is a bond, —C(O)—, -L$^1$-O—, —C(O)NH—, —NH—, —C(O)O—, or alkylene. L may also be a bond, -L$^1$-O—, or $C_1$-$C_5$ alkylene. Alternatively, L$^1$ may be a $C_1$-$C_5$ alkyl. L may also be —O—. In some embodiments, L is —O—CH$_2$—. In others, L is —CH$_2$—. L may also be a bond.

In one embodiment, $R_{12}$ is selected from aliphatic; heteroalkyl; heterocycle; aryl; heteroaryl; aliphatic substituted with an oxy, halogen, —CN, —OH, acetyl, aliphatic, heteroalkyl, heterocycle, aryl, or heteroaryl; heteroalkyl substituted with an oxy, halogen, —CN, —OH, acetyl, aliphatic, heteroalkyl, heterocycle, aryl, or heteroaryl; heterocycle substituted with an oxy, halogen, —CN, —OH, acetyl, aliphatic, heteroalkyl, heterocycle, aryl, or heteroaryl; aryl substituted with an oxy, halogen, —CN, —OH, acetyl, aliphatic, heteroalkyl, heterocycle, aryl, or heteroaryl; or heteroaryl substituted with an oxy, halogen, —CN, —OH, acetyl, aliphatic, heteroalkyl, heterocycle, aryl, or heteroaryl. Alternatively, each halogen may be selected from fluorine or chlorine.

$R_{12}$ may also be selected from aliphatic; heteroalkyl; heterocycle; aryl; heteroaryl; aliphatic substituted with an oxy, acetyl, aliphatic, heteroalkyl, or alkylsulfonyl; heteroalkyl substituted with an oxy, —CN, aliphatic, or heteroalkyl; heterocycle substituted with an oxy, acetyl, aliphatic, heteroalkyl, or alkylsulfonyl; aryl substituted with an aliphatic, heteroalkyl, or alkylsulfonyl; or heteroaryl substituted with an aliphatic, heteroalkyl, or alkylsulfonyl.

Alternatively, $R_{12}$ may be a polyether. In an exemplary embodiment, this polyether has the formula:

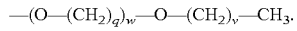

$-(O-(CH_2)_q)_w-O-(CH_2)_v-CH_3$.

The symbols "q" and "v" are independently selected from 1, 2, 3, 4, or 5. In some embodiments, "q" and "v" are, independently, 1 or 2.

The symbol "w" is 1, 2, 3, 4, 5, 6, 7, 8, 9, or 10. Alternatively, "w" is selected from 1, 2, 3, 4, 5, 6, 7, or 8.

In an exemplary embodiment, $P_1$ is selected from a substituted or unsubstituted aliphatic, substituted or unsubstituted heteroalkyl, substituted or unsubstituted aralkyl, or substituted or unsubstituted heteroaralkyl. $P_1$ may also be a substituted or unsubstituted phenylalkyl, or substituted or unsubstituted pyridinylalkyl.

Alternatively, $P_1$ is a $C_1$-$C_5$ alkyl substituted with: halogen, unsubstituted phenyl; unsubstituted pyridinyl; phenyl substituted with a halogen, an —OH, an alkoxy, or an aliphatic; or pyridinyl substituted with a halogen, an —OH, an alkoxy, or an aliphatic.

$P_1$ may also be methyl substituted with a halogen, phenyl, pyridinyl, 3,5-difluorophenyl, 4-hydroxyphenyl, 3-chloro-4-hydroxyphenyl, or 3-chloro-4-mehtoxyphenyl. In some embodiments, $P_1$ is a —$CH_2$—$CH(CH_3)$—$CH_3$. In other embodiments, $P_1$ is an alkyl substituted with a halogen, aryl substituted with a halogen, or arylalkyl substituted with a halogen. $P_1$ may also be selected from an alkyl substituted with a fluorine; an aryl substituted with a fluorine; or an arylalkyl substituted with a fluorine.

In some embodiments, $P_1'$, and $P_2'$ are each, independently, a substituted or unsubstituted aliphatic, substituted or unsubstituted heteroalkyl, substituted or unsubstituted aralkyl, or substituted or unsubstituted heteroaralkyl. $P_1'$ and $P_2'$ may also independently be substituted or unsubstituted aliphatic, or substituted or unsubstituted aryl.

Alternatively, $P_1'$ and $P_2'$ are independently selected from a substituted or unsubstituted aliphatic. $P_1'$ and $P_2'$ may also each independently be $C_1$-$C_5$ alkyl.

$R_5$ and $R_6$ may independently be a hydrogen; unsubstituted aliphatic; unsubstituted aryl; unsubstituted aralkyl; unsubstituted heterocycle; unsubstituted heterocycloalkyl; unsubstituted heteroaryl; unsubstituted heteroaralkyl; or aliphatic, aryl, aralkyl, heteroaryl, heterocycloalkyl, heteroaryl, or heteoraralkyl substituted with a substituent selected from a halogen, unsubstituted aliphatic, unsubstituted aryl, unsubstituted heteroaryl, or unsubstituted heterocycloalkyl.

In some exemplary embodiments, $R_1$ is selected from a substituted aliphatic, —$OR_{15}$, or —$NR_{15}R_{16}$. $R_1$ may also be selected from —$CR_{15}R_{16}$, —$OR_{15}$, or —$NR_{15}R_{16}$.

$R_{15}$ may be hydrogen, an aliphatic, aryl, aralkyl, heterocycle, heterocycloalkyl, heteroaryl or heteroaralkyl, wherein the aliphatic, aryl, aralkyl, heterocycle, heterocycloalkyl, heteroaryl or heteroaralkyl are optionally substituted with an aliphatic, hydroxy, —$OR_9$, halogen, cyano, nitro, —$NR_9R_{10}$, guanidino, —$OPO_3^{-2}$, $PO_3^{-2}$, —$OSO_3^-$, —$S(O)_g$ $R_9$, —$OC(O)R_9$, —$C(O)R_9$, —$C(O)_2R_9$, —$NR_9C(O)R_{10}$, —$C(O)NR_9R_{10}$, —$OC(O)NR_9R_{10}$, —$NR_9C(O)_2R_{10}$, aryl, heteroaryl, heteroaralkyl, and heterocycle. $R_{15}$ may also be substituted or unsubstituted aralkyl, substituted or unsubstituted heteroaralkyl, or substituted or unsubstituted heterocycloalkyl. The symbol "g" represents an integer from 0 to 2.

Alternatively, $R_{15}$ is selected from a $C_1$-$C_3$ alkylene substituted with a substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethylhydantoin.

In some embodiments, $R_{15}$ is a $C_1$-$C_3$ alkylene substituted with a substituted or unsubstituted pyrazolyl, substituted or unsubstituted oxazolyl, substituted or unsubstituted thiazolyl, substituted or unsubstituted furanyl, or substituted or unsubstituted dimethylhydantoin. $R_{15}$ may also be a $C_1$-$C_3$ alkylene substituted with a substituted or unsubstituted 1-pyrazolyl, substituted or unsubstituted 4-oxazolyl, substituted or unsubstituted 2-oxazolyl, substituted or unsubstituted 2-thiazolyl, or substituted or unsubstituted 2-furanyl.

Alternatively, $R_{15}$ is a $C_1$-$C_3$ alkylene substituted with one of the following: 1-pyrazolyl substituted with an aliphatic, or heteroalkyl; 4-oxazolyl substituted with an aliphatic, or heteroalkyl; 2-oxazolyl substituted with an aliphatic, or heteroalkyl; 2-thiazolyl substituted with an aliphatic, or heteroalkyl; or 2-furanyl substituted with an aliphatic, or heteroalkyl. $R_{15}$ may also be a $C_1$-$C_3$ alkylene substituted with 1-pyrazolyl substituted with a $C_1$-$C_5$ alkyl, or 2 to 6 membered heteroalkyl; 4-oxazolyl substituted with a $C_1$-$C_5$ alkyl, or 2 to 6 membered heteroalkyl; 2-oxazolyl substituted with a $C_1$-$C_5$ alkyl, or 2 to 6 membered heteroalkyl; 2-thiazolyl substituted with a $C_1$-$C_5$ alkyl, or 2 to 6 membered heteroalkyl; or 2-furanyl substituted with a $C_1$-$C_5$ alkyl, or 2 to 6 membered heteroalkyl.

In another exemplary embodiment, $R_{15}$ is a $C_1$-$C_3$ alkylene substituted with one of the following: 1-pyrazolyl substituted with a $C_1$-$C_5$ alkyl; 4-oxazolyl substituted with a $C_1$-$C_5$ alkyl; 2-oxazolyl substituted with a $C_1$-$C_5$ alkyl; 2-thiazolyl substituted with a $C_1$-$C_5$ alkyl; or 2-furanyl substituted with a $C_1$-$C_5$ alkyl.

$R_{15}$ may also be methylene substituted with one of: 1-pyrazolyl substituted with a $C_1$-$C_5$ alkyl at the 3 position, the 5 position, or the 3 and 5 position; 4-oxazolyl substituted with a $C_1$-$C_5$ alkyl at the 2 position, the 5-position, or the 2 and 5 position; 2-oxazolyl substituted with a $C_1$-$C_5$ alkyl at the 4 position; 2-thiazolyl substituted with a $C_1$-$C_5$ alkyl at the 4 position; or 2-furanyl substituted with a $C_1$-$C_5$ alkyl at the 5 position.

$R_{16}$ may be hydrogen, an aliphatic, aryl, aralkyl, heterocycle, heterocycloalkyl, heteroaryl or heteroaralkyl, wherein the aliphatic, aryl, aralkyl, heterocycle, heterocycloalkyl, heteroaryl or heteroaralkyl are optionally substituted with an aliphatic, hydroxy, —$OR_9$, halogen, cyano, nitro, —$NR_9R_{10}$, guanidino, —$OPO_3^{-2}$, —$PO_3^{-2}$, —$OSO_3^-$, —$SR_9$, —$S(O)R_9$, —$S(O)_2R_9$, —$OC(O)R_9$, —$C(O)R_9$, —$C(O)_2R_9$, —$NR_9C(O)R_{10}$, —$C(O)NR_9R_{10}$, —$OC(O)NR_9R_{10}$, —$NR_9C(O)_2R_{10}$, aryl, heteroaryl, heteroaralkyl, and heterocycle. $R_{16}$ may also be hydrogen, aliphatic, —$NR_9R_{10}$, or —$OR_9$.

In an exemplary embodiment, $R_9$ and $R_{10}$ are, independently, hydrogen, an aliphatic, aryl, aralkyl, heterocycle, heterocycloalkyl, heteroaryl or heteroaralkyl, wherein the aliphatic, aryl, aralkyl, heterocycle, heterocycloalkyl, heteroaryl or heteroaralkyl are optionally substituted with one or more aliphatics. $R_9$ and $R_{10}$ may also be independently selected from hydrogen, or an aliphatic.

$R_1$ may be an arylalkyl substituted with a halogen. $R_1$ may also be an arylalkyl substituted with a fluorine or chlorine.

$R_2$ may be hydrogen, a substituted or unsubstituted aliphatic, substituted or unsubstituted aryl, substituted or unsubstituted aralkyl, substituted or unsubstituted heterocycle, substituted or unsubstituted heterocycloalkyl, substituted or unsubstituted heteroaryl, and substituted or unsubstituted heteroaralkyl. $R_2$ may also be selected from hydrogen, a substituted or unsubstituted aliphatic, substituted or unsubstituted heteroaryl, and substituted or unsubstituted heteroaralkyl. Alternatively, $R_2$ is hydrogen.

$R_3$ may be selected from hydrogen, a substituted or unsubstituted aliphatic, substituted or unsubstituted aryl, substituted or unsubstituted aralkyl, substituted or unsubstituted heterocycle, substituted or unsubstituted heterocycloalkyl, substituted or unsubstituted heteroaryl, and substituted or unsubstituted heteroaralkyl. $R_3$ may also be hydrogen, a substituted or unsubstituted aliphatic, substituted or unsubstituted heteroaryl, and substituted or unsubstituted heteroaralkyl. Alternatively, $R_3$ is a substituted or unsubstituted aliphatic, substituted or unsubstituted pyridinyl, or substituted or unsubstituted pyridinylalkyl. In some embodiments, $R_3$ is an unsubstituted alkyl, unsubstituted pyridinyl, or pyridinyl substituted with an unsubstituted $C_1$-$C_5$ alkyl. In other embodiments, $R_3$ is an unsubstituted $C_1$-$C_5$ alkyl, unsubstituted pyridinyl, or pyridinyl substituted with an unsubstituted $C_1$-$C_5$ alkyl. Alternatively, $R_3$ is selected from a 2-furanylmethyl, phenylmethyl, indan-2-yl, n-butyl, isopropyl, isobutyl, 1-fluoromethyl-2-fluoroethyl, indol-3-yl, or 3-pyridylmethyl.

$R_2$ and $R_3$, together with the nitrogen to which they are attached, may form a morpholino, piperazinyl, or piperidinyl, wherein the morpholino, piperazinyl and piperidinyl are optionally substituted with one or more aliphatics.

In some embodiments, Y is a peptide. In other embodiments, Y is a tat-peptide, or polyarginine.

In an exemplary embodiment, Z is selected from a bond, —S(O)$_2$NHR$_{33}$—, unsubstituted alkylene, or unsubstituted heteroalkylene.

In some embodiments, the $A_1$ has a stereochemical configuration as shown below:

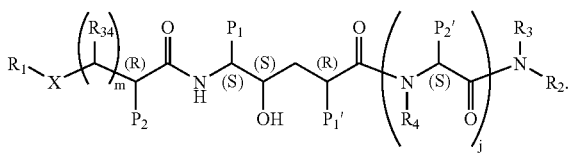

(III)

In Formula (III), $P_1$, $P_2$, $P_1'$, $P_2'$, $R_1$, $R_2$, $R_3$, $R_4$, $R_{34}$, m, and j are as defined above in the discussion of Formula (II).

As described above, $R_1$ may be —CR$_{15}$R$_{16}$. In some embodiments, $R_1$ has the sterochemical configuration shown in the formula below:

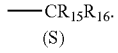

(IV)

In Formula (IV) above, $R^{15}$ and $R^{16}$ are as defined above in the discussion of $R_1$.

Carrier Moieties

In copending U.S. Application No. 20040121947, and International Application No. PCT/US02/34324 (Publication No. WO 03/039454), which are herein incorporated by reference for all purposes, isostere β-secretase inhibitors with and without a carrier moiety were shown to effectively reduce Aβ production in tg2576 mice expressing the Swedish mutation of the human amyloid precursor protein (Hsiao, K., et al., Science 274, 99-102 (1996)). Thus, one of skill in the art will recognize that the compounds of the invention may be administered with or without a carrier moiety.

A "carrier moiety," as used herein, refers to a chemical moiety covalently or non-covalently attached to a β-secretase inhibitor compound of the invention that enhances the ability of the compound to traverse the blood-brain barrier (BBB). The β-secretase inhibitors of the invention may be attached or conjugated to the carrier moiety by covalent interactions (e.g., peptide bonds) or by non-covalent interactions (e.g., ionic bonds, hydrogen bonds, van der Waals attractions).

The blood-brain barrier is a permeability barrier that exists between the extracellular fluid in the brain and the blood in the capillary lumen. The barrier stems from structural differences between the capillaries in the brain and capillaries found in other tissues. Most significant among the structural differences of brain capillaries are the tight junctions between endothelial cells. These specialized tight junctions create a very high trans-endothelial electrical resistance of 1500-2000 ohms/cm$^2$ compared to 3-33 ohms/cm$^2$ in capillary endothelial cells lying outside the brain, reducing the aqueous based para-cellular diffusion observed in other organs (Brightman, M. in Bradbury M W B (ed) *Physiology and Pharmacology of the blood-brain barrier. Handbook of experimental pharmacology* 103, Springer-Verlag, Berlin, (1992); Lo, E. H., et al., *Brain Res. Rev.*, 38:140-148, (2001)). Thus, in some embodiments, the compounds of the present invention are covalently attached to a carrier moiety (represented by the symbol Y in the formulae above).

Any appropriate carrier moiety may be used in the present invention. Useful carrier moieties include, for example, lipophilic carrier moieties, enzymatic substrate carrier moieties, peptidyl carrier moieties, and nanoparticle carrier moieties. Carrier moieties may also include an oligosaccharide unit or other molecule linked to the compound by phosphoester or lipid-ester or other hydrolyzable bonds which are cleaved by glycosidases, phosphatases, esterases, lipases, or other hydrolases in the lysosomes and endosomes. The carrier moieties may contain guanidine, amino, or imidizole functional groups.

Lipophilic Carrier Moieties

Lipophilic carrier moieties increase the overall lipophilicity of a compound, thereby aiding in passage through the BBB. Lipophilicity can be quantified using any suitable approach known in the art. For example, the partition coefficient between octanol and water (log P$_{o/w}$) may be measured thereby indicating the degree of lipophilicity. In some embodiments, the lipophilic carrier moiety has a log P$_{o/w}$ of 1.5-2.5. Lipophilic carrier moieties are widely known in the art and are discussed in detail, for example, in Lambert, D. M., *Eur J Pharm Sci.*, 11:S15-27 (2000). Exemplary lipophilic carrier moieties used to increase the lipophilicity of a compound include modified and unmodified diglycerides, fatty acids, and phospholipids.

Some lipophilic carrier moieties undergo enzyme mediated oxidation after traversing the BBB, resulting in a hydrophilic membrane impermeable form of the carrier moiety that remains trapped behind the BBB (Bodor et al.,

*Pharmacol Ther* 76:1-27 (1997); Bodor et al., *American Chemical Society*, Washington, D.C. pp317-337 (1995); Chen et al., *J Med Chem* 41:3773-3781 (1998); Wu et al., *J Pharm Pharmacol* 54:945-950 (2002)). Exemplary lipophilic carrier moieties that undergo enzyme mediated oxidation include 1,4-dihydrotrigonelline (Palomino et al., *J Med Chem,* 32:622-625 (1989)); alkyl phosphonate carrier moieties that have been successfully used to transport testosterone and zidovudine across the blood-brain barrier (Somogyi, G., et al., *Int J Pharm,* 166:15-26 (1998)); and the lipophilic dihydropyridine carrier moieties that are enzymatically oxidized to the ionic pyridinium salt (Bodor et al., *Science,* 214(18):1370-1372 (1981)).

Peptidyl Carrier Moieties

Peptidyl carrier moieties are moieties partially or wholly composed of a peptide (including polypeptides, proteins, antibodies, and antibody fragments) used to aid in the transport of compounds across the BBB (Wu et al., *J Clin Invest* 100:1804-1812 (1997); U.S. Pat. No. 4,801,575; Pardridge et al., *Adv Drug Deliv Rev,* 36:299-321 (1999)).

Peptidyl carrier moieties may interact with specific peptide transport systems, receptors, or ligands, that target the corresponding ligand or receptor on an endothelial cell of the BBB. Specific transport systems may include either carrier-mediated or receptor-mediated transport across the BBB (U.S. Pat. App. No. 20040110928). Exemplary peptidyl carrier moieties include insulin (Pardridge et al., *Nat Rev Drug Discov,* 1:131-139 (2002)); small peptides such as enkephalin, thyrotropin-releasing hormone, arginine-vassopressin (Bergley, *J Pharm Pharmacol,* 48:136-146 (1996)), Banks et al., *Peptides,* 13:1289-1294 (1992)), Han et al., *AAPS Pharm. Si.,* 2:E6 (2000)); chimeric peptides such as those described in WO-A-89/10134; amino acid derivatives such as those disclosed in U.S. Pat. App. No. 20030216589; tat peptide (Schwarze, S. R., et al., *Science* 285:1569-1572 (1999)); polyarginine peptide (Wender, P. A., et al., *Proc. Natl. Acad. Sci. USA* 97:13003-13008 (2000)); insulin-like-growth factor-1; insulin-like-growth factor-2; transferrin; leptin; low-density lipoprotein (Pardridge, *Nat. Rev. Drug Discov.* 1:131-139 (2002); Colma et al., *Pharm. Res.* 17:266-274 (2000); Pardridge, *Endocrine Rev,* 7:314-330 (1986); Golden, et al., *J Clin Invest,* 99:14-18 (1997); Bickel et al., *Adv. Drug Deliv. Rev.* 46(1-3):247-79 (2001)); and basic fibroblast growth factor (bFGF) (U.S. Pat. App. No. 20040102369).

Copending U.S. Application No. 20040121947, and International Application No. PCT/US02/34324 (Publication No. WO 03/039454), disclose that confocal microscopic images of cells incubated with a fluorescent tat-conjugated isosteric β-secretase inhibitor showed uneven distribution inside cells. Some high fluorescence intensity was associated with the endosome and lysosome intracellular vesicular structures. This indicated that the tat carrier moiety may have been modified by proteases within the lysosome or endosome resulting in an inhibitor that was unable to exit the lysosomal or endosomal compartment. Lysosomes and endosomes contain many proteases, including hydrolase such as cathepsins A, B, C, D, H and L. Some of these are endopeptidases, such as cathepsins D and H. Others are exopeptidases, such as cathepsins A and C, with cathepsin B capable of both endo- and exopeptidase activity. The specificities of these proteases are sufficiently broad to hydrolyze a tat peptide away from the inhibitor compound, thus, hydrolyzing the carrier peptide away from the isosteric inhibitor. Thus, it has been shown that tat and other carrier peptides may be particularly useful for specific delivery of isosteric inhibitors to lysosomes and endosomes. When administered to a mammal by a mechanism such as injections, the conjugated compound will penetrate cells and permeate to the interior of lysosomes and endosomes. The proteases in lysosomes and endosomes will then hydrolyze tat, thereby preventing escape from lysosomes and endosomes.

The peptidyl carrier moiety may be tat or other basic peptides, such as oligo-L-arginine, that are hydrolyzable by lysosomal and endosomal proteases. Specific peptide bonds susceptible to the cleavage of lysosomal or endosomal proteases may be installed, thereby facilitating the removal of the carrier compound from the inhibitor. For example, dipeptides Phe-Phe, Phe-Leu, Phe-Tyr and others are cleaved by cathepsin D.

In one embodiment, the peptidyl carrier molecule includes cationic functional groups, such as the tat-peptide (Schwarze, S. R., et al., *Science* 285: 1569-1572 (1999)), or nine arginine residues (Wender, P. A., et al., *Proc. Natl. Acad. Sci. USA* 97:13003-13008 (2000)). Useful cationic functional groups include, for example, guanidine, amino, and imidazole functional groups. Thus, cationic functional groups also include amino acid side chains such as side chains of lysine, arginine, and histidine residues. In some embodiments, the peptidyl carrier molecule may includes from 1-10 cationic functional groups. When a compound of the invention is conjugated or attached to a carrier moiety, the resulting conjugate may be referred to herein as a "Carrier Peptide-Inhibitor" conjugate or "CPI." The CPI conjugate can be administered to an in vitro sample or to a mammal thereby serving as a transport vehicle for a compound or compounds of the invention into a cell in an in vitro sample or in a mammal. The carrier moieties and CPI conjugates result in an increase in the ability of the compounds of the invention to effectively penetrate cells and the blood brain barrier to inhibit memapsin 2 from cleaving APP to subsequently generate Aβ.

Adsorptive-meditated transcytosis (AME) provides an alternative mechanism whereby peptidyl carrier moieties may cross the BBB. AME differs from other forms of transcytosis in that the initial binding of the carrier moiety to the luminal plasma membrane is mediated through either electrostatic interactions with anionic sites, or specific interactions with sugar residues. Uptake through AME is determined by the C-terminal structure and basicity of the carrier moiety. Exemplary adsorptive peptidyl carrier moieties include peptides and proteins with basic isoeletric points (cationic proteins), and some lectins (glycoprotein binding proteins). See Tamai, I., et al., *J. Pharmacol. Exp. Ther.* 280:410-415 (1997); Kumagai, A. K., et al., *J. Biol. Chem.* 262: 15214-15219 (1987).

Peptidyl carrier moieties also include antibody carrier moieties. Antibody carrier moieties are carrier moieties that include an antibody or fragment thereof. Typically, the antibody or antibody fragment is, or is derived from, a monoclonal antibody. Antibody carrier moieties bind to cellular receptors, or transporters expressed on the luminal surface of brain capillary endothelial cells (U.S. Patent App No. 20040101904). Exemplary antibodies, or fragments thereof, include MAb 83-14 that binds to the human insulin receptor (Pardridge et al., *Pharm Res.* 12:807-816 (1995)); anti-transferrin antibody (Li, J. Y., et al., *Protein Engineering* 12:787-796 (1999)); and monoclonal antibodies that mimic an endogenous protein or peptide which is known to cross the BBB as discussed above.

Nanoparticle Carrier Moieties

Nanoparticle carrier moieties are solid colloidal carriers generally less than a micron in diameter or length. The compound may be encapsulated in, adsorbed onto, or covalently linked to the surface of the nanoparticle carrier moiety. Nanoparticle carrier moieties have been used to successfully deliver a variety of compounds to the brain, including hexapeptide dalagrin, an enkephalin analog; loperamide; tubocerarine; and doxorubicin (Ambikanandan, et al., *J. Pharm Pharmaceut Sci* 6(2):252-273 (2003)). In addition to aiding transport into the brain, nonionic detergents such as polysorbate-80, which can be used to coat the nanoparticle, may be used to inhibit the efflux pump. Zordan-Nudo, T., et al., *Cancer Res,* 53:5994-6000 (1993). Exemplary materials for the manufacture of nanoparticle carrier moieties include polyalkylcyanoacrylate (PACA) (Bertling et al., *Biotechnol. Appl. Biochem.* 13: 390-405 (1991)); polybutylcyanoacrylate (PBCA) (Chavany et al., *Pharm. Res.* 9: 441-449 (1992)); polybutylcyanoacrylate with the peptide-drug complex absorbed onto the surface and coated with polysorbate 80 (Kreuter, J., et al., *Brain Res,* 674:171-174 (1995), Kreuter, J., *Adv Drug Deliv Rev,* 47:65-81, (2001), Kreuter, J., *Curr Med Chem,* 2:241-249 (2002)); polyisohexylcyanoacrylate (PIHCA) (Chavany et al., *Pharm. Res.* 11:1370-1378 (1994)); polyhexylcyanoacrylate (PHCA) (Zobel et al., *Antisense Nucleic Acid Drug Dev.* 7:483-493 (1997)); and PEGylated polycyanoacrylate (Pilar, C., et al., *Pharm Res* 18(8):1157-1166 (2001)).

Linker Moieties

Linker moieties may be used to attach the carrier moiety to the β-secretase inhibitors of the present invention (represented by the symbol Y). For example, steric hinderance between the compound and the carrier can be prevented using polymer technology (e.g. PEGylation) in conjunction with the linker molecule to introduce a long spacer arm (Yoshikawa, T., et al., *J Pharmacol Exp Ther,* 263:897-903, 1992). Linker moieties may be cleavable or non-cleavable.

Cleavable linker molecules include a cleavable moiety. Any appropriate cleavable moiety is useful in the present invention, including for example, phosphoesters, esters, disulfides, and the like. Cleavable moieties also include those moieties capable of being cleaved by biological enzymes, such as peptidases, glycosidases, phosphatases, esterases, lipases, or other hydrolases. Cleavable linker molecules are especially useful where the carrier moiety interferes with the biological activity of the compound. Exemplary cleavable linker molecules include N-succinimidyl-3-2-pyridyldithioproprionate (SPDP), or N-hydrosuccinimide (NHS).

Non-cleavable linker molecules are those that involve the attachment of a carrier moiety to the compound through a linkage that is generally stable to biological conditions and enzymes. Non-cleavable linker molecules are typically used when the carrier moiety does not interfere with the biological activity of the compound. Exemplary non-cleavable linker molecules include thio-ether (e.g., m-maleimidobenzoyl N-hydroxysuccinimide ester (MBS)); amide (e.g., N-hydrosuccinimide (NHS-XX-); extended amide (e.g., N-hydrosuccinimide polyethylene glycol (NHS-PEG); and extended hydrazide linkages (e.g., hydrazide-PEG-biotin-); avidin-biotin; and PEG linkers (Ambikanandan et al., *J. Pharm Pharmaceut Sci* 6(2):252-273 (2003); Pardridge, *Adv Drug Deliv Rev,* 36:299-321 (1999); U.S. Pat. No. 6,287, 792).

Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

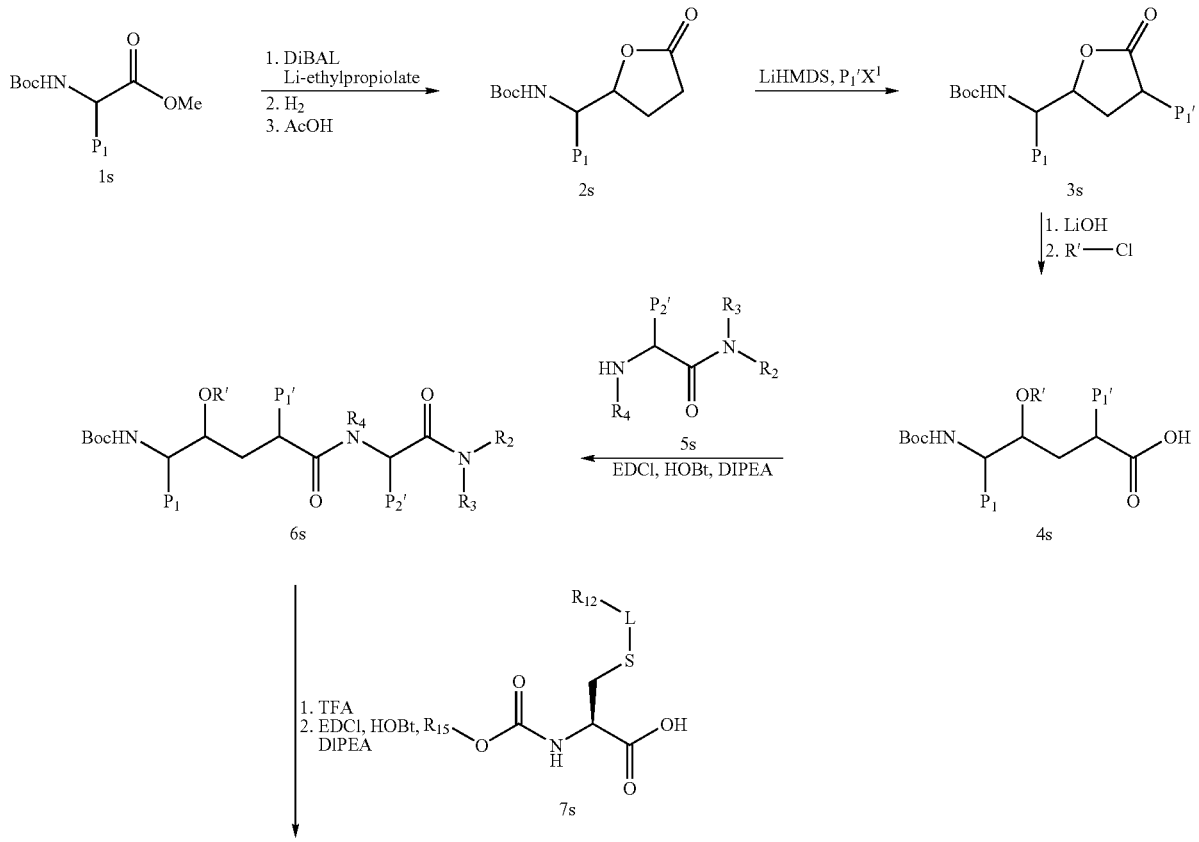

Scheme 1

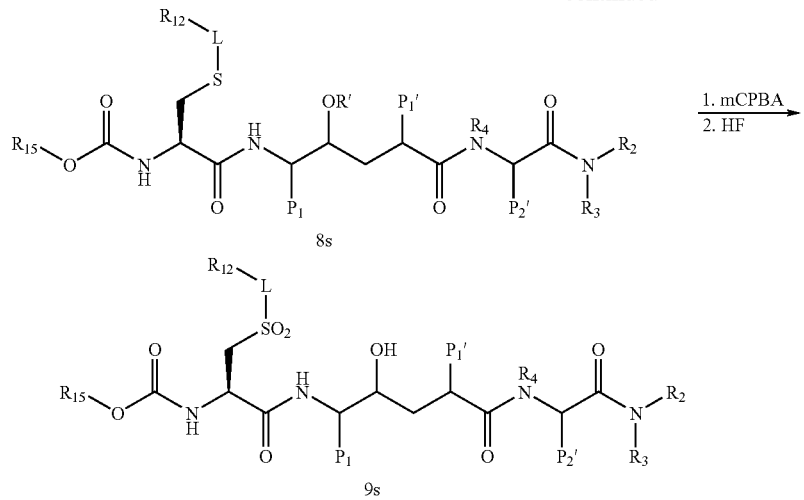

In Scheme 1, L, $P_1$, $P_1'$, $P_2'$, $R_2$, $R_3$, $R_4$, $R_{12}$, and $R_{15}$ are as defined above in the discussion of the inhibitors of the present invention. X' is a halogen (e.g., I, Cl, or Br) and R' is a hydroxyl protecting group (e.g. TBDMS, TBS). Those of skill in the art will understand how to protect a particular functional group, such as a hydroxyl or amine, from interfering with a chosen set of reaction conditions. For examples of useful protecting groups, See Greene et al., PROTECTIVE GROUPS IN ORGANIC SYNTHESIS, John Wiley & Sons, New York, 1991.

In the above scheme, the methyl ester 1s is cyclyzed to the corresponding lactone 2s followed by substitution with the halogenated $P_1'$ group to yield the substituted lactone 3s. Ring opening and protection of the resulting hydroxyl group yields the protected isostere fragment 4s. Amide coupling of the 4s ester and 5s free amine yields the corresponding N-terminal extended isostere 6s. Acid deprotection of the 6s Boc amino group followed by amide coupling to the 7s ester yields the sulfide isostere 8s. For exemplary syntheses of 7s, see Examples section below. Subsequent oxidation and deprotection of 8s yields the corresponding beta secretase inhibitor 9s.

Beta-Secretase Inhibitor Activity

To develop useful β-secretase inhibitors, candidate inhibitors capable of selectively decreasing memapsin 2 activity may be identified in vitro and subsequently tested for their ability to reduce the production of Aβ. The activity of the inhibitor compounds can be assayed utilizing methods known in the art and/or those methods presented herein.

Compounds that decrease memapsin 2 activity may be identified and tested using biologically active memapsin 2, either recombinant or naturally occurring. Memapsin 2 can be found in native cells, isolated in vitro, or co-expressed or expressed in a cell. Measuring the reduction in the memapsin 2 activity in the presence of an inhibitor relative to the activity in the absence of the inhibitor may be perforemd using a variety of methods well known in the art.

For example, the compounds may be tested for their ability to cause a detectable decrease in hydrolysis of a β-secretase site of a peptide in the presence of memapsin 2. These data can be expressed, for example, as $K_i$, $K_i$ apparent, Vi/Vo, or percentage inhibition. $K_i$ is the inhibition equilibrium constant which indicates the ability of compounds to inhibit a given enzyme (such as memapsin 2, memapsin 1, and/or cathepsin D). Numerically lower $K_i$ values indicate a higher affinity of the compounds of the invention for the enzyme. The $K_i$ value is independent of the substrate, and converted from $K_i$ apparent.

$K_i$ apparent is determined in the presence of substrate according to established techniques (see, for example, Bieth, J., Bayer-Symposium V. Proteinase Inhibitors, pp. 463-469, Springer-Verlag, Berlin (1994)). The standard error for the $K_i$ apparent is the error from the nonlinear regression of the Vi/Vo data measured at different concentrations of the compounds of the invention (e.g., between about 10 nM to about 1000 nM) employing well-known techniques (see, for example, Bieth, J., Bayer-Symposium V: Proteinase Inhibitors, pp. 463-469, Springer-Verlag, Berlin (1994), Ermolieff, J., et al., Biochemistry 39:12450-12456 (2000), the teachings of which are incorporated herein by reference in their entirety). Vi/Vo depicts the ratio of initial conversion velocites of an enzyme substrate (Ermolieff, et al., Biochemistry 40:12450-12456 (2000)) by an enzyme in the absence (Vo) or presence (Vi) of an inhibitor. A Vi/Vo value of 1.0 indicates that a compound does not inhibit the enzyme. A Vi/Vo value less than 1.0 indicates that a compound of the invention inhibits enzyme activity.

Once compounds are identified that are capable of reducing the hydrolysis of a secretase site of a peptide in the presence of memapsin 2, the compounds may be further tested for their ability to selectively inhibit memapsin 2 relative to other enzymes. Typically, the other enzyme is a peptide hydrolase, such as memapsin 1 or cathepsin D. Compounds that decrease cathepsin D activity or memapsin 1 activity are tested using biologically active enzyme, either recombinant or naturally occurring. Cathepsin D or memapsin 1 activity can be found in native cells, isolated in vitro, or co-expressed or expressed in a cell. Inhibition by a compound of the invention is measured using standard in vitro or in vivo assays such as those well known in the art or as otherwise described herein.

For example, selectivity may be measured by determining the extent to which memapsin 2 hydrolyzes a substrate peptide compared to the extent to which the same compound inhibits memapsin 1 and/or cathepsin D cleaving of a β-secretase site of a substrate peptide. Exemplary substrate peptides are useful in determining the activity of memapsin 2 includes APP and derivatives thereof, such as FS-2 (Bachem Americas, Torrance, Calif.). Exemplary substrate peptides are useful in determining the activity of memapsin 1 and cathepsin D include, for example, peptides having sequence ELDLAVEFWHDR. These data can be expressed, for example, as $K_i$, $K_i$ apparent, Vi/Vo, or percentage inhibition and depict the inhibition of a compound for memapsin 2 activity relative to memapsin 1 or cathepsin D activity. For example, if the $K_i$ of a reaction between an inhibitor compound of the invention and memapsin 1 or cathepsin D is 1000 and the $K_i$ of a reaction between an inhibitor compound of the invention and memapsin 2 is 100, the inhibitor compound inhibits the β-secretase activity of memapsin 2 ten fold, relative to memapsin 1.

Compounds demonstrating the ability to cause a detectable decrease in hydrolysis of a β-secretase site of a peptide in the presence of memapsin 2 (or, in addition, selectivity of action toward memapsin 2), may be tested in cell models or animal models for their ability to cause a detectable decrease in the amount or production of β-amyloid protein (Aβ). For example, isosteric inhibitors of memapsin 2 have been tested for their ability to decrease Aβ production in cultured cells (copending U.S. Application No. 20040121947, and International Application No. PCT/US02/34324 (Publication No. WO 03/039454)). Briefly, inhibitors may be added to a culture of cells (e.g. human embryonic kidney (HEK293) cells, HeLa cells, Chinese hamster ovary cells, or neuroblastoma line M17 cells) stably transfected with a nucleic acid constructs that encode human APP Swedish mutant (or London mutation or double mutant) and, if needed, a nucleic acid construct encoding human memapsin 2. Immunoprecipitation of Aβ followed by SDS-gel electrophoresis allows detection and quantitation of the amount of Aβ produced in the presence and absence of inhibitor.

In addition to cell cultures, animal models may be used to test inhibitors of memapsin 2 for their ability to decrease Aβ production. For example, an animal (e.g. tg2576 mice) expressing the Swedish mutation of the human amyloid precursor protein (Hsiao, K., et al., Science 274, 99-102 (1996) may be injected intraperitoneally with an inhibitor. The plasma may then be collected and Aβ levels determined by capture ELISA (BioSource International, Camarillo, Calif.).

The presence of inhibitors in organs of animal models or within cellular compartments may be ascertained using a fluorescent tag conjugated to the inhibitor and visualization via confocal microscopy (copending U.S. Application No. 20040121947, and International Application No. PCT/US02/34324 (Publication No. WO 03/039454)).

The sample obtained from the mammal can be a fluid sample, such as a plasma or serum sample; or can be a tissue sample, such as a brain biopsy. The amount of α-amyloid protein or a decrease in the production of β-amyloid protein can be measured using standard techniques (e.g. western blotting and ELISA assays).

Further examples of assays for identifying memapsin 2-β-secretase inhibitors are set forth in the Examples section below. Other methods for assaying the activity of memapsin 2, memapsin 1, and cathepsin D and the activity of agents that decrease the activity of these enzymes are known in the art. The selection of appropriate assay methods is well within the capabilities of those of skill in the art.

Pharmaceutical Compositions

In another aspect, the present invention provides pharmaceutical compositions comprising a memapsin 2 β-secretase inhibitor compound of the invention or a memapsin 2 β-secretase inhibitor compound in combination with a pharmaceutically acceptable carrier. The pharmaceutical compositions include optical isomers, diastereomers, or pharmaceutically acceptable salts of the inhibitors disclosed herein. The memapsin 2 β-secretase inhibitor included in the pharmaceutical composition may be covalently attached to a carrier moiety, as described above. Alternatively, the memapsin 2 β-secretase inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

Formulations

The β-secretase inhibitors of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat Alzheimer's disease, such compositions will contain an amount of active ingredient effective to achieve the desires result (e.g. decreasing β-secretase activity or β-amyloid production). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, including a disease that results in increased activity of memapsin 2 or increased accumulation of β-amyloid protein, whether the mammal suffers from another disease, and its route of administration; size, age, sex, health, body weight, body mass index, and diet of the recipient; nature and extent of symptoms of the disease being treated (e.g., Alzheimer's disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of reducing the activity of memapsin 2 activity, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring memapsin 2 inhibition and adjusting the dosage upwards or downwards, as described above. Adjusting the dose to achieve maximal efficacy in humans based on the methods described above and other methods as are well-known in the art is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

Methods of Reducing the Activity of Memapsin 2 Beta-Secretase

In another aspect of the present invention, the β-secretase inhibitor compounds of the invention can be employed in methods to decrease memapsin 2 activity, decrease hydrolysis of a β-secretase site of a memapsin 2 substrate, and/or decrease the accumulation of β-amyloid protein relative to the amount of memapsin 2 activity, hydrolysis of a β-secretase site, and accumulation of β-amyloid protein, respectively, in the absence of the β-secretase inhibitor.

In an exemplary embodiment, a method of reducing memapsin 2 activity is provided. The method includes contacting a memapsin 2 with a β-secretase inhibitor compound of the present invention. The memapsin 2 may be contacted in any appropriate environment (see below). The memapsin 2 activity is decreased relative the amount of activity in the absence of β-secretase inhibitor.

In another exemplary embodiment, a method is provided of selectively reducing memapsin 2 activity using an inhibitor of the present invention. Selective reduction of the activity of memapsin 2 means that memapsin 2 is not only reduced relative to its activity in the absence of inhibitor, but is reduced to a greater extent as compared to the reduction in activity due to inhibitor action against another peptide hydrolase. For example, as described above, the reduction in activity of an enzyme may be expressed in terms of the inhibitory constant ($K_i$). Where an inhibitor selectively reduces the activity of memapsin 2, the $K_i$ of the reaction between an inhibitor compound of the invention and memapsin 2 is less than the $K_i$ of the reaction between an inhibitor compound of the invention and another peptide hydrolase.

In an exemplary embodiment, the $K_i$ of the reaction between an inhibitor compound of the invention and memapsin 2 is at least 2 times less than the $K_i$ of the reaction between an inhibitor compound of the invention and another peptide hydrolase. In another exemplary embodiment, the $K_i$ of the reaction between an inhibitor compound of the invention and memapsin 2 is at least 10 times less than the K of the reaction between an inhibitor compound of the invention and another peptide hydrolase. In another exemplary embodiment, the $K_i$ of the reaction between an inhibitor compound of the invention and memapsin 2 is at least 100 times less than the $K_i$ of the reaction between an inhibitor compound of the invention and another peptide hydrolase. In another exemplary embodiment, the $K_i$ of the reaction between an inhibitor compound of the invention and memapsin 2 is at least 1000 times less than the $K_i$ of the reaction between an inhibitor compound of the invention and another peptide hydrolase. In another exemplary embodiment, the $K_i$ of the reaction between an inhibitor compound of the invention and memapsin 2 is at least 10000 times less than the $K_i$ of the reaction between an inhibitor compound of the invention and another peptide hydrolase.

In some related embodiments, the inhibitor selectively reduces the activity of memapsin 2 as compared to memapsin 1. In other related embodiments, the inhibitor selectively reduces the activity of memapsin 2 as compared to cathepsin D.

Thus, the present invention provides methods of selectively reducing the activity of memapsin 2. The method includes contacting a memapsin 2 with a β-secretase inhibitor compound of the present invention. In a related embodiment, the method includes contacting the memapsin 2 with a β-secretase inhibitor in the presence of memapsin 1. In an alternative related embodiment, the method includes contacting the memapsin 2 with a β-secretase inhibitor in the presence of cathepsin D. In yet another related embodiment, the method includes contacting the memapsin 2 with a β-secretase inhibitor in the presence of cathepsin D and memapsin 1.

In some embodiments, the activity of memapsin-2 β-secretase may be determined by measuring the hydrolysis of a β-secretase site of a β-secretase substrate. Thus, the present invention also relates to a method of decreasing the hydrolysis of a β-secretase site of a β-secretase substrate by contacting a memapsin 2 with a β-secretase inhibitor compound of the present invention. In some embodiments, the hydrolysis of a β-secretase site is decreased relative the amount of hydrolysis in the absence of the inhibitor. In other embodiments, the hydrolysis is selectively reduced as compared to hydrolysis by memapsin 1 and/or cathepsin D. Thus, a method of selectively decreasing hydrolysis of a β-secretase site of a β-amyloid precursor protein relative to memapsin 1 and/or cathepsin D in a sample is provided. The method includes contacting a memapsin 2 with a β-secretase inhibitor compound of the present invention.

In another embodiment, the present invention relates to a method of decreasing the amount of β-amyloid protein in a sample by contacting the memapsin 2 with an inhibitor compound of the present invention. The amount of α-amyloid protein in a sample is decreased relative the amount of β-amyloid protein in the sample in the absence of the inhibitor. Thus, the accumulation of β-amyloid protein is thereby decreased.

Memapsin 2 may be contacted in any suitable environment or any suitable sample. For example, memapsin 2 may be contacted in vitro, within a cell, or within a mammal. Typically, in vitro solutions are selected such that the components do not substantially interfere with the enzymatic activity of memapsin 2 (e.g. aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact the memapsin 2 with the inhibitor. The cell may contain endogenous memapsin 2 or recombinant memapsin 2 as previously described (copending U.S. Application No. 20040121947, and International Application No. PCT/US02/34324 (Publication No. WO 03/039454)). Exemplary cells include human embryonic kidney (HEK293) cells, HeLa cells, Chinese hamster ovary cells, or neuroblastoma line M17 cells Hela cells, 293 cells. In an exemplary embodiment, the compounds of the invention are administered to a mammal to inhibit the hydrolysis of a β-secretase site of a β-amyloid precursor protein (e.g. a mouse, rabbit or human).

Methods of Treating Alzheimer's Disease

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

Thus, in some embodiments, the invention provides a method of treating Alzheimer's disease in a mammal (e.g., a human) comprising the step of administering to the mammal the β-secretase inhibitors of the invention. The mammals treated with the inhibitors may be human primates, nonhuman primates and/or non-human mammals (e.g., rodents, canines). In one embodiment, the mammal is administered a compound of the invention that reduces β-secretase activity (inhibits memapsin 1 and memapsin 2 activity). In another embodiment, the mammal is administered a compound that selectively reduces memapsin 2 activity. In a related embodiment, the compound has minimal or no effect on reducing memapsin 1 activity. Therefore, the present invention also provides a method of treating Alzheimer's disease in a subject in need thereof, the method comprising administering to the subject a β-secretase inhibitor compound. In an exemplary embodiment, the β-secretase inhibitor compound is part of a pharmaceutical formulation, as described above.

The inhibitor compounds of the invention can be employed in the treatment of diseases or conditions associated with β-secretase activity, which can halt, reverse or diminish the progression of the disease or condition, in particular Alzheimer's disease. In addition to compounds that decrease memapsin 2 activity, compounds that selectively reduce memapsin 2 activity are useful to treat diseases or conditions or biological processes association with memapsin 2 activity rather than diseases or conditions or biological processes associated with both memapsin 2 activity and another peptide hydrolase (such as cathepsin D or memapsin 1).

For example, both memapsin 1 and memapsin 2 cleave amyloid precursor protein (APP) at a β-secretase site to form β-amyloid protein (also referred to herein as Aβ or β-amyloid protein). Thus, both memapsin 1 and memapsin 2 have β-secretase activity (Hussain, I., et al., *J. Biol. Chem.* 276:23322-23328 (2001)). However, the β-secretase activity of memapsin 1 is significantly less than the β-secretase activity of memapsin 2 (Hussain, I., et al., *J. Biol. Chem.* 276:23322-23328 (2001)). Memapsin 2 is localized in the brain, and pancreas, and other tissues (Lin, X., et al., *Proc. Natl. Acad. Sci. USA* 97:1456-1460 (2000)) and memapsin 1 is localized preferentially in placentae (Lin, X., et al., *Proc. Natl. Acad. Sci. USA* 97:1456-1460 (2000)). Alzheimer's disease is associated with the accumulation of Aβ in the brain as a result of cleaving of APP by β-secretase (also referred to herein as memapsin 2, ASP2 and BACE). Thus, methods employing the compounds which selectively inhibit memapsin 2 activity relative to memapsin 1 activity may be important in the treatment of memapsin 2-related diseases, such as Alzheimer's disease. Selective inhibition of memapsin 2 activity makes the compounds of the invention suitable drug candidates for use in the treatment of Alzheimer's disease.

Methods of Administering Beta-Secretase Inhibitors to the CNS

The inhibitor compounds of the present invention may be administered to the CNS through either invasive or non-invasive methods. Non-invasive methods of administration include those methods that do not require the use of a mechanical or physical means to breach the integrity of the blood-brain barrier. Typically, non-invasive methods include the use of immunoliposomes, blood-brain barrier disruption (BBBD), or the olfactory pathway.

Immunoliposomes are liposomes with antibodies or antibody fragments that bind to receptors or transporters expressed on brain capillary endothelial cells attached to the surface of the liposome. An exemplary immunoliposome combines polymer (e.g. PEGylation) technology with that of chimeric peptide technology. For example, the β-secretase inhibitor may be packaged into a unilamellar lipid vesicle containing a $PEG^{2000}$ derivative that contains a reactive groups at one end, for attachment to a complimentary reactive group of an antibody or fragment thereof. Complimentary reactive groups are well known in the art and, include, for example, amine and activated carboxylic acids, thiols and maleimides, and the like (Ambikanandan et al., *J. Pharm Pharmaceut Sci* 6(2):252-273 (2003); Huwyler et al., *Proc. Natl. Acad. Sci. USA*, 93:14164-14169 (1996); and Huwyler et al., *J Pharmcol Exp Ther.* 282:1541-1546 (1997); and U.S. Pat. No. 6,372,250).

Blood-brain barrier disruption is a temporal loss of the integrity of the tight junctions between endothelial cells that comprise the blood brain barrier. Typically, the compound is administered via systemic or intercarotid injection in conjuction with transient blood-brain barrier disruption (BBBD). Exemplary agents useful for inducing BBBD include solvents such as dimethyl sulfoxide (DMSO); ethanol (EtOH); metals (e.g. aluminum); X-irradiation; induction of pathological conditions (e.g. hypertension, hypercapnia, hypoxia, or ischemia); anti-neoplastic agents (e.g. VP-16, cisplatin, hydroxyurea, flurouracil and etoposide); or concurrent systemic administration of the convulsant drug metrazol and the anti-convulsant drug pentobarbital (Ambikanandan et al., *J. Pharm Pharmaceut Sci* 6(2):252-273 (2003)); vasoactive leukotrienes (Black et al., *J Neurosurg*, 81(5):745-751 (1994)); intracarotid infusion of bradykinin, histamine, or the synthetic bradykinin analog RMP-7 (Miller et al., *Science* 297:1116-1118 (2002), Matsukado, et al., *Neurosurgery* 39:125-133 (1996), Abbott, et al., *Mol Med*

Today 2:106-113 (1996), Emerich et al., *Clin Pharmacokinet* 40:105-123 (2001)); hyaluronidase (U.S. Pat App No. 20030215432, Kreil, et al. *Protein Sci.,* 4(9):1666-1669 (1995)); and intercarotid injection of inert hypertonic solutions such as mannitol, or arabinose (Neuwelt, E. A., et al., in Neuwelt E A (ed), *Implications of the Blood Brain Barrier and its Manipulation: Clinical Aspects*. Vol. 2, Plenum Press, New York, (1989), Neuwelt, et al., *J Nucl Med,* 35:1831-1841 (1994), Neuwelt et al., *Pediatr Neurosurg* 21:16-22 (1994), Kroll et al., *Neurosurg,* 42:1083-1099 (1998), Rapoport, *Cell Mol Neurobiol* 20:217-230 (2000), and Doran et al., *Neurosurg* 36:965-970, (1995)).

Olfactory pathway administration is the intranasal delivery of the compound to the olfactory nerves in the upper third of the nasal passages. After intranasal delivery, the compound is transported back along the sensory olfactory neurons to yield significant concentrations in the cerebral spinal fluid (CSF) and olfactory bulb (Thorne et al., *Brain Res,* 692(1-2):278-282 (1995); Thorne et al., *Clin Pharmacokinet* 40:907-946 (2001); Illum, *Drug Discov Today* 7:1184-1189 (2002); U.S. Pat. No. 6,180,603; U.S. Pat. No. 6,313,093; and U.S. Pat App No. 20030215398).

Invasive methods of administration are those methods that involve a physical breach of the blood-brain barrier typically through a mechanical or physical means to introduce the compound into the CSF, or directly into the parenchyma of the brain. Typically, invasive methods of administration may include injection or surgical implantation of the compound.

In injection methods, a needle is used to physically breach the BBB and deliver the compound directly into the CSF. Exemplary injection methods include intraventricular, intrathecal, or intralumbar routes of administration and may also involve infusion of the compound through a reservoir external to the body (Krewson et al., *Brain Res* 680:196-206 (1995); Harbaugh et al., *Neurosurg.* 23(6):693-698 (1988); Huang et al., *J Neurooncol* 45:9-17 (1999); Bobo et al., *Proc Natl Acad Sci USA* 91:2076-2082 (1994); Neuwalt et al., *Neurosurg.* 38(4):1129-1145 (1996)).

In surgical implantation methods, the compound is placed directly into the parenchyma of the brain. Exemplary surgical implantation methods may include incorporation of the compound into a polyanhydride wafer placed directly into the interstitium of the brain (Brem et al., *Sci Med* 3(4): 1-11 (1996); Brem et al., *J Control Release* 74:63-67 (2001)).

Crystallized Complexes

In another aspect, the present invention provides a crystallized complex containing a memapsin 2 protein and a β-secretase inhibitor of the present invention. Memapsin 2 proteins useful in forming co-crystals with isostere compounds (e.g. memapsin 2 protein fragments, transmembrane proteins, etc.) have been previously discussed in detail (copending U.S. Application No. 20040121947, and International Application No. PCT/US02/34324 (Publication No. WO 03/039454)). These memapsin 2 proteins are equally useful in forming crystallized complexes with β-secretase inhibitors of the present invention.

The crystallized complex may be formed employing techniques described in copending U.S. Application No. 20040121947, and International Application No. PCT/US02/34324 (Publication No. WO 03/039454). Briefly, a nucleic acid construct encoding the protein is generated, is expressed in a host cell, such as a mammalian host cell (e.g., Hela cell, 293 cell) or a bacterial host cell (e.g., *E. coli*), is purified and is crystallized with a compound or compounds of the invention. The diffraction resolution limit of the crystallized protein can be determined, for example, by x-ray diffraction or neutron diffraction techniques.

In an exemplary embodiment, the crystallized protein may have an x-ray diffraction resolution limit not greater than about 4.0 Å. The crystallized protein may also have an x-ray diffraction resolution limit not greater than about 4.0 Å, about 3.5 Å, about 3.0 Å, about 2.5 Å, about 2.0 Å, about 1.5 Å, about 1.0 Å, or about 0.5 Å. In some embodiments, the crystallized protein may also have an x-ray diffraction resolution limit not greater than about 2 Å. The diffraction resolution limit of the crystallized protein can be determined employing standard x-ray diffraction techniques.

In an other exemplary embodiment, the β-secretase inhibitor of the crystallized complex is in association with said protein at an $S_3'$ binding pocket, an $S_4'$ binding pocket and/or an $S_4$ binding pocket. $S_3'$, $S_4'$, and $S_4$ binding pockets are discussed in detail in copending U.S. Application No. 20040121947, and International Application No. PCT/US02/34324 (Publication No. WO 03/039454).

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the β-secretase inhibitors of the present invention are equally applicable to the methods of treating disease states and/or the pharmaceutical compositions described herein. All publications, patents, and patent applications cited herein are hereby incorporated by reference in their entirety for all purposes.

EXAMPLES

Example 1

Synthesis of Heterocycle Alcohols

Example 1.1

Methylthiazole Methanol

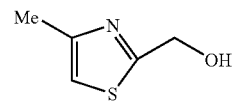

Methylthiazole (1.0 g, 10.1 mmol) in THF at −78° C. was treated with n-BuLi (1.6 M, 7.56 mL) for 30 min, DMF (1.4 mL, 18.2 mmol) was added dropwise. The resulting reaction mixture was warmed to r.t. After the starting material was disappeared (by TLC), the reaction mixture was recooled to 0° C. and LAH (0.69 g, 18.5 mmol) was added. The mixture was warmed to r.t. and stirred for 1 h, the reaction was quenched with aquoues $NH_4Cl$, diluted with EtOAc. The organic solution was separated, extracted twice with EtOAc, dried with $Na_2SO_4$, and concentrated. The residue was purified with flash chromatography to give the corresponding alcohol as a light yellow oil. $^1$H-NMR: (300 MHz, $CDCl_3$), δ: 6.89 (s, 1H); 4.95 (s, 2H); 2.48 (s, 3H).

Example 1.2

Dimethylimidizolyl Methanol and Dimethylpyrazolyl Methanol

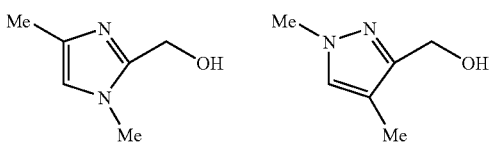

Methylimidizole (5 g, 60.89 mmol) was treated with trimethyl phosphate (3.41 g, 24.36 mmol) and diisopropyl ethylamine at 150° C. for 6 h. The resulting mixture was dissolved in benzene and the solution was stirred with 30% aqueous potassium hydroxide. Envaporation of the solvent from the organic layer and flash chromatography of the residue afforded dimethylmidazole as white solid. Following the same procedure the dimethylpyrazine was also made.

Using the procedure of preparation of methylthiazole methanol the alcohols were made. Dimethylimidizolyl methanol is a white solid. Dimethylpyrazolyl methanol is a light yellow oil. $^1$H-NMR: (300 MHz, CDCl$_3$), δ: 7.24 (s, 1H); 4.65 (s, 2H); 3.89 (s, 3H); 2.07 (s, 3H).

Example 1.3

Methylimidizolyl Methanol, Thiazole Methanol, Methyl Thiodiazolyl Methanol

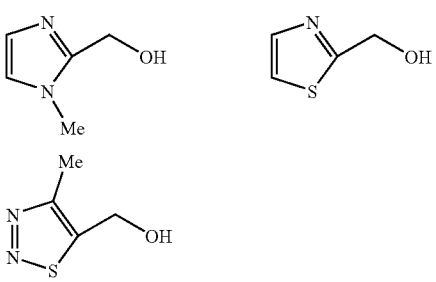

Aldehyde (100 mg, 0.91 mmol) in diethyl ether at 0° C. was added lithium aluminium hydride (51.7 mg, 1.36 mmol), then the resulting mixture was warmed to r.t. After 1 h, the reaction was quenched with Na$_2$SO$_4$.10H$_2$O and stirred for a couple of hours. The organic solution was filtrated. The residue was purified with flash chromatography to give the corresponding alcohol as a white solid. $^1$H-NMR: (300 MHz, CDCl$_3$), δ: 6.86 (m, 2H); 4.57 (s, 2H); 3.88 (br, 1H); 3.65 (s, 3H).

Same as the above procedure to prepare the thiazolyl methanol, a light yellow oil. $^1$H-NMR: (300 MHz, CDCl$_3$), δ: 6.86 (m, 2H); 4.57 (s, 2H); 3.88 (br, 1H); 3.65 (s, 3H).

Methyl thiodiazolyl methanol, a light yellow oil. $^1$H-NMR: (300 MHz, CDCl$_3$), δ: 5.05 (s, 2H); 2.68 (s, 3H).

Thiazolyl methanol, a light yellow oil. $^1$H-NMR: (300 MHz, CDCl$_3$), δ: 7.77 (d, 1H); 7.35 (d, 1H); 4.99 (s, 2H).

Example 1.4

Methyldiazolyl Methanol

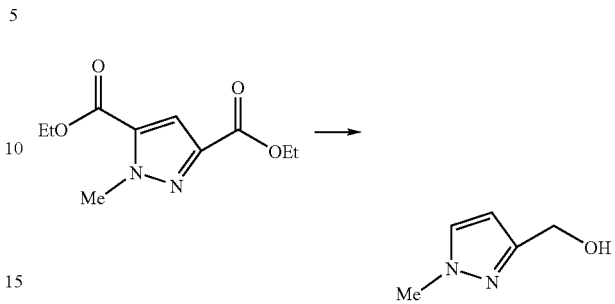

Diethyl pyrazoledicarboxylate (2.0 g, 9.42 mmol) in THF at 0° C. was added NaH (60% in mineral oil, 0.42 g, 10.37 mmol) portionwise. he resulting mixture was warmed to r.t. and stirred overnight. The reaction was quenched with saturated aqueous NH$_4$Cl carefully. The mixture was diluted with EtOAc, separated, and extracted with EtOAc twice. The combined organic layers was dried over Na$_2$SO$_4$, concentrated, and purified by flash chromatography to afford the product as a colorless oil.

The above diester (1.0 g, 4.42 mmol) was dissolved in MeOH, a solution of KOH in MeOH (0.28 g of KOH in 2.5 mL of MeOH) was added, and the mixture was stirred at r.t. for 24 h. After removal of solvent under reduced pressure at low temperature, the residue was dissolved in water and neutralized with aqueous HCl (1M solution). Extraction of the mixture with CHCl$_3$ three times afforded the crude product after concentration of the combined organic layers. Without further purification the crude above product was heated to 210° C. for 30 min. to provide a dark brown oil, which was purified by flash chromatography to give the ester.

The ester was reduced to corresponding alcohol by LAH. $^1$H-NMR: (300 MHz, CDCl$_3$), δ: 7.32 (s, 1H); 6.25 (s, 1H); 4.68 (s, 2H); 3.88 (s, 3H); 2.74 (br, 1H).

Example 1.5

Methyloxazolyl Methanol

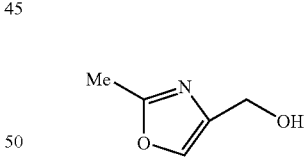

A suspension of ethyl acetamide hydrochloride (0.87 g, 7.1 mmol) in DCM at 0° C. was treated with serine ethyl ester hydrochloride (1 g, 5.9 mmol) and triethylamine (0.82 mL, 5.9 mmol) and the reaction mixture allowed to r.t. After 24 h, the reaction was quenched with water, and the layers were separated. The aqueous layer was extracted with DCM twice, the combined organic layers was concentrated to give a crude product. Without further purification the crude product was treated with DBU/CCl$_4$/Py (6.6 mL/15 mL/22.5 mL) in acetonitrile. After 3 h, the solvent was removed in vacuo, the residue was dissolved in EtOAc, washed with water for three times. The organic layer was dried over Na$_2$SO$_4$, concentrated and the residue was purified by flash chromatography to afford the pure ester, which was reduced by LAH to get the desired alcohol. $^1$H-NMR: (300 MHz, CDCl$_3$), δ: 7.51 (s, 1H); 4.58 (s, 2H); 2.48 (s, 3H).

Example 1.6

Dimethyloxazolyl Methanol

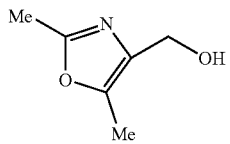

Sodium nitrite (12.2 g, 0.18 mol) in water was added dropwise to a solution of ethyl acetoacetate (19.5 mL, 0.15 mol) in glacial acetic acid at r.t. for 1 h. The resulting mixture was stirred for further 1 h at r.t, 80 mL of water added, and stirring continued for 2 h. The reaction mixture was extracted with ether for three times, washed with aqueous Na HCO$_3$, water and brine. The organic layer was dried, concentrated to afford the crude product. Without further purification, the crude product (6.5 g, 40.8 mmol) in a mixture of acetic anhydrous (19.3 mL, 0.21 mol), acetic acid (58 mL), and 210 mg of Pd/C (10% w/w) was hydrogenated at 50 Psi pressure for 1.5 h. The catalyst and solvent were removed and the residue was triturated with hexanes to give ethyl N-acetylacetoacetate as solid, m.p. 38-40° C.

The above solid product (3.3 g, 17.6 mmol) was treated with thionyl chloride (1.3 mL, 17.6 mmol) in dry benzene at r.t. The mixture was warmed to 30° C. for 1 h, and for 30 min under water-pump vacuum. The residue was diluted with EtOAc and washed with aqueous NaHCO$_3$, water, and brine. The organic layer was dried, concentrated to give the crude product as a brown oil, which was further reduced by LAH to provide the desired alcohol as a light yellow solid. $^1$H-NMR: (300 MHz, CDCl$_3$), δ: 4.51 (s, 2H); 2.58 (s, 3H); 2.43 (s, 3H), 2.31 (s, 3H).

A similar procedure was used to prepare the corresponding ethyl heterocycle:

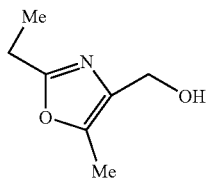

$^1$H-NMR: (300 MHz, CDCl$_3$), δ: 4.51 (s, 2H); 2.75 (m, 2H); 2.31 (s, 3H); 1.33 (m, 3H).

Example 1.7

Dimethylthiazolyl Methanol

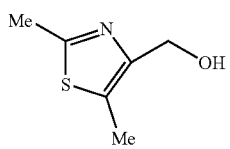

A mixture of ethyl N-acetylacetoacetate (3.6 g, 19.3 mmol) and phosphorus pentasulfide (4.3 g, 9.6 mmol) in toluene was heated to 75° C. for 2 h. The reaction mixture was diluted with EtOAc and quenched with water. The organic layer was separated. The aqueous layer was extracted with EtOAc. The combines organic layers was washed with brine, dried, and concentrated to give the crude ester, which was reduced with LAH without further purification to provide the desired alcohol. $^1$H-NMR: (300 MHz, CDCl$_3$), δ: 4.64 (s, 2H); 3.75 (br, 3H); 2.64 (s, 3H), 2.42 (s, 3H).

A similar procedure was used to prepare the corresponding ethyl heterocycle:

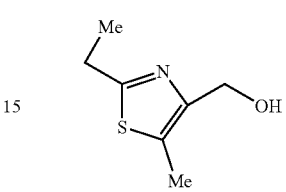

Same procedure as above was used to prepare the alcohol. $^1$H-NMR: (300 MHz, CDCl$_3$), δ: 4.65 (s, 2H); 2.98 (m, 2H); 2.43 (s, 3H); 1.36 (m, 3H).

Example 1.8

Methyloxazaimidizolyl Methanol

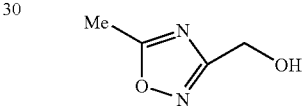

Ethyl chlorooximinoacetate (2 g) in 80 mL of dry diethyl ether was treated with dry ammonia gas at 0° C. The precipitated ammonium chloride was filtered with suction and the filtrate was evaporated under reduced pressure to give the product, m.p. 96-97° C. This compound (1 g) was treated with acetic anhydrous (1.1 mL) in pyridine at reflux condition for 1 h. The solvent was removed and the residue was dissolved in CHCl$_3$. The organic layer was washed with water, aqueous NaHCO3, and brine, dried and concentrated to give the crude product, which was reduced to desired alcohol with NaBH$_4$ in methanol. $^1$H-NMR: (300 MHz, CDCl$_3$), δ: 4.78 (s, 2H); 2.63 (s, 3H).

The procedure below was used to produce the following methyloxazaimidizolyl methanol:

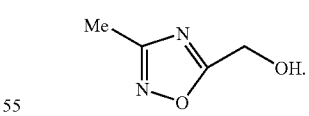

Acetamide oxime (0.95 g, 12.8 mmol) in THF was added NaH (60% in mineral oil, 0.62 g, 15.4 mmol) at r.t. The mixture was then heated up to 80° C. for 10 min and TEMOM protected ethyl glycolate was added. The resulting was heated at this temperature for 2 h. The solvent was removed and the residue was diluted CHCl$_3$ and washed with water and brine. The solvent was removed and the residue was purified with flash chromatography to give the product, which was deprotected with TFA to provide the desired alcohol as a white solid. 1H-NMR: (300 MHz, CDCl$_3$), δ: 4.90 (s, 2H); 2.43 (s, 3H).

Example 2

Preparation of Exemplary Beta-Secretase Inhibitor Compounds

Example 2.1

Synthesis of N-(tert-Butoxycarbonyl)-L-leucine-N'-methoxy-N'-methylamide

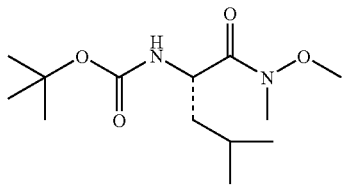

1e

To a stirred solution of N,O-dimethylhydroxyamine hydrochloride (5.52 g, 56.6 mmol) in dry dichloromethane (25 mL) under a $N_2$ atmosphere at 0° C., was added N-methylpiperidine (6.9 mL, 56.6 mmol) dropwise. The resulting mixture was stirred at 0° C. for 30 minutes. In a separate flask, commercially available N-(t-butyloxycarbonyl)-L-leucine (11.9 g, 51.4 mmol) was dissolved in a mixture of tetrahydrofuran (THF) (45 mL) and dichloromethane (180 mL) under a $N_2$ atmosphere. The resulting solution was cooled to −20° C. To this solution was added 1-methylpiperidine (6.9 mL, 56.6 mmol) followed by isobutyl chloroformate (7.3 mL, 56.6 mmol) dropwise. The resulting mixture was stirred for 5 minutes at −20° C. and the above solution of N,O-dimethyl-hydroxylamine was added dropwise. The reaction mixture was stirred at −20° C. for 30 minutes followed by warming to room temperature. The reaction was quenched with water and the layers were separated. The aqueous layer was extracted with $CH_2Cl_2$ (3 times). The combined organic layers were washed with 10% citric acid, saturated sodium bicarbonate, brine, dried over $Na_2SO_4$ and concentrated under reduced pressure. Flash column chromatography (25% ethyl acetate (EtOAc) in hexanes) yielded 1 (13.8 g, 97%). $[\alpha]_D^{23}$-23 (c 1.5, MeOH); $^1$H-NMR (400 MHZ, CDCl$_3$) δ 5.06 (d, 1H, J=9.1 Hz), 4.70 (m, 1H), 3.82 (s, 3H), 3.13 (s, 3H), 1.70 (m, 1H), 1.46-1.36 (m, 2H) 1.41 (s, 9H), 0.93 (dd, 6H, J=6.5, 14.2 Hz); $^{13}$C-NMR (100 MHZ, CDCl$_3$) δ 173.9, 155.6, 79.4, 61.6, 48.9, 42.1, 32.1, 28.3, 24.7, 23.3, 21.5; IR (neat) 3326, 2959, 2937, 2871, 1710, 1666, 1502, 1366, 1251, 1046 cm$^{-1}$; HRMS m/z (M+H)$^+$ calc'd for $C_{13}H_{27}N_2O_4$ 275.1971, found 275.1964.

Example 2.2

Synthesis of N-(tert-Butoxycarbonyl)-L-Leucinal

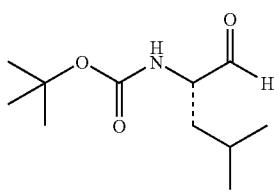

2e

To a stirred suspension of lithium aluminum hydride (LAH) (770 mg, 20.3 mmol) in diethyl ether (60 mL) at −40° C. under $N_2$ atmosphere, was added dropwise a solution of 1e (5.05 g, 18.4 mmol) in diethyl ether (20 mL). The resulting reaction mixture was stirred for 30 minutes followed by quenching with 10% aqueous $NaHSO_4$ (30 mL) and warming to room temperature for 30 minutes. This solution was filtered and the filter cake was washed with diethyl ether (two times). The combined organic layers were washed with saturated sodium bicarbonate, brine, dried over $MgSO_4$ and concentrated under reduced pressure to afford 2e (3.41 g) which was used immediately without further purification. Crude $^1$H-NMR (400 MHZ, CDCl$_3$) δ 9.5 (s, 1H), 4.9 (s, 1H), 4.2 (m, 1H), 1.8-1.6 (m, 2H), 1.44 (s, 9H), 1.49-1.39 (m, 1H), 0.96 (dd, 6H, J=2.7, 6.5 Hz).

Example 2.3

Synthesis of Ethyl (4S,5S)- and (4R,5S)-5-[(tert-Butoxycarbonyl)amino]-4-hydroxy-7-methyloct-2-ynoate

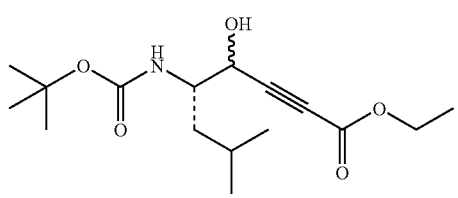

3e

To a stirred solution of ethyl propiolate (801 mL) in THF (2 mL) at −78° C. was added a 1.0 M solution of lithium hexamethyldisilazide (7.9 mL) dropwise over a 5 minutes period. The mixture was stirred for 30 min, after which N-(tert-butoxycarbonyl)-L-leucinal 2e (or N-Boc-L-leucinal) (1.55 g, 7.2 mmol) in 8 mL of dry THF was added. The resulting mixture was stirred at −78° C. for 30 minutes. The reaction was quenched with saturated aqueous $NH_4Cl$ at −78° C. followed by warming to room temperature. Brine was added and the layers were separated. The organic layer was dried over $Na_2SO_4$ and concentrated under reduced pressure. Flash column chromatography (15% EtOAc in hexanes) yielded a mixture of acetylenic alcohols 3e (68%). $^1$H-NMR (300 MHZ, CDCl$_3$) δ 4.64 (d, 1H, J=9.0 Hz), 4.44 (br s, 1H), 4.18 (m, 2H), 3.76 (m, 1H), 1.63 (m, 1H), 1.43-1.31 (m, 2H), 1.39 (s, 9H), 1.29-1.18 (m, 3H), 0.89 (m, 6H); IR (neat) 3370, 2957, 2925, 2854, 1713, 1507, 1367, 1247, 1169, 1047 cm$^{-1}$.

Example 2.3A

Alternative synthesis of Ethyl (4S,5S)- and (4R,5S)-5-[(tert-Butoxycarbonyl)amino]-4-hydroxy-7-methyloct-2-ynoate

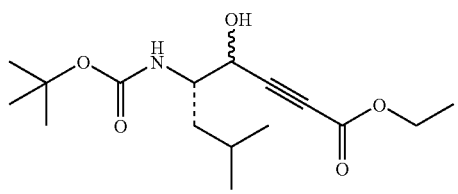

3e

To a stirred solution of DIBAL-H (1.5M in toluene, 28 mL, 42.0 mmol) at −78° C. under argon atmosphere was added of Boc-Valine methyl ester (5.0 g, 20.4 mmol) in toluene (25 mL) dropwise over 25 min (solution A). To a separate solution of LiHMDS (1.0M in tetrahydrofuran, 31 mL, 31.0 mmol) at −78° C. under argon atmosphere was added ethylpropiolate (3.1 mL, 30.6 mmol) dropwise over 5 min (solution B). After stirring at −78° C. for 80 min solution A was transferred quickly via cannulae to solution B. After stirring and additional 15 min at −78° C. the solution was allowed to warm to room temperature. After stirring an additional 3 h at room temperature, the reaction mixture was cooled to −10° C. and quenched with acetic acid (7.5 mL) and stirred for 20 min. The mixture was allowed to warm to room temperature and poured into a mixture of 50 mL ethyl acetate and 50 mL 10% citric acid and stirred for 1 h. The layers were separated and the organic layer washed with $H_2O$ (2×), brine, dried with $Na_2SO_4$, and concentrated to yield a crude oil which was purified by flash column chromatography (20% ethyl acetate in hexanes) to provide 3e (2.0 g, 31%). $^1H$ NMR identical to above procedure.

Example 2.4

(5S,1'S)-5-[1'-[(tert-Butoxycarbonyl)amino]-3'-methylbutyl]dihydrofuran-2(3H)-one (4)

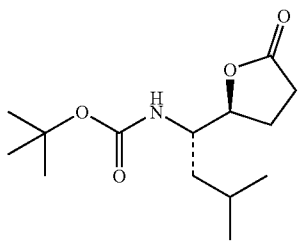

4e

To a stirred solution of 3e (1.73 g, 5.5 mmol) in methanol (MeOH) (20 mL) was added 10% Pd/C (1.0 g). The resulting mixture was placed under a hydrogen balloon and stirred for 1 hour. After this period, the reaction was filtered through a pad of Celite and the filtrate was concentrated under reduced pressure. The residue was dissolved in toluene (20 mL) and acetic acid (100 L). The resulting mixture was refluxed for 6 ours followed by cooling to room temperature and concentrating under reduced pressure. Flash column chromatography (40% diethyl ether in hexanes) yielded 4e (0.94 g, 62.8 mmol) and less than 5% of its diastereomer. Lactone 4: M.p. 74-75° C.; $[\alpha]_D^{23}$ −33.0 (c 1.0, MeOH); lit. (Fray, A. H., et al., *J. Org. Chem.* 51:4828-4833 (1986)) $[\alpha]_D^{23}$−33.8 (c 1.0, MeOH); $^1H$-NMR (400 MHZ, $CDCl_3$) δ 4.50-4.44 (m, 2H), 3.84-3.82 (m, 1H), 2.50 (t, 2H, J=7.8 Hz), 2.22-2.10 (m, 2H), 1.64-1.31 (m, 3H), 1.41 (s, 9H), 0.91 (dd, 6H, J=2.2, 6.7 Hz); $^{13}C$-NMR (75 MHZ, $CDCl_3$) δ 177.2, 156.0, 82.5, 79.8, 51.0, 42.2, 28.6, 28.2, 24.7, 24.2, 23.0, 21.9; IR (neat) 2956, 2918, 2859, 1774, 1695, 1522, 1168 cm$^{-1}$; mass (EI) m/z 294 (M$^+$+Na); HRMS: m/z (M+Na)$^+$ calc'd for $C_{14}H_{25}NO_4Na$, 294.1681, found 294.1690.

Example 2.5

Synthesis of (3R,5S,1'S)-5-[1'-[(tert-Butoxycarbonyl)amino)]-3'-methylbutyl]-3-meth yl-(3H)-dihydrofuran-2-one

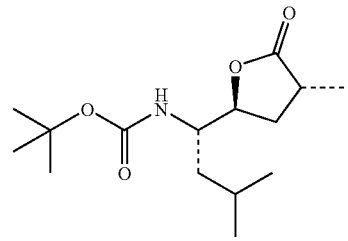

5e

To a stirred solution of lactone 4e (451.8 mg, 1.67 mmol) in THF (8 mL) at −78° C. under a $N_2$ atmosphere, was added dropwise lithium hexamethyldisilazide (3.67 mL, 1.0 M in THF, 3.67 mmol). The resulting mixture was stirred at −78° C. for 30 minutes. Methyl iodide (MeI) (228 mL) was added dropwise and the resulting mixture was stirred at −78° C. for 20 minutes. The reaction was quenched with saturated aqueous $NH_4Cl$ and allowed to warm to room temperature. The reaction mixture was concentrated under reduced pressure and the residue was extracted with EtOAc (three times). The combined organic layers were washed with brine, dried over $Na_2SO_4$ and concentrated under reduced pressure. Flash column chromatography (15% EtOAc in hexanes) yielded 5e (0.36 g, 76%). The stereochemistry of $C_2$-methyl group was assigned based upon NOESY and COSY experiments. Irradiation of the $C_2$-methyl group exhibited 6% NOE with the $C_3$ α-proton and 5% NOE with the $C_4$-proton. The α- and β-protons of $C_3$ were assigned by 2 D-NMR. $[\alpha]_D^{23}$ −19.3 (c 0.5, $CHCl_3$); $^1H$-NMR (300 MHZ, $CDCl_3$) δ 4.43 (t, 1H, J=6.3 Hz), 4.33 (d, 1H, J=9.6 Hz), 3.78 (m, 1H), 2.62 (m, 1H), 2.35 (m, 1H), 1.86 (m, 1H), 1.63-1.24 (m, 3H), 1.37 (s, 9H), 1.21 (d, 3H, J=7.5 Hz), 0.87 (dd, 6H, J=2.6, 6.7 Hz); $^{13}C$-NMR (75 MHZ, $CDCl_3$) δ 180.4, 156.0, 80.3, 79.8, 51.6, 41.9, 34.3, 32.5, 28.3, 24.7, 23.0, 21.8, 16.6; IR (neat) 2962, 2868, 1764, 1687, 1519, 1272, 1212, 1008 cm$^{-1}$; HRMS: m/z (M+Na)$^+$ calc'd for $C_{15}H_{27}NO_4Na$, 308.1838, found 308.1828.

Example 2.6

Synthesis of (2R,4S,5S)-5-[(tert-Butoxycarbonyl) amino]-4-[(tert-butyldimethylsilyl)-oxy]-2,7-methyloctanoic acid

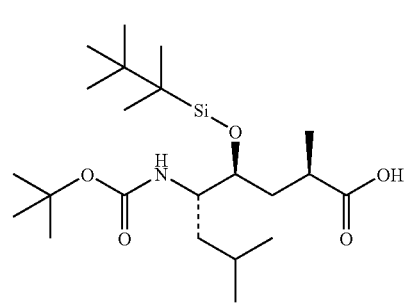

6e

To a stirred solution of lactone 5e (0.33 g, 1.17 mmol) in a mixture of THF and water (5:1; 6 mL) was added LiOH.H$_2$O (0.073 g, 1.8 equiv). The resulting mixture was stirred at room temperature for 1 hour. The volatiles were removed under reduced pressure and the remaining solution was cooled to 0° C. and acidified with 25% aqueous citric acid to pH 3. The resulting acidic solution was extracted with EtOAc three times. The combined organic layers were washed with brine, dried over Na$_2$SO$_4$ and concentrated under reduced pressure to yield the corresponding hydroxy acid (330 mg) as a white foam. This hydroxy acid was used directly for the next reaction without further purification. To the above hydroxy acid (330 mg, 1.1 mmol) in dimethylformamide (DMF) was added imidazole (1.59 g, 23.34 mmol) and tert-butyldimethylchlorosilane (1.76 g, 11.67 mmol). The resulting mixture was stirred at room temperature for 24 hours. MeOH (4 mL) was added and the mixture was stirred for an additional 1 hour. The mixture was acidified with 25% aqueous citric acid to pH 3 and was extracted with EtOAc three times. The combined extracts were washed with water, brine, dried over Na$_2$SO$_4$ and concentrated under reduced pressure. Flash column chromatography (35% EtOAc in hexanes) yielded 6e (0.44 g, 90%). M.p. 121-123° C.; [α]$_D^{23}$ −40.0 (c 0.13, CHCl$_3$); $^1$H-NMR (400 MHZ, DMSO-D, 343 K) δ 6.20 (br s, 1H), 3.68 (m, 1H), 3.51 (br s, 1H), 2.49-2.42 (m, 1H), 1.83 (t, 1H, J=10.1 Hz), 1.56 (m, 1H), 1.37 (s, 9H), 1.28-1.12 (m, 3H), 1.08 (d, 3H, J=7.1 Hz), 0.87 (d, 3H, J=6.1 Hz) 0.86 (s, 9H), 0.82 (d, 3H, J=6.5 Hz), 0.084 (s, 3H), 0.052 (s, 3H); IR (neat) 3300-3000, 2955, 2932, 2859, 1711 cm$^{-1}$; HRMS: m/z (M+Na)$^+$ calc'd for C$_{21}$H$_{43}$NO$_5$NaSi, 440.2808, found 440.2830.

Example 2.7

Synthesis of Leucine-Alanine-Valine Inhibitor Precursor

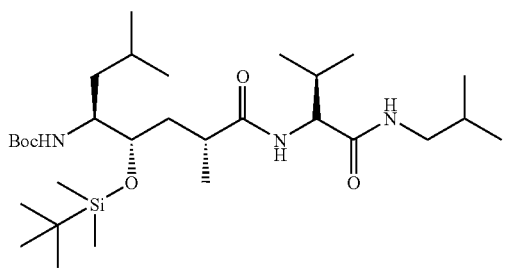

7e

The Leucine-Alanine-Valine Inhibitor Precursor 7e was produced by coupling 6e with Valine-N-iBu amide under standard EDCI/HOBt conditions as follows: to a stirred solution of Leucine-Alanine isostere 6e (0.55 g, 1.3 mmol) in dichloromethane (20 mL) was added HOBt (0.20 g, 1.6 mmol) and EDCI (0.28 g, 1.6 mmol). To this mixture was added a solution of N-Boc-Valine-N'-iBu (0.44 mL, 1.6mmol) which was pretreated with TFA in DCM for 30 minutes and concentrated under reduced pressure, and DIPEA (1.2 mL, 6.7 mmol) in dichloromethane (10 mL).The resulting mixture was stirred at room temperature for 15 h under argon followed by quenching with NaHCO$_3$. The layers were separated and the aqueous layer was extracted with CHCl$_3$ (2×20 mL). The combined organic layer was dried with Na$_2$SO$_4$ and concentrated under reduced pressure. The resulting residue was purified by flash column chromatography (2% methanol in CHCl$_3$) to provide 7e (0.69 g, 75%). $^1$H NMR (300 MHz, CDCl$_3$+CD$_3$OD): δ 4.54 (d, 1H), 4.09 (t, 1H), 3.64-3.80 (m, 2H), 2.98-3.20 (m, 2H), 2.50-2.63 (m, 1H), 2.06-2.21 (m, 1H), 1.20-1.88 (m, 6H), 1.47 (s, 9H), 1.13 (d, 3H, J=6.3 Hz), 0.85-1.01 (m, 27H), 0.08-0.15 (m, 6H).

Example 2.8

Synthesis of Methyl Cysteine Benzyl Ester

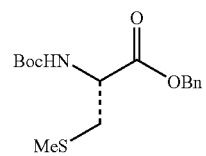

8e

To a stirred solution of N-Boc methyl cysteine (5.0 g, 21 mmol) and benzyl alcohol (2.2 mL, 21 mmol) in CH$_2$Cl$_2$ (50 mL) was added DCC (4.4 g, 21 mmol) and DMAP (2.6 g mL, 21 mmol). The resulting mixture was stirred at room temperature for 15 h and filtered. The filtrate was diluted with saturated aqueous NH$_4$Cl. The layers were separated and the aqueous layer was extracted with CH$_2$Cl$_2$ (2×20 mL). The combined organic layer was washed with brine, dried with Na$_2$SO$_4$ and concentrated under reduced pressure. The resulting oil was purified by column chromatography (3% EtOAC in hexanes) to provide 8e (6.8 g, 98%) as a colorless oil; $^1$H NMR (300 MHz, CDCl$_3$): δ 7.37-7.42 (m, 5H), 5.42 (d, 1H), 5.18-5.28 (m, 2H), 4.59-4.64 (m, 1H), 2.99 (s, 2H), 2.10 (s, 3H), 1.32 (s, 9H).

Example 2.9

Synthesis of Heterocycle Methyl Cysteine Benzyl Ester

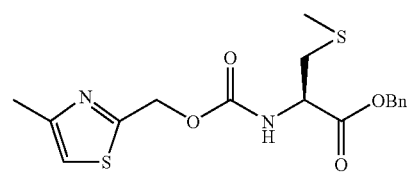

9e

To a stirred solution of triphosgene (205 mg, 0.7 mmol) in CH$_2$Cl$_2$ (10 mL) was added a solution of methyl cysteine benzyl ester 8e (421 mg, 1.9 mmol) in CH$_2$Cl$_2$ (15 mL) slowly via a syringe pump for 1.5 h. To the resulting mixture was added a solution of thiazole methanol (225 mg, 1.8 mmol) and N,N-diisopropylethylamine (0.39 mL, 2.2 mmol) in CH$_2$Cl$_2$ (5 mL). The resulting mixture was stirred at room temperature for 15 h and was quenched with saturatedaqueous NH$_4$Cl. The layers were separated and the aqueous layer was extracted with CH$_2$Cl$_2$ (2×20 mL). The combined organic layer was washed with brine, dried with Na$_2$SO$_4$ and concentrated under reduced pressure. The resulting oil waspurified by column chromatography (30% EtOAc in hexanes) to provide 9e (401 mg, 76%) as a colorless oil; $^1$H NMR (300 MHz, CDCl$_3$): δ 7.34 (s, 5H), 5.86 (s, 1H), 5.78 (d, 1H), 5.33 (s, 2H), 5.18 (s, 2H), 4.61-4.65 (m, 1H), 2.92-2.97 (m, 2H), 2.42 (s, 3H), 2.03 (s, 3H).

Example 2.10

Synthesis of Heterocycle Methyl Cysteine Acid

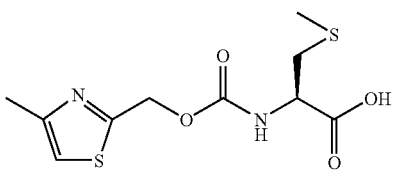

10e

The above ester 9e (13.8 mg, 0.04 mmol) was dissolved in THF (3 mL) and 1N LiOH (1 mL) was added. The resulting mixture was stirred for 30 min and was concentrated under reduced pressure. The solution was acidified to pH 3 by 1N HCl and extracted with EtOAc (2×10 mL). The combined organic layer was washed with brine, dried with Na$_2$SO$_4$ and concentrated under reduced pressure to provide 10e as a yellow oil (8.8 mg, 84% yield).

Example 2.11

Synthesis of Exemplary TBS-Protected Methyl Cysteine Isostere

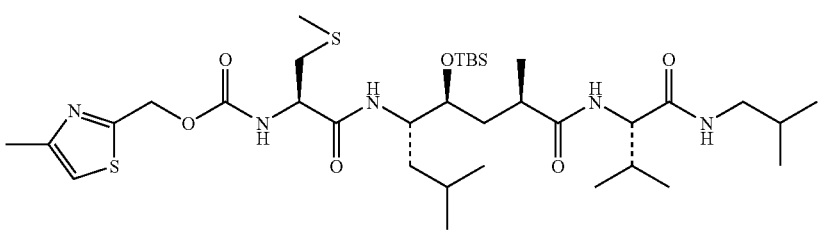

11e

To a stirred solution of acid 1e (24 mg, 0.08 mmol) in CH$_2$Cl$_2$ (3 mL) was added HOBt (12.5 mg 0.09 mmol) and EDCI (17.6 mg, 0.09 mmol). To the resulting mixture was added a solution of 7e (39 mg, 0.08 mmol) (pretreated with TFA in DCM and dried under reduced pressure, DIPEA (0.05 mL, 0.29 mmol), and dichloromethane (2 mL)) and N,N-diisopropylethylamine (73 µL, 0.42 mmol) in CH$_2$Cl$_2$ (2 mL). The resulting mixture was stirred at room temperature for 15 h and quenched with water. The layers were separated and the aqueous layer was extracted with CH$_2$Cl$_2$ (2×10 mL). The combined organic layer was washed with brine, dried with Na$_2$SO$_4$ and concentrated under reduced pressure. The resulting oil was purified by column chromatography (4% MeOH/CHCl$_3$) to provide the product (29 mg, 80%) as a colorless oil; $^1$H NMR (300 MHz, CDCl$_3$): δ 6.91 (s, 1H), 6.68 (d, 1H), 6.56 (d, 1H), 6.25 (m, 1H), 6.17 (d, 1H), 5.29-5.42 (m, 2H), 4.32-4.38 (m, 1H), 4.12-4.19 (m, 2H), 3.67-3.72 (m, 1H), 3.10-3.19 (m, 1H), 2.82-3.05 (m, 3H), 2.51-2.60 (m, 1H), 2.47 (s, 3H), 2.20 (s, 3H), 2.05-2.16 (m, 1H), 1.71-1.85 (m, 2H), 1.56-1.62 (m, 1H), 1.44-1.56 (m, 2H), 1.27-1.36 (m, 1H), 1.12 (d, 3H), 0.84-0.97 (m, 27H), 0.08-0.10 (m, 6H).

Example 2.12

Synthesis of Exemplary Sulfoxide Isostere

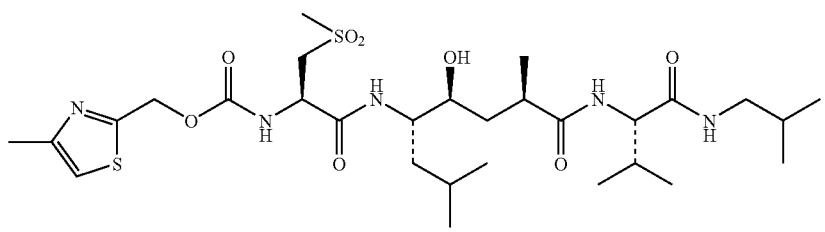

12e

To a stirred solution of 11e (12.3 mg, 0.02 mmol) in CH$_2$Cl$_2$ (2 mL) cooled at 0° C. was added mCPBA (7.6 mg, 0.04 mmol). The resulting mixture was stirred at 0° C. for 1 h and was quenched with saturated aqueous NaHCO$_3$. The layers were separated and the aqueous layer was extracted with CH$_2$Cl$_2$ (2×10 mL). The combined organic layer was washed with brine, dried with Na$_2$SO$_4$ and concentrated under reduced pressure. The crude oil was dissolved in THF (3 mL) and aqueous HF (48%, 15 drops) was added. The mixture was stirred for 30 min and was quenched with saturated aqueous NaHCO$_3$. The layers were separated and the aqueous layer was extracted with EtOAc (2×10 mL). The combined organic layer was washed with brine, dried with Na$_2$SO$_4$ and concentrated under reduced pressure. The resulting solid was purified by column chromatography (5% MeOH/CHCl$_3$) to provide the product (5.1 mg, 49%) as a solid; $^1$H NMR (300 MHz, CDCl$_3$): δ 6.93 (s, 1H), 5.35 (s, 2H), 4.71-4.73 (m, 1H), 4.02 (d, 1H), 3.84-3.92 (m, 1H), 3.62 (d, 2H), 3.48-3.52 (m, 1H), 2.94-3.14 (m, 2H), 3.04 (s, 3H), 2.57-2.63 (m, 1H), 2.45 (s, 3H), 1.98-2.05 (m, 1H), 1.65-1.81 (m, 2H), 1.42-1.56 (m, 3H), 1.25-1.36 (m, 1H), 1.11 (d, 3H), 0.86-0.93 (m, 18H).

Example 3
Physical Properties of Exemplary Compounds
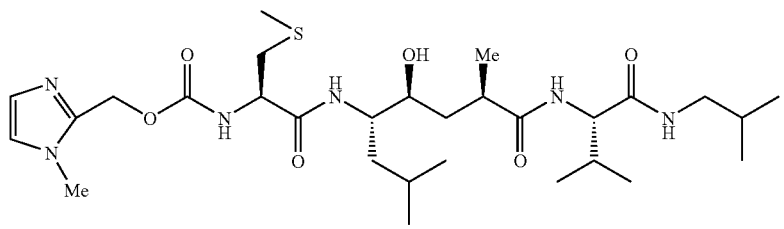
20    $^1$H-NMR: (300 MHz, CDCl$_3$), δ: 6.84 (d, 2H); 5.05 (m, 2H); 4.18 (m, 1H); 3.92 (d, 1H); 3.75 (m, 1H); 3.62 (s, 3H); 3.31 (m, 1H); 2.99 (m, 1H), 2.99 (m, 1H); 2.89 (m, 1H); 2.62-2.86 (m, 2H); 2.55 (m, 1H); 2.09 (s, 3H); 1.94 (m, 1H); 1.52-1.72 (m, 2H); 1.43 (m, 3H); 1.22 (m, 1H); 1.01 (d, 3H); 0.81 (m, 18H). m.p.
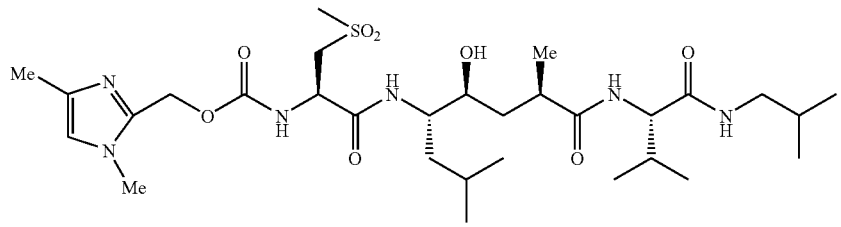
40    $^1$H-NMR: (300 MHz, CDCl$_3$), δ: 6.56 (s, 1H); 5.05 (m, 2H); 4.64 (m, 1H); 3.97 (m, 1H); 3.67 (m, 1H); 3.66 (m, 2H); 3.56 (s, 3H); 3.48 (m, 1H); 2.96 (m, 5H), 2.50 (m, 1H); 2.10 (s, 3H); 1.95 (m, 1H); 1.58-1.78 (m, 2H); 1.32-1.49 (m, 3H); 1.26 (m, 1H); 1.06 (d, 3H); 0.84 (m, 18H). m.p.
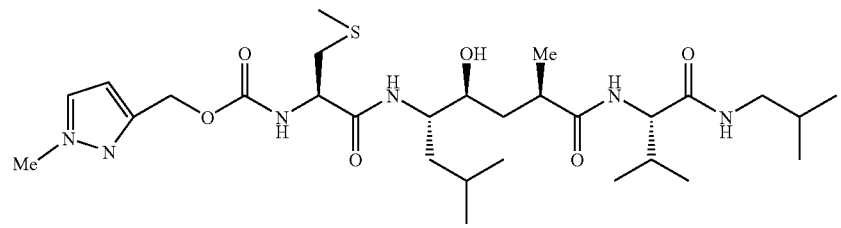

¹H-NMR: (300 MHz, CDCl₃), δ: 7.31 (m, 1H); 6.26 (m, 1H); 5.08 (m, 2H); 4.29 (m, 1H); 4.01 (m, 1H); 3.87 (m, 4H); 3.48 (m, 1H); 3.08 (m, 1H); 2.94 (m, 3H), 2.59 (m, 1H); 2.12 (s, 3H); 2.01 (m, 1H); 1.58-1.78 (m, 2H); 1.32-1.49 (m, 3H); 1.26 (m, 1H); 1.10 (d, 3H); 0.88 (m, 18H). m.p.
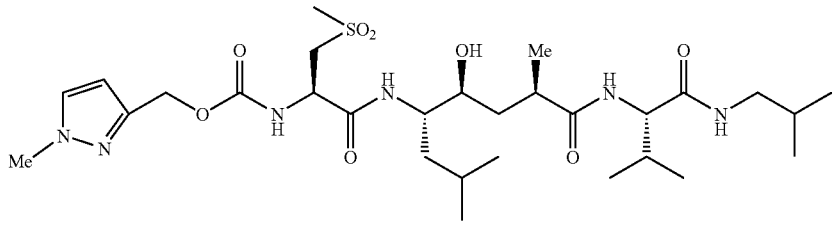
¹H-NMR: (300 MHz, CDCl₃), δ: 7.30 (m, 1H); 6.23 (m, 1H); 5.06 (br, 2H); 4.64 (m, 1H); 3.97 (m, 1H); 3.83 (m, 4H); 3.41 (m, 1H); 3.03 (m, 5H); 2.58 (m, 1H); 1.98 (m, 1H); 1.58-1.78 (m, 2H); 1.32-1.49 (m, 3H); 1.26 (m, 1H); 1.07 (d, 3H); 0.84 (m, 18H). m.p.
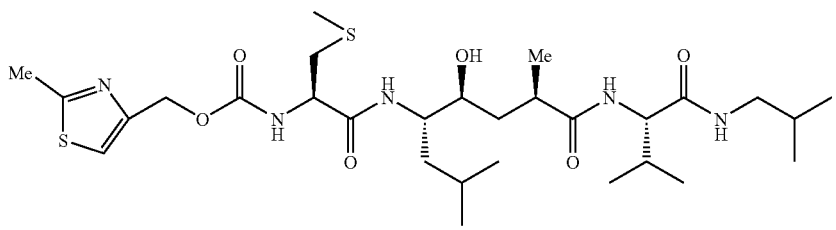
¹H-NMR: (300 MHz, CDCl₃), δ: 7.18 (s, 1H); 5.17 (m, 2H); 4.33 (m, 1H); 4.01 (m, 1H); 3.83 (m, 1H); 3.52 (m, 1H); 3.11 (m, 1H); 3.01 (m, 1H); 2.87 (m, 2H); 2.75 (m, 3H); 2.61 (m, 1H); 2.08 (m, 4H); 1.61-1.81 (m, 2H); 1.40-1.60 (m, 3H); 1.29 (m, 1H); 1.14 (d, 3H); 0.92 (m, 18H). m.p.
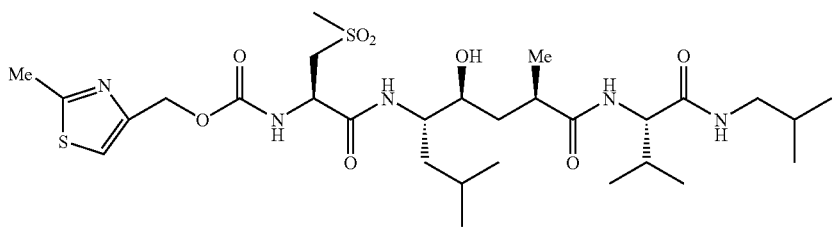
¹H-NMR: (300 MHz, CDCl₃), δ: 7.18 (s, 1H); 5.17 (m, 2H); 4.33 (m, 1H); 4.01 (m, 1H); 3.83 (m, 1H); 3.52 (m, 1H); 3.11 (m, 1H); 3.01 (m, 1H); 2.87 (m, 2H); 2.75 (m, 3H); 2.61 (m, 1H); 2.08 (m, 4H); 1.61-1.81 (m, 2H); 1.40-1.60 (m, 3H); 1.29 (m, 1H); 1.14 (d, 3H); 0.92 (m, 18H). m.p.
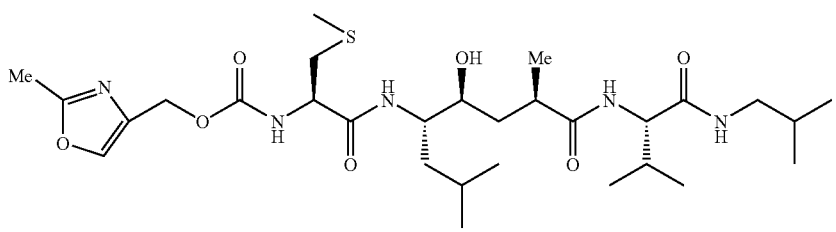

¹H-NMR: (300 MHz, CDCl₃), δ: 7.52 (br, 1H); 5.12 (br, 1H); 4.88 (br, 1H); 4.19 (m, 1H); 3.95 (m, 1H); 3.76 (m, 1H); 3.40 (m, 1H); 2.99 (m, 1H); 2.88 (m, 1H); 2.82-2.64 (m, 2H); 2.51 (m, 1H); 2.35 (m, 3H); 2.08 (m, 3H); 1.91 (m, 1H); 1.91 (m, 1H); 1.53-1.71 (m, 2H); 1.42 (m, 3H); 1.21 (m, 1H); 1.04 (d, 3H); 0.80 (m, 18H). m.p.
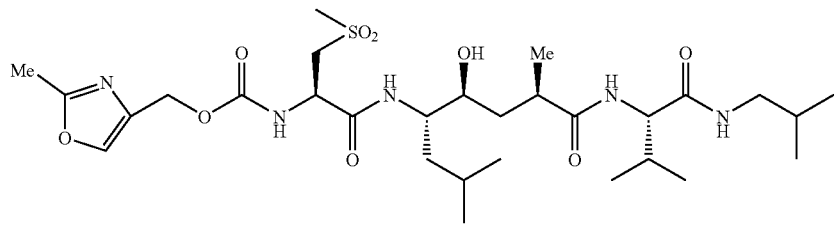
¹H-NMR: (300 MHz, CDCl₃), δ: 7.52 (br, 1H); 4.89 (m, 2H); 4.58 (m, 1H); 3.93 (m, 1H); 3.75 (m, 1H); 3.51-3.59 (m, 1H); 3.31-3.44 (m, 2H); 3.02-2.82 (m, 5H); 2.51 (m, 1H); 2.34 (m, 3H); 1.89 (m, 1H); 1.54-1.71 (m, 2H); 1.32 (m, 3H); 1.20 (m, 1H); 1.02 (d, 3H); 0.79 (m, 18H). m.p.
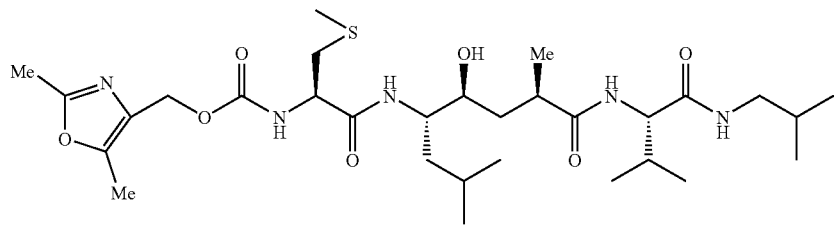
¹H-NMR: (300 MHz, CDCl₃), δ: 7.07 (br, 1H); 4.87 (m, 2H); 4.24 (m, 1H); 3.99 (m, 1H); 3.81 (m, 1H); 3.44 (m, 1H); 3.02 (m, 1H); 2.93 (m, 1H); 2.79 (m, 2H); 2.57 (m, 1H); 2.36 (s, 3H); 2.26 (s, 3H); 2.08 (s, 3H); 1.99 (m, 1H); 1.59-1.76 (m, 2H); 1.48 (m, 3H); 1.26 (m, 1H); 1.08 (d, 3H); 0.87 (m, 18H). m.p.
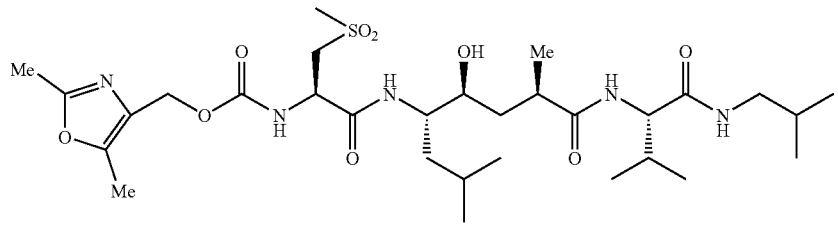
¹H-NMR: (300 MHz, CDCl₃), δ: 7.21 (br, 1H); 4.82 (s, 2H); 4.58 (m, 1H); 3.76 (m, 1H); 3.31-3.48 (m, 2H); 2.89 (m, 5H); 2.52 (m, 1H); 2.30 (s, 3H); 2.22 (s, 3H); 1.91 (m, 1H); 1.54-1.71 (m, 2H); 1.37 (m, 3H); 1.20 (m, 1H); 1.02 (d, 3H); 0.81 (m, 18H). m.p.
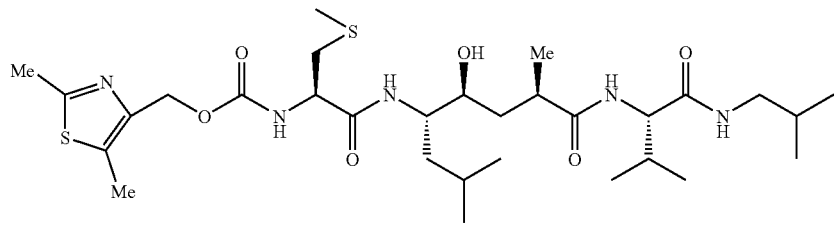

¹H-NMR: (300 MHz, CDCl₃), δ: 7.12 (br, 1H); 5.08 (m, 2H); 4.30 (m, 1H); 4.01 (m, 1H); 3.86 (m, 1H); 3.51 (m, 1H); 3.11 (m, 1H); 2.98 (m, 1H); 2.85 (m, 2H); 2.64 (s, 3H); 2.43 (s, 3H); 2.13 (m, 4H); 1.59-1.81 (m, 2H); 1.53 (m, 3H); 1.26 (m, 1H); 1.14 (d, 3H); 0.87 (m, 18H). m.p.
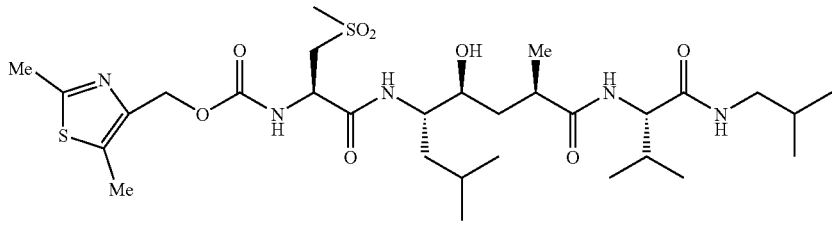
¹H-NMR: (300 MHz, CDCl₃), δ: 7.27 (br, 1H); 7.21 (br, 1H); 5.00 (s, 2H); 4.61 (m, 1H); 3.94 (m, 1H); 3.79 (m, 1H); 3.34-3.62 (m, 3H); 2.94 (m, 5H); 2.54 (s, 4H); 2.36 (s, 3H); 1.92 (m, 1H); 1.58-1.71 (m, 2H); 1.37 (m, 3H); 1.24 (m, 1H); 1.05 (d, 3H); 0.84 (m, 18H). m.p.
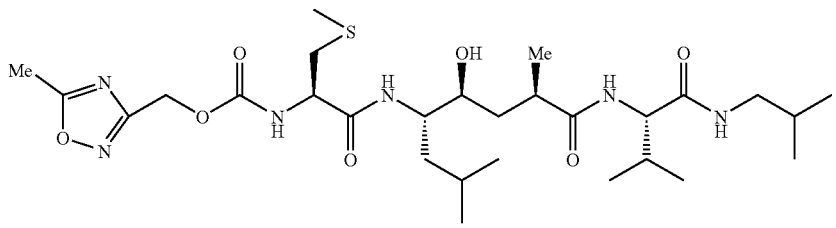
¹H-NMR: (300 MHz, CDCl₃), δ: 5.15 (br, 2H); 4.27 (m, 1H); 3.98 (m, 1H); 3.80 (m, 1H); 3.04 (m, 1H); 2.98-2.75 (m, 3H); 2.57 (m, 4H); 2.09 (s, 3H); 1.97 (m, 1H); 1.59-1.81 (m, 2H); 1.53 (m, 3H); 1.26 (m, 1H); 1.08 (d, 3H); 0.86 (m, 18H). m.p.
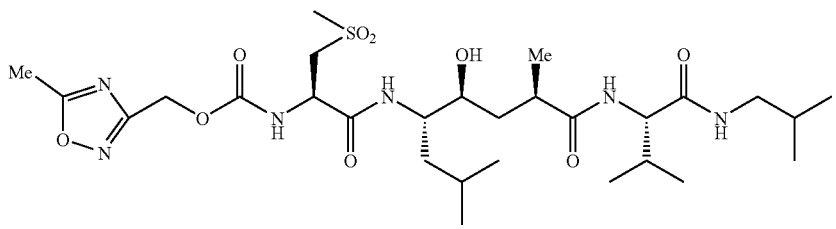
¹H-NMR: (300 MHz, CDCl₃), δ: 5.19 (s, 2H); 4.68 (m, 1H); 3.98 (m, 1H); 3.85 (m, 1H); 3.60 (m, 2H); 3.44 (m, 1H); 3.02 (m, 5H); 2.51 (d, 4H); 1.96 (m, 1H); 1.61-1.78 (m, 2H); 1.45 (m, 3H); 1.31 (m, 1H); 1.09 (d, 3H); 0.87 (m, 18H). m.p.
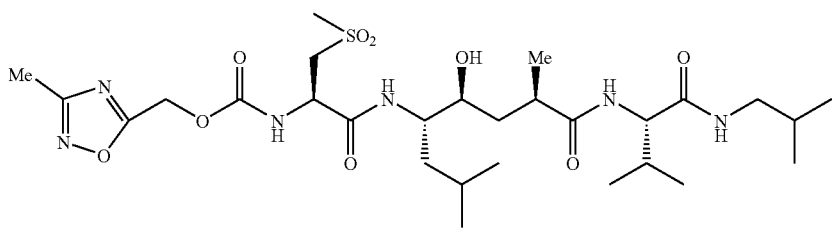

¹H-NMR: (300 MHz, CDCl₃), δ: 5.20 (s, 2H); 4.58 (m, 1H); 3.95 (m, 1H); 3.78 (m, 1H); 3.58 (m, 2H); 2.94 (m, 5H); 2.48 (m, 1H); 2.31 (s, 3H); 1.87 (m, 1H); 1.53-1.78 (m, 2H); 1.38 (m, 3H); 1.27 (m, 1H); 1.01 (d, 3H); 0.81 (m, 18H). m.p.
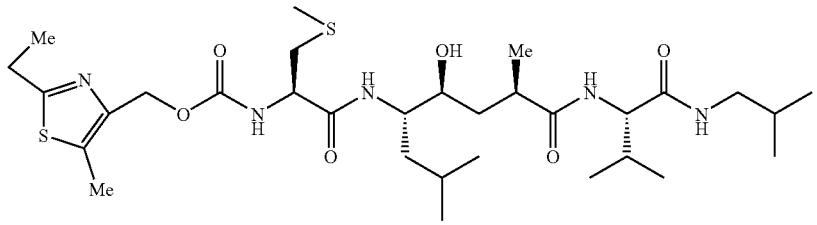
¹H-NMR: (300 MHz, CDCl₃), δ: 7.12 (br, 1H); 5.04 (m, 2H); 4.26 (m, 1H); 3.99 (m, 1H); 3.81 (m, 1H); 3.41 (m, 6H); 3.03 (m, 1H); 2.93 (m, 2H); 2.80 (m, 1H); 2.61 (m, 1H); 2.41 (s, 3H); 2.08 (s, 3H); 1.98 (m, 1H); 1.59-1.78 (m, 2H); 1.48 (m, 3H); 1.27 (m, 4H); 1.08 (d, 3H); 0.87 (m, 18H). m.p.
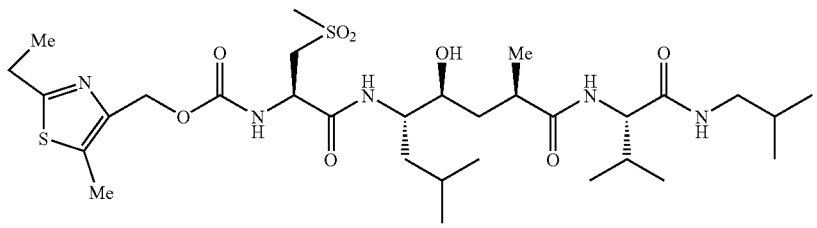
¹H-NMR: (300 MHz, CDCl₃), δ: 7.27 (br, 1H); 5.06 (s, 2H); 4.65 (m, 1H); 3.98 (m, 1H); 3.82 (m, 1H); 3.61 (m, 3H); 3.21-2.88 (m, 7H); 2.58 (m, 2H); 2.42 (s, 3H); 1.97 (m, 1H); 1.61-1.78 (m, 2H); 1.41 (m, 3H); 1.33 (m, 4H); 1.09 (d, 3H); 0.88 (m, 18H). M.p.
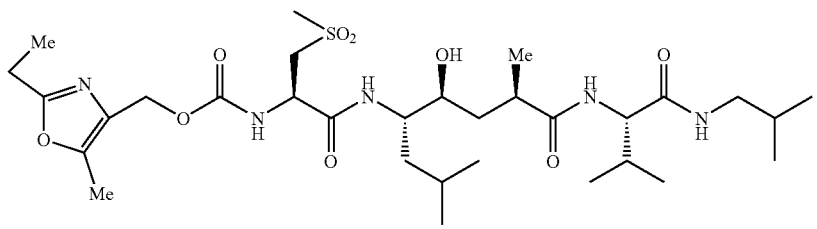
¹H-NMR: (300 MHz, CDCl₃), δ: 7.21 (br, 1H); 4.85 (s, 2H); 4.61 (m, 1H); 3.98 (m, 1H); 3.38-3.62 (m, 3H); 2.95 (m, 4H); 2.64 (m, 2H); 2.58 (m, 1H); 2.24 (s, 3H); 1.97 (m, 1H); 1.61-1.78 (m, 2H); 1.41 (m, 3H); 1.19 (m, 4H); 1.05 (d, 3H); 0.84 (m, 18H). m.p.
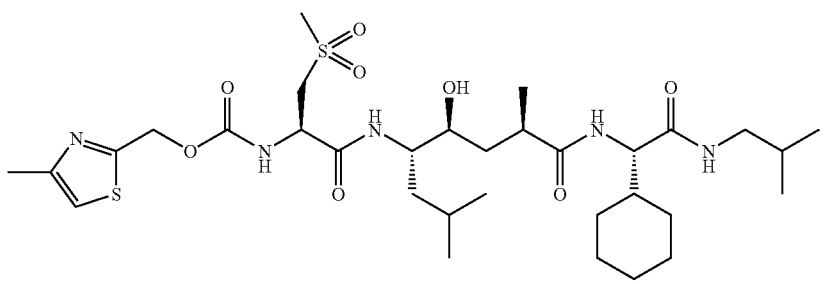

The above compound was synthesized through sequential EDCI/HOBt coupling of isobutylamine with N-Boc-cyclohexylalanine, N-Boc-isostere, and N-[O-(4-methyl-thiazol-2-yl-methyl)]carbamoyl-methylcysteine followed by oxidation with m-CPBA and deprotection of the silyl ether with HF$_{(aq)}$.

¹H-NMR (300 MHz, CDCl₃+CD₃OD): δ 6.95 (s, 1H), 5.44-5.30 (m, 2H), 4.79-4.70 (m, 1H), 4.10-4.00 (m, 1H), 3.93-3.81 (m, 1H), 3.71-3.59 (m, 2H), 3.56-3.46 (m, 1H), 3.46-3.40 (m, 1H), 3.15-2.93 (m, 1H), 3.06 (s, 3H), 2.66-2.54 (m, 1H), 2.45 (s, 3H), 2.36-2.10 (m, 2H), 1.83-1.16 (m, 15H), 1.12 (d, 3H), 0.95-0.80 (m, 12H).

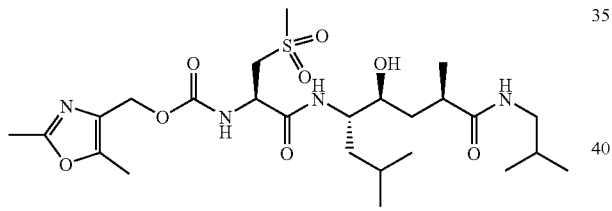

The above compound was synthesized through sequential EDCI/HOBt coupling of isobutylamine with N-Boc-isostere, and N-[O-(2,5-dimethyl-oxazol-4-yl-methyl)]carbamoyl-methylcysteine followed by oxidation with m-CPBA and deprotection of the silyl ether with HF$_{(aq)}$.

¹H-NMR (300 MHz, CDCl₃+CD₃OD): δ 4.98-84 (m, 2H), 4.70-4.61 (m, 1H), 3.90-3.79 (m, 1H), 3.77-3.42 (m, 3H), 3.00 (s, 3H), 3.09-2.93 (m, 3H), 2.56-2.44 (m, 1H), 2.40 (s, 3H), 2.30 (s, 3H), 1.81-1.26 (m, 5H), 1.13 (d, 3H), 0.92-0.83 (m, 12H).

The above compound was synthesized through sequential EDCI/HOBt coupling of 4-aminomethylpyridine with N-Boc-valine, N-Boc-isostere, and N-[O-(4-methyl-thiazol-2-yl-methyl)]carbamoyl-methylcysteine followed by oxidation with m-CPBA and deprotection of the silyl ether with HF$_{(aq)}$.

¹H-NMR (300 MHz, CDCl₃): δ 8.50-8.42 (m, 2H), 8.14-8.06 (m, 1H), 7.34-7.22 (m, 4H), 6.91 (s, 1H), 5.35-5.27 (m 2H), 4.70-4.63 (m, 1H), 4.44-4.37 (m, 2H), 4.10-4.02 (m, 1H), 3.90-3.78 (m, 1H), 3.69-3.40 (m, 3H), 3.00 (s, 3H), 2.66-2.53 (m, 1H), 2.41 (s, 3H), 2.09-1.95 (m, 1H), 1.75-1.62 (m, 1H), 1.58-1.35 (m, 3H), 1.34-1.20 (m, 2H), 1.10 (d, 3H), 0.91 (d, 6H), 0.89-0.81 (m, 6H).

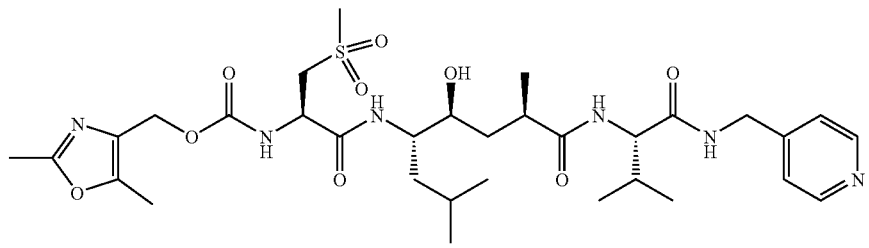

The above compound was synthesized through sequential EDCI/HOBt coupling of 4-aminomethylpyridine with N-Boc-valine, N-Boc-isostere, and N-[O-(2,5-dimethyl-oxazol-4-yl-methyl)]carbamoyl-methylcysteine followed by oxidation with m-CPBA and deprotection of the silyl ether with HF$_{(aq)}$.

¹H-NMR (300 MHz, CDCl₃+CD₃OD): δ 8.52-8.32 (m, 2H), 7.25-7.12 (m, 2H), 4.95-4.80 (m, 2H), 4.70-4.59 (m, 2H), 4.48-4.30 (m, 2H), 4.07 (d, 1H), 3.90-3.75 (m, 1H), 3.65-3.32 (m, 3H), 3.00 (s, 3H), 2.66-2.54 (m, 1H), 2.40 (s, 3H), 2.29 (s, 3H), 2.50-1.95 (m, 1H), 1.74-1.15 (m, 4H), 1.11 (d, 3H), 0.96-0.79 (m, 12H); amorphous solid, MP=205-207° C. (decomp).

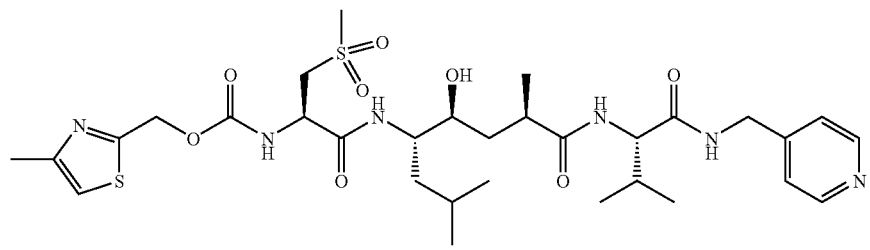

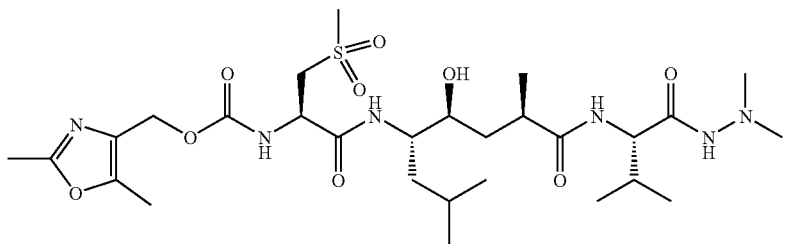

The above compound was synthesized through sequential EDCI/HOBt coupling of N,N-dimethylhydrazine with N-Boc-valine, N-Boc-isostere, and N-[O-(2,5-dimethyl-oxazol-4-yl-methyl)]carbamoyl-methylcysteine followed by oxidation with m-CPBA and deprotection of the silyl ether with $HF_{(aq)}$.

$^1$H-NMR (300 MHz, $CDCl_3$+$CD_3OD$): δ 4.94-4.81 (m, 2H), 4.65-4.58 (m, 1H), 3.90-3.79 (m, 2H), 3.66-3.62 (m, 1H), 3.20-3.02 (m, 8H), 2.80-2.60 (m, 2H), 2.65 (s, 3H), 2.39 (s, 3H), 2.29 (s, 3H), 2.11-1.98 (m, 1H), 1.78-1.18 (m, 4H), 1.11 (d, 3H), 0.98-0.80 (m, 12H).

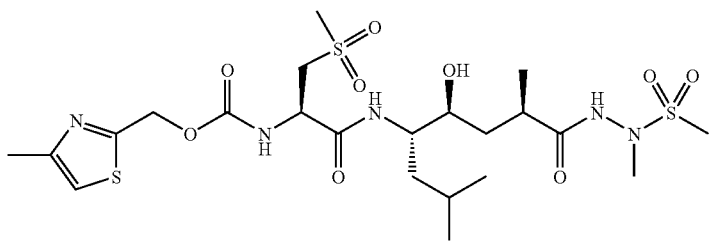

The above compound was synthesized through EDCI/HOBt coupling of methylhydrazine with N-Boc-isostere, followed by reaction with methanesulfonyl chloride, EDCI/HOBt coupling with N-[O-(4-methyl-thiazol-2-yl-methyl)]carbamoyl-methylcysteine, oxidation with m-CPBA and deprotection of the silyl ether with p-toulene sulfonic acid.

$^1$H-NMR (300 MHz, $CDCl_3$+$CD_3OD$): δ 6.95 (s, 1H), 5.45-5.30 (m, 2H), 4.73-4.72 (m, 1H), 4.01-3.89 (m, 1H), 3.75-3.51 (m, 3H), 3.23 (s, 3H), 3.10-2.99 (m, 6H), 2.62-2.50 (m, 1H), 2.46 (s, 3H), 1.77-1.46 (m, 3H), 1.39-1.19 (m, 2H), 1.15 (d, 3H), 0.94-0.85 (m, 6H).

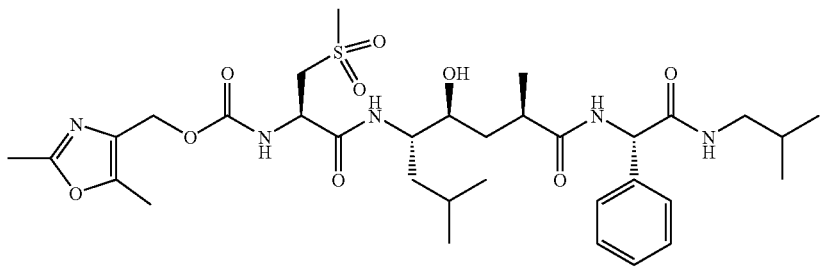

The above compound was synthesized through sequential EDCI/HOBt coupling of isobutylamine with N-Boc-phenylglycine, N-Boc-isostere, and N-[O-(2,5-dimethyl-oxazol-4-yl-methyl)]carbamoyl-methylcysteine followed by oxidation with m-CPBA and deprotection of the silyl ether with HF$_{(aq)}$.

$^1$H-NMR (300 MHz, CDCl$_3$+CD$_3$OD): δ 7.40-7.21 (m, 5H), 5.33 (s, 1H), 5.96-5.80 (m, 2H), 4.63-4.57 (m, 1H), 3.81-3.70 (m, 1H), 3.55-3.23 (m, 4H), 3.09-2.87 (m, 2H), 2.93 (s, 3H), 2.71-2.58 (m, 1H), 2.37 (s, 3H), 2.28 (s, 3H), 1.75-1.52 (m, 2H), 1.47-1.30 (m, 3H), 1.11 (d, 3H), 0.84-0.73 (m, 12H).

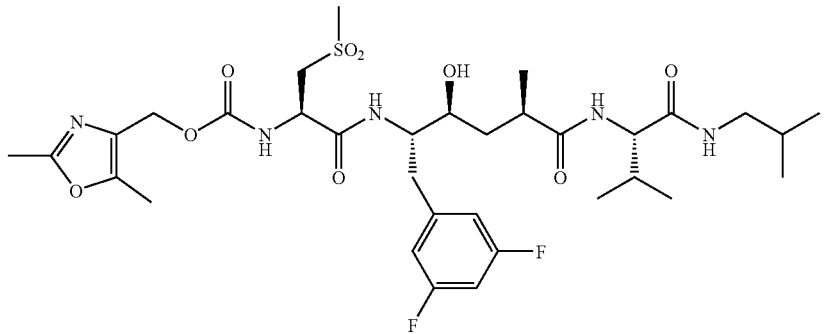

The above compound was synthesized through sequential EDCI/HOBt coupling of isobutylamine with N-Boc-valine, N-Boc-isostere, and N-[O-(2,5-dimethyl-oxazol-4-yl-methyl)]carbamoyl-methylcysteine followed by oxidation with m-CPBA and deprotection of the silyl ether with HF$_{(aq)}$.

$^1$H-NMR (300 MHz, CDCl$_3$+CD$_3$OD): δ 6.76-6.65 (m, 2H), 6.64-6.53 (m, 1H), 4.92-4.83 (m, 2H), 4.64-4.55 (m, 1H), 4.09-3.89 (m, 1H), 3.65-3.33 (m, 3H), 3.09-2.68 (m, 4H), 2.91 (s, 3H), 2.58-2.45 (m, 1H), 2.34 (s, 3H), 2.26 (s, 3H), 2.0-1.25 (m, 5H), 1.02 (d, 3H), 0.90-0.75 (m, 12H).

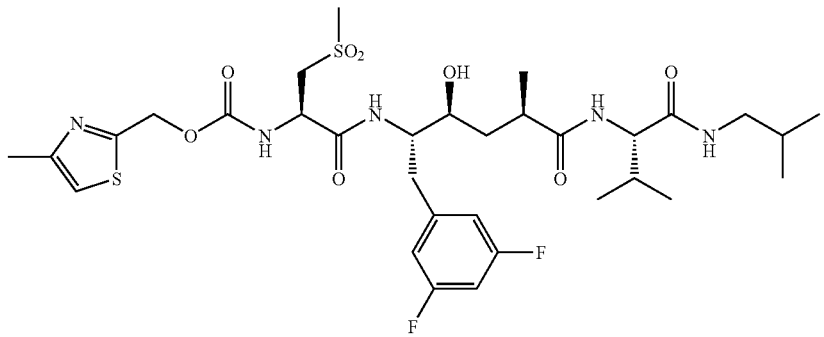

The above compound was synthesized through sequential EDCI/HOBt coupling of isobutylamine with N-Boc-valine, N-Boc-isostere, and N-[O-(4-methyl-thiazol-2-yl-methyl)]carbamoyl-methylcysteine followed by oxidation with m-CPBA and deprotection of the silyl ether with HF$_{(aq)}$.

$^1$H-NMR (300 MHz, CDCl$_3$+CD$_3$OD): δ 6.92 (s, 1H), 6.76 (m, 2H), 6.65-6.55 (m, 1H), 5.38-5.24 (m, 2H), 4.68-4.61 (m, 1H), 4.02-3.92 (m, 2H), 3.62-3.41 (m, 3H), 3.12-2.68 (m, 4H), 2.96 (s, 3H), 2.58-2.48 (m, 1H), 2.42 (s, 3H), 2.05-1.35 (m, 5H), 1.04 (d, 3H), 0.91-0.76 (m, 12H).

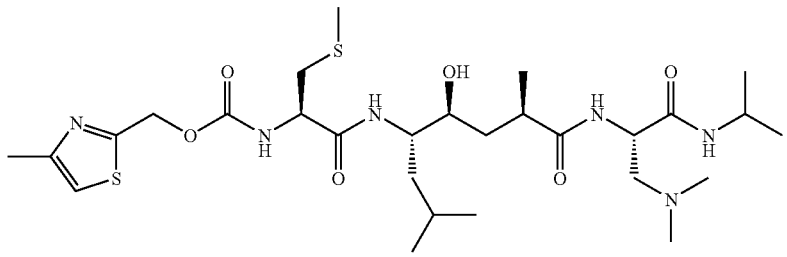

The above compound was synthesized through sequential EDCI/HOBt coupling of isobutylamine with N$^\alpha$-Boc-(S)-2-amino-3-(dimethylamino)propionic acid, N-Boc-isostere, and N-[O-(4-methyl-thiazol-2-yl-methyl)]carbamoyl-methylcysteine followed by deprotection of the silyl ether with HF$_{(aq)}$.

$^1$H-NMR (300 MHz, CDCl$_3$+CD$_3$OD): δ 6.9 (s, 1H), 5.31 (s, 2H), 4.40-4.28 (m, 2H), 3.99-3.89 (m, 1H), 3.88-3.80 (m, 1H), 3.48-3.41 (m, 1H), 2.92-2.39 (m, 5H), 2.41 (s, 3H), 2.28 (s, 6H), 2.13 (s, 3H), 1.61-1.43 (m, 4H), 1.30-1.16 (m, 1H), 1.14-1.06 (m, 9H), 0.89-0.83 (m, 6H).

Example 4

Inhibition of Memapsin 2 Beta-Secretase Activity

Potency of compounds were determined by measurement of their inhibition of memapsin 2 activity toward a fluorescent substrate. Kinetic inhibition experiment were performed using the procedure as described in Ermolieff, et al. (*Biochemistry* 39:12450-12456 (2000), the teachings of which are incorporated hereby in their entirety). Briefly, assays were performed at pH 4, 37° C., by pre-incubation of memapsin 2 enzyme with compound for 20 minutes. Activity measure was initiated by addition of a fluorogenic substrate FS-2 (Bachem Americas, Torrance, Calif.). Fluorescent signal increase over time was measured as a rate of hydrolysis of the peptide substrate. Inhibition of hydrolytic rate was expressed relative to uninhibited controls and fit to a model for tight-binding inhibitors (J. Bieth, in "Proteinase Inhibitors", Bayer Symposium V, 463-469, 1974). The results are presented in Table 1A and Table 1B below.

TABLE 1A

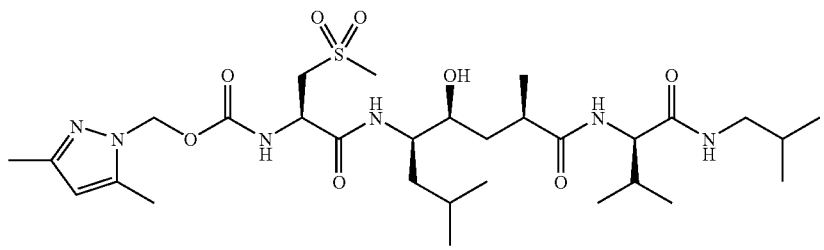

1

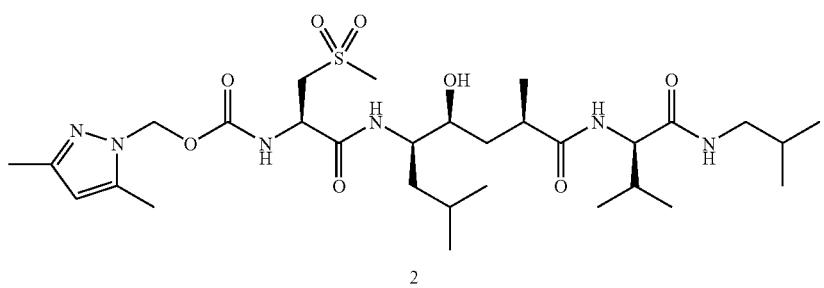

2

TABLE 1A-continued
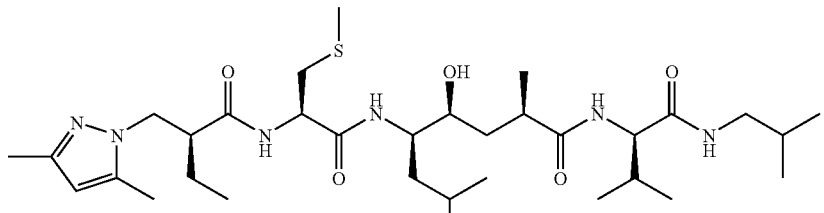
3
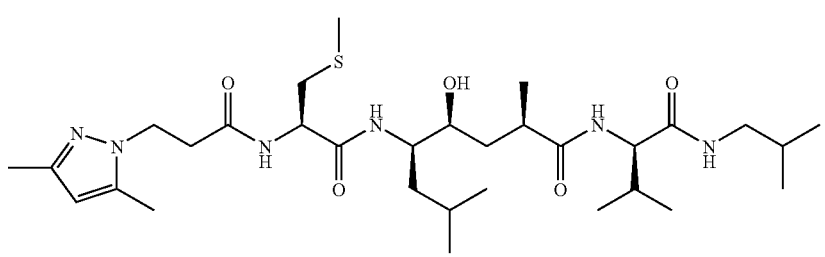
4
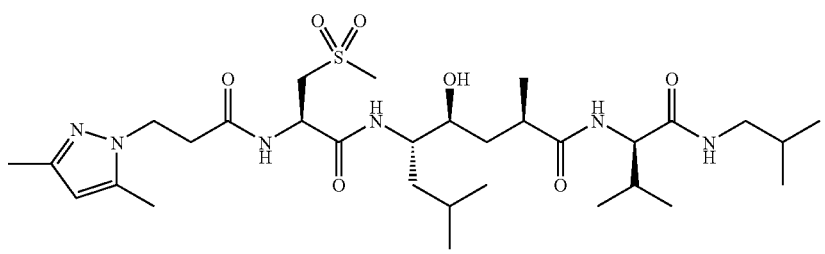
5
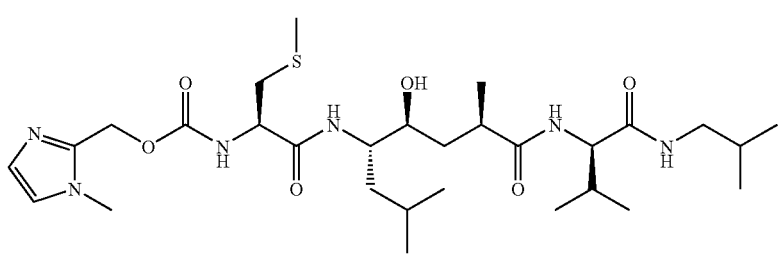
6
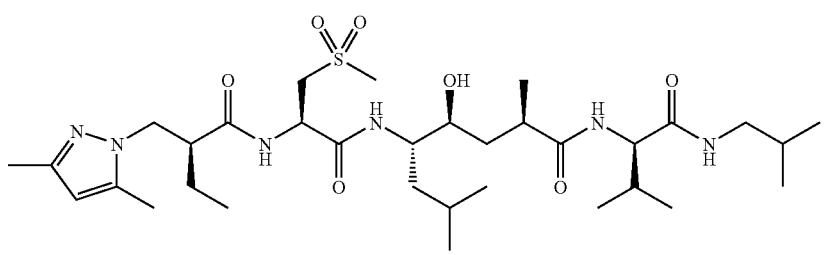
7

TABLE 1A-continued
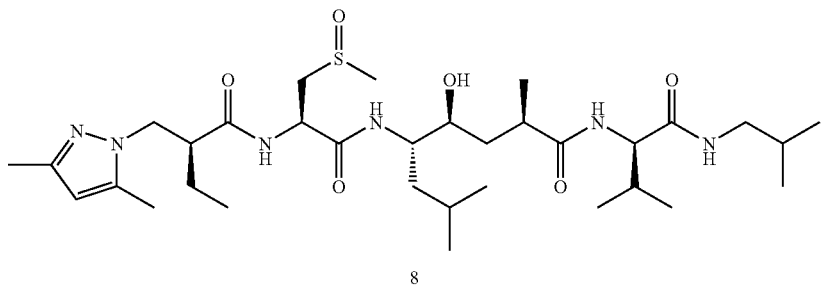
8
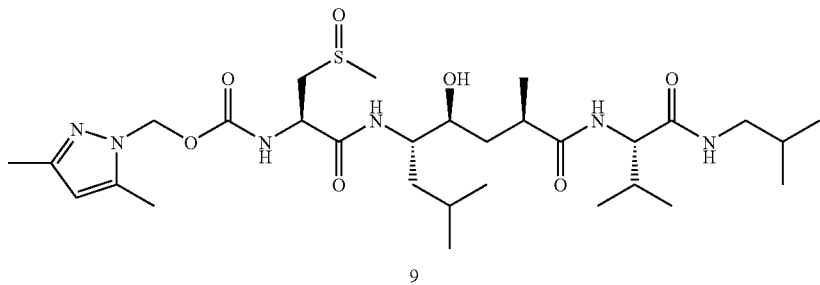
9
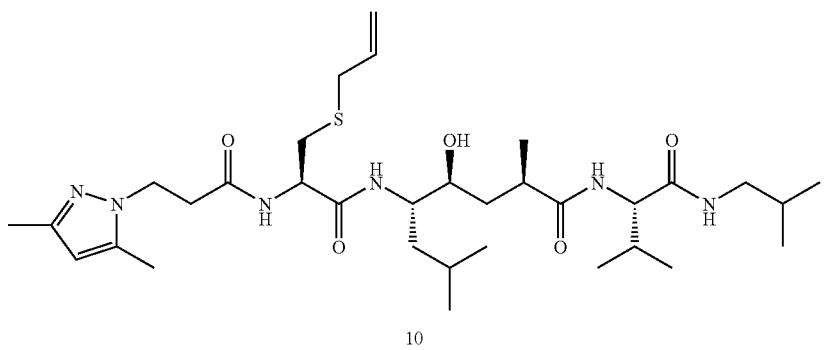
10
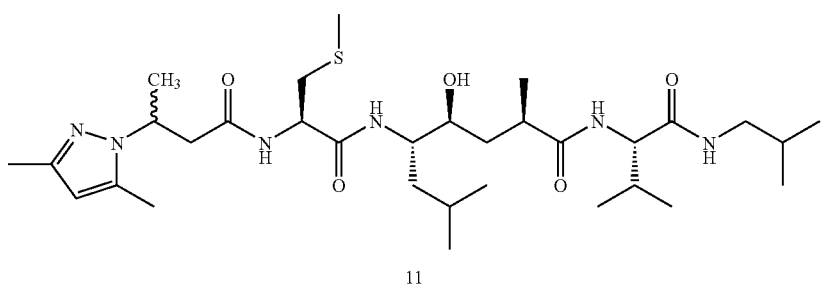
11

TABLE 1A-continued
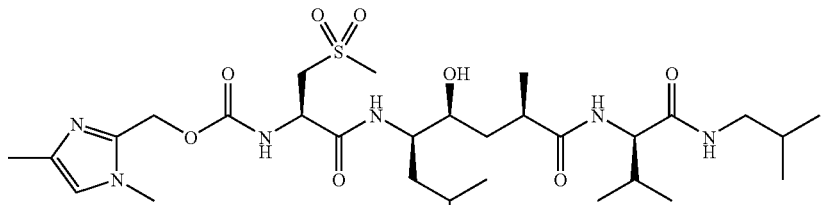
Or
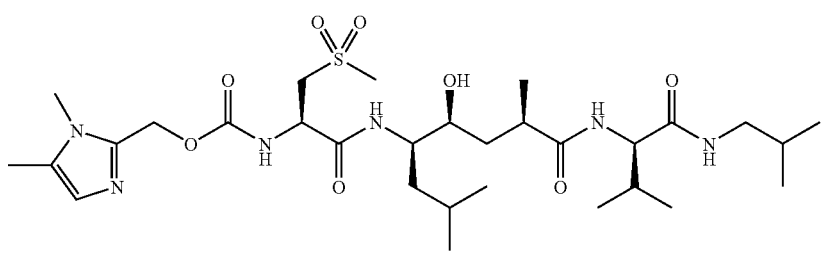
12
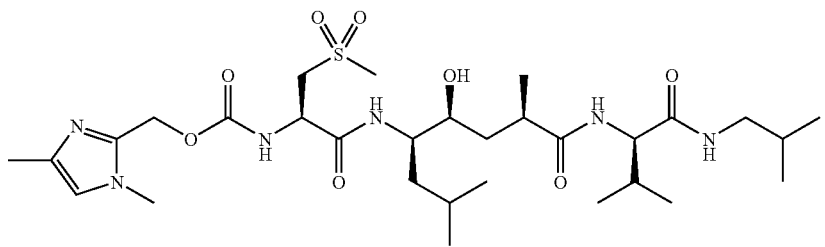
Or
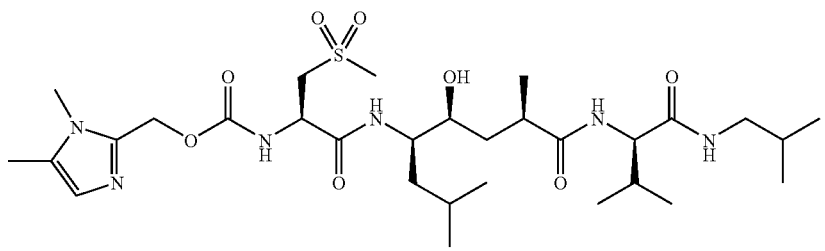
13
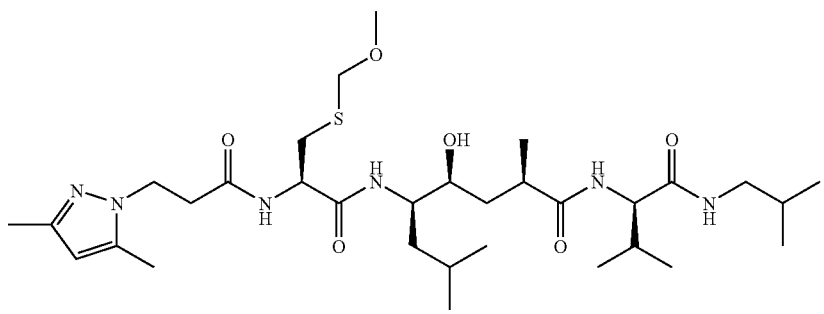
14

TABLE 1A-continued
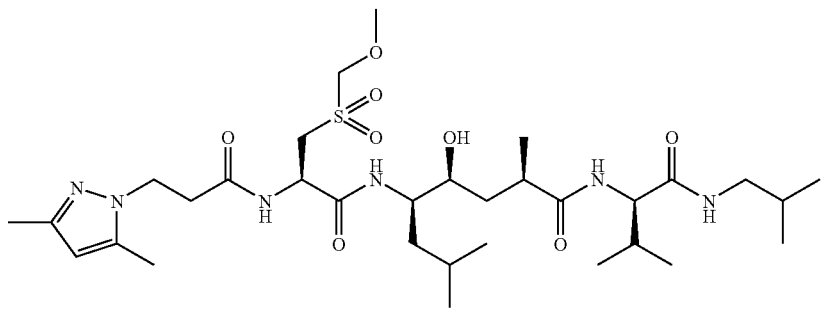
15
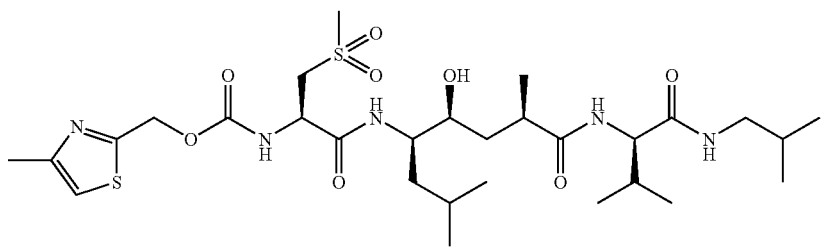
16
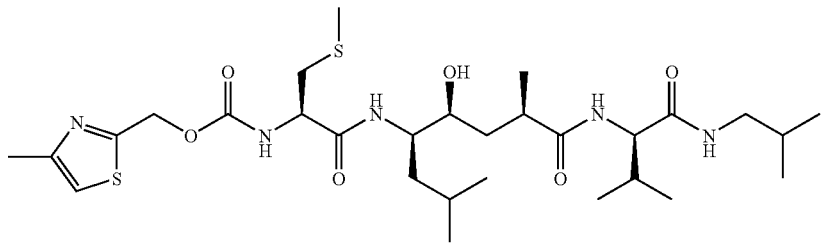
17
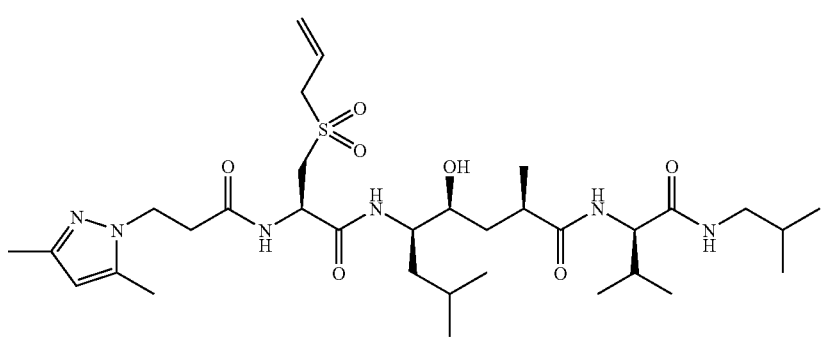
18

TABLE 1A-continued
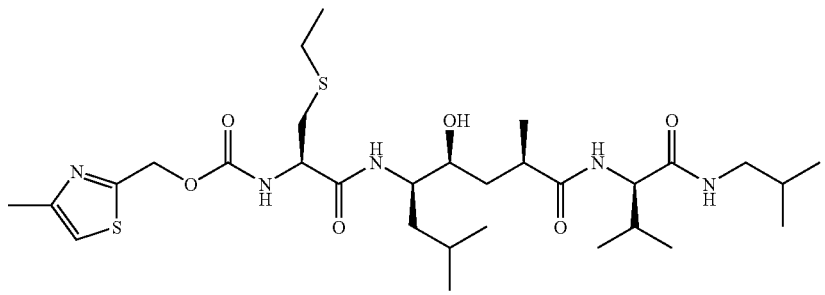
19
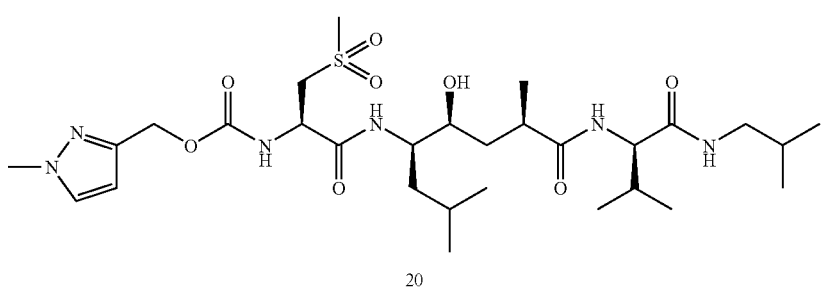
20
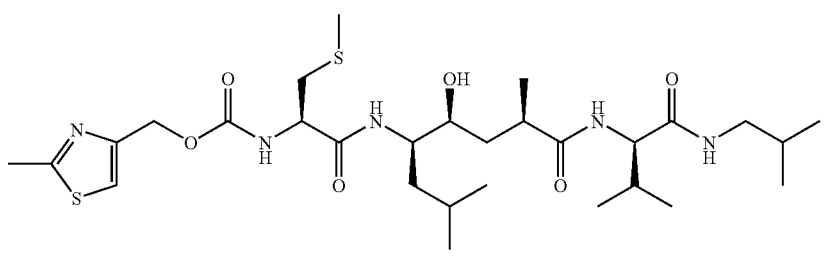
21
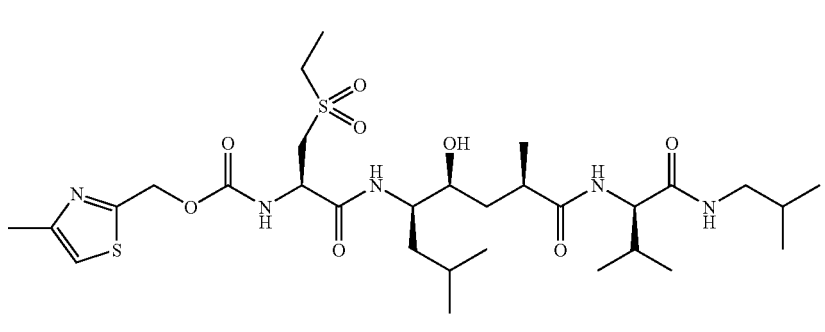
22
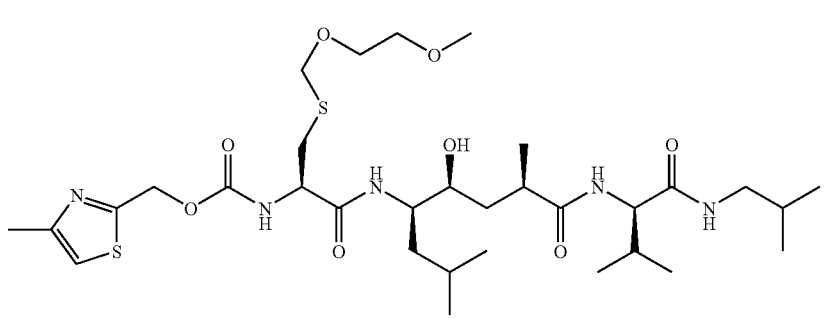
23

TABLE 1A-continued
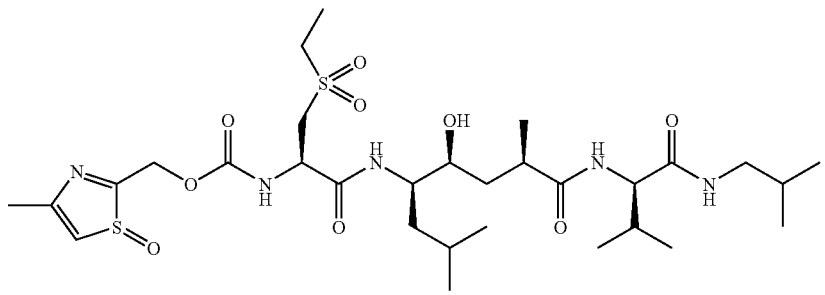
24
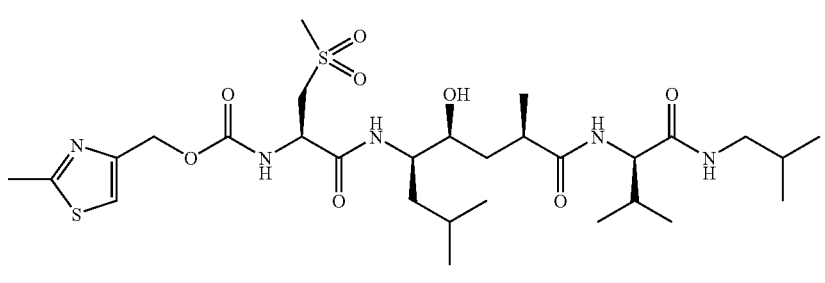
25
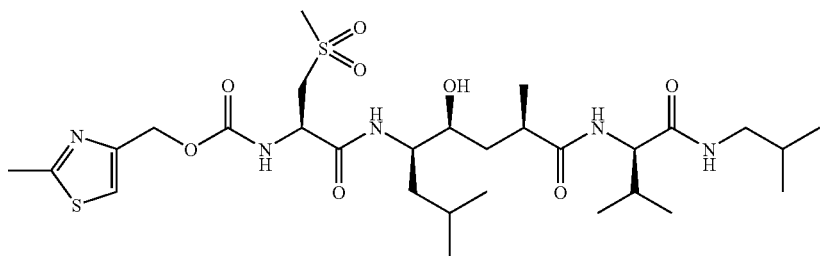
26
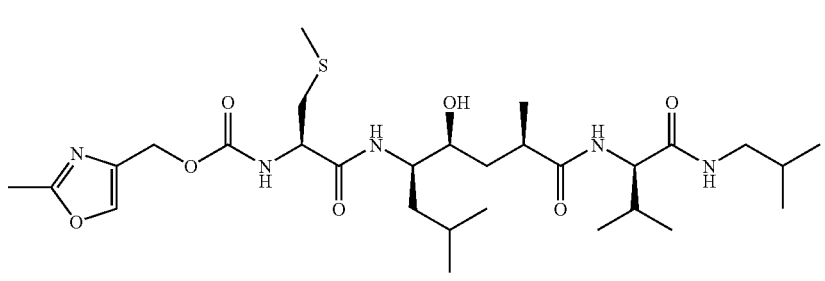
27
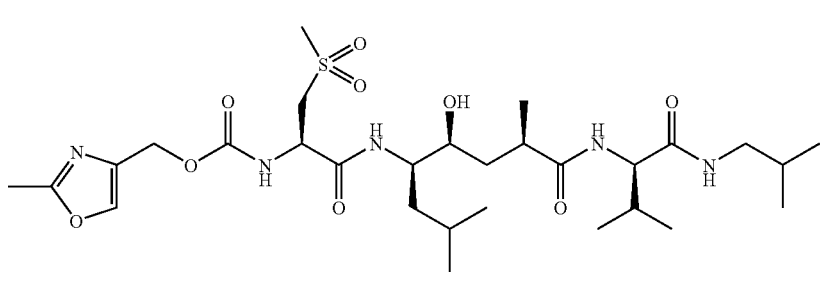
28

TABLE 1A-continued
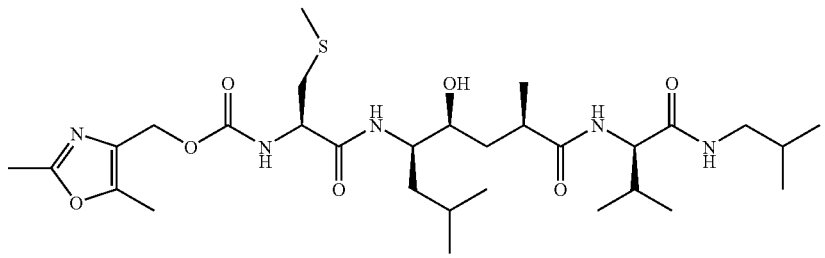
29
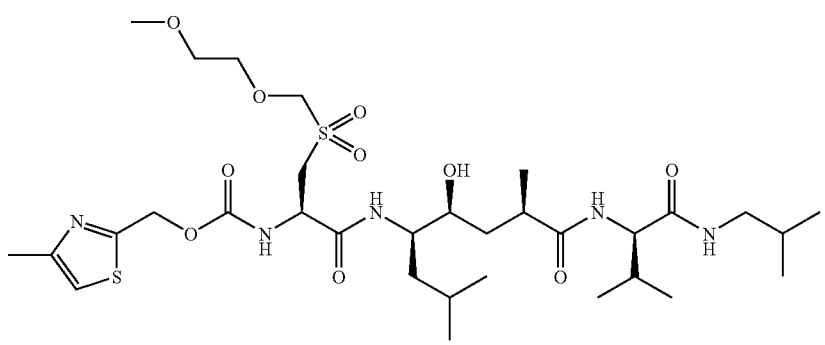
30
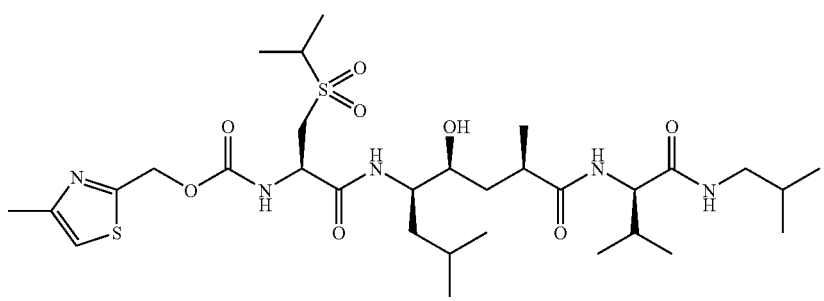
31
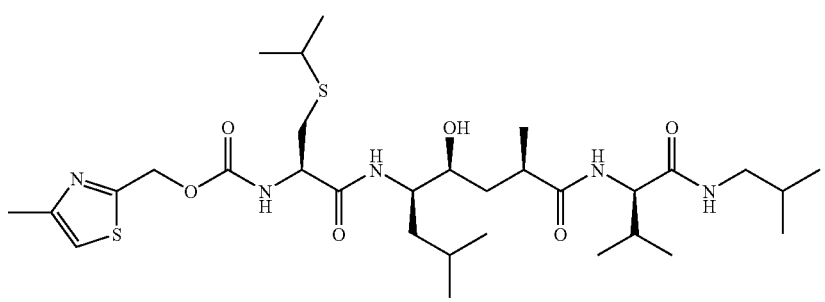
32

TABLE 1A-continued
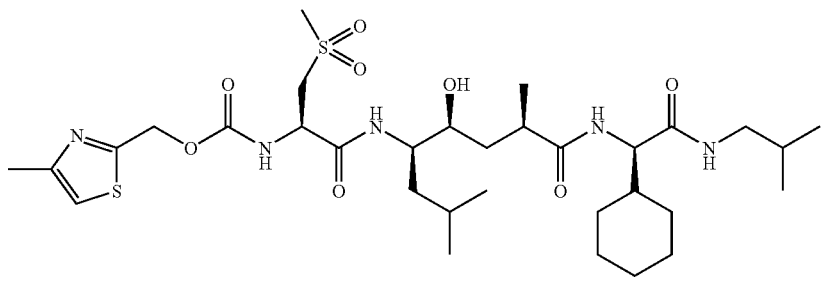
33
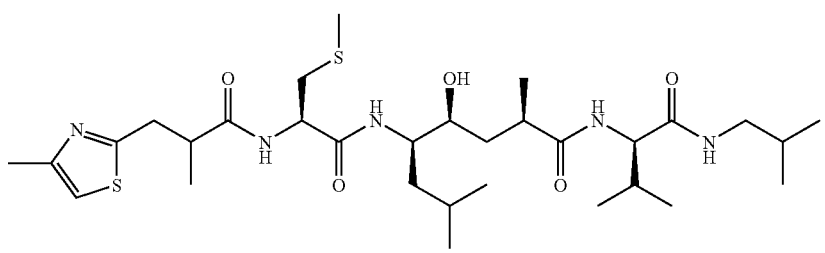
34
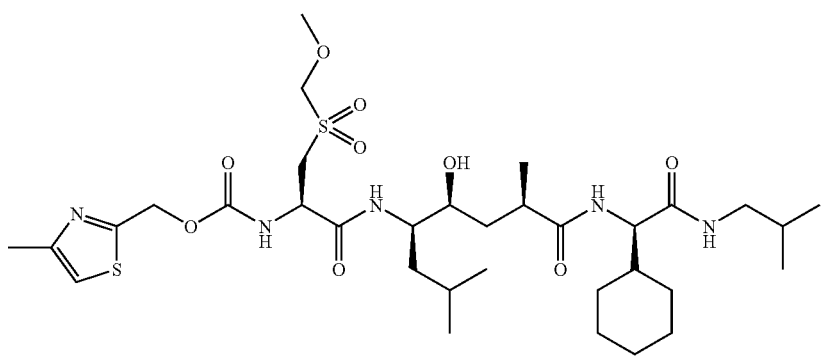
35
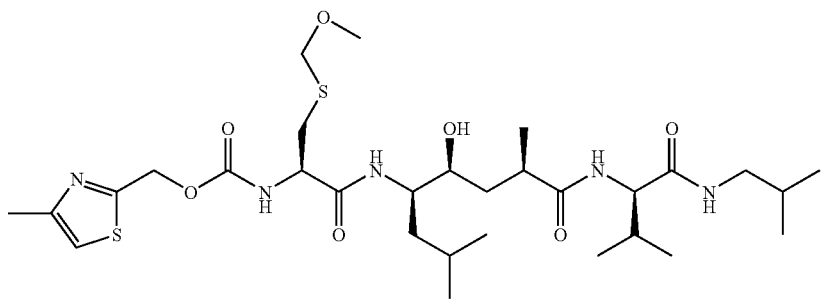
36

TABLE 1A-continued
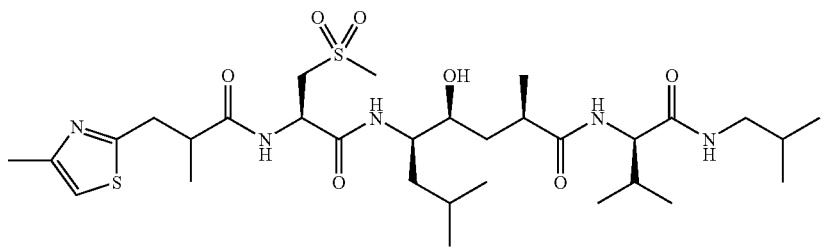
37
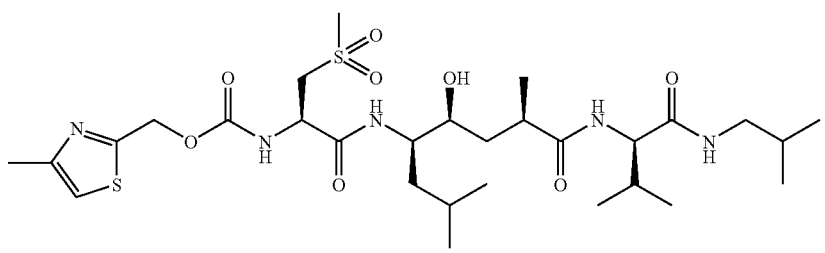
38
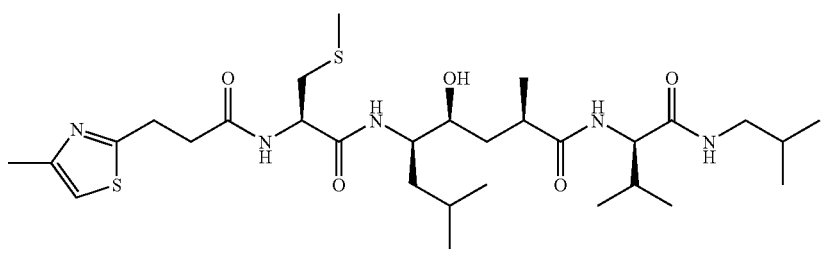
39
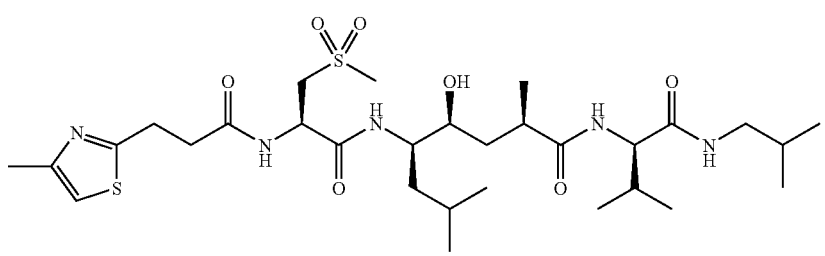
40
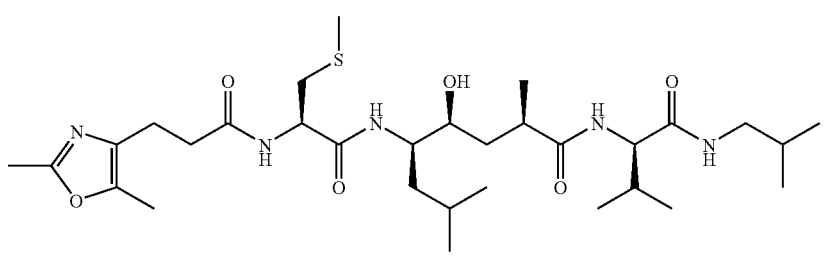
41

TABLE 1A-continued
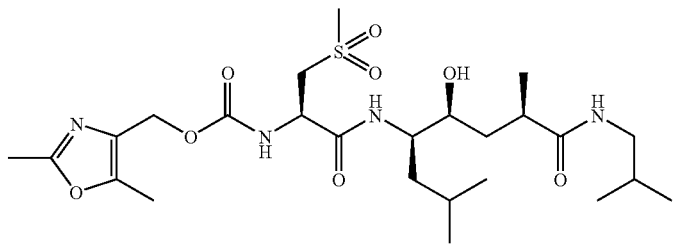
42
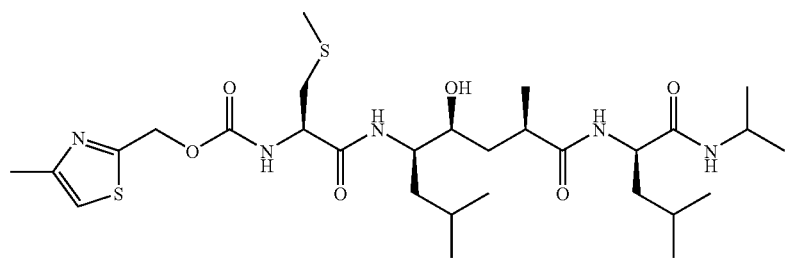
43
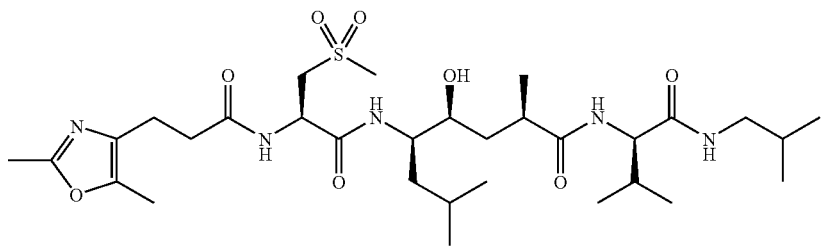
44
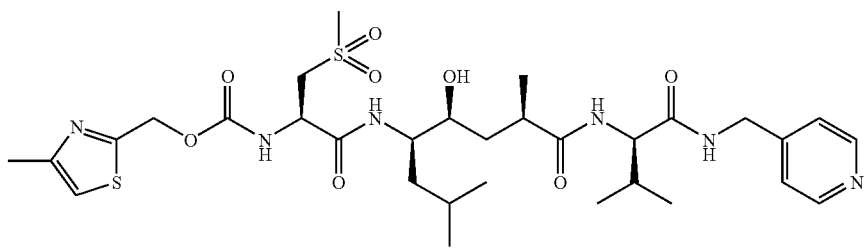
45
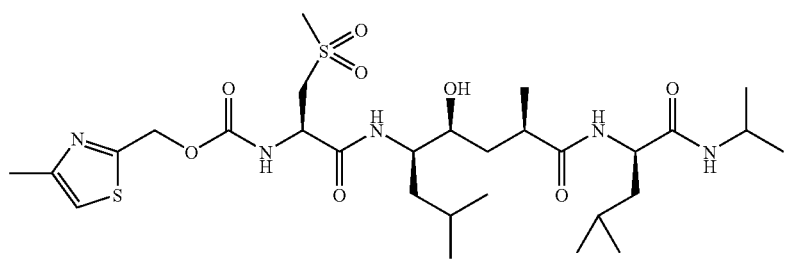
46

TABLE 1A-continued
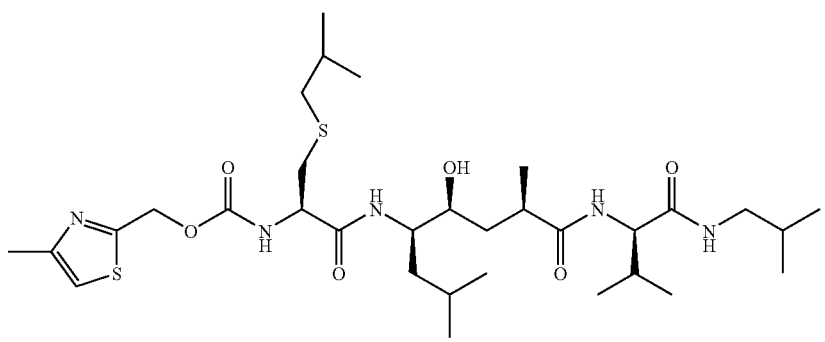
47
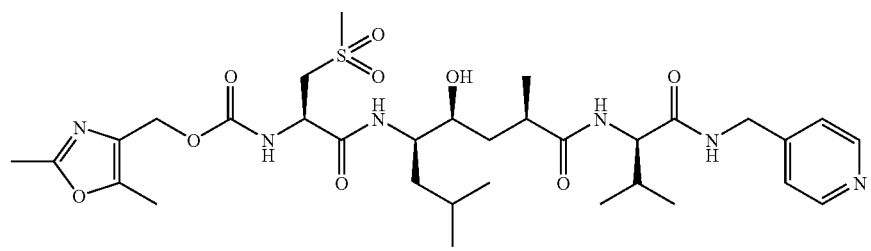
48
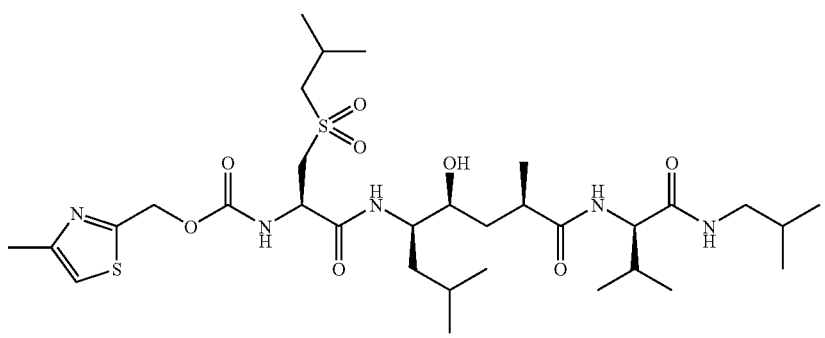
49
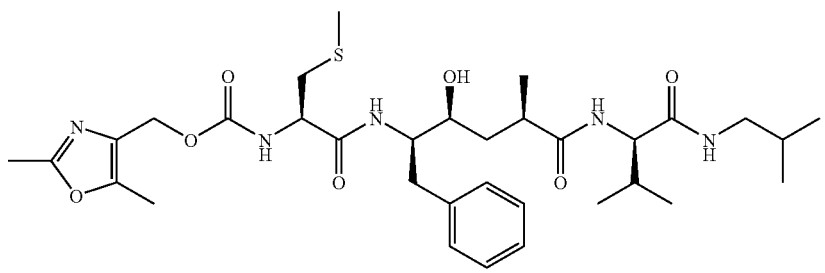
50

TABLE 1A-continued
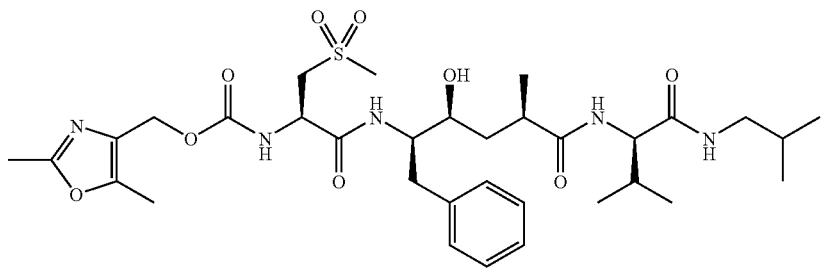
51
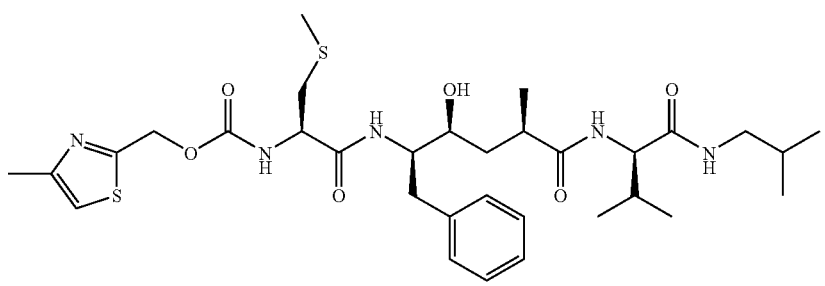
52
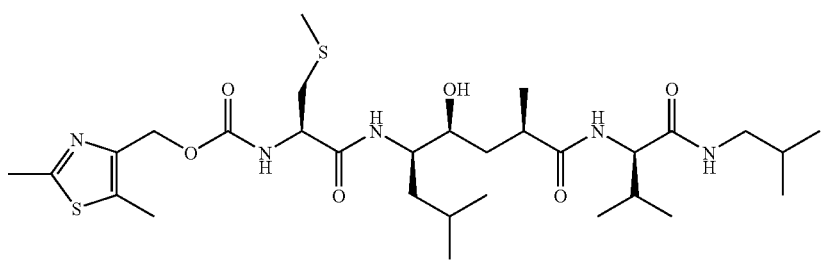
53
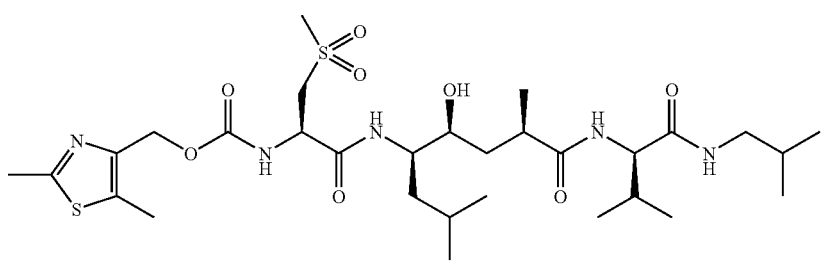
54
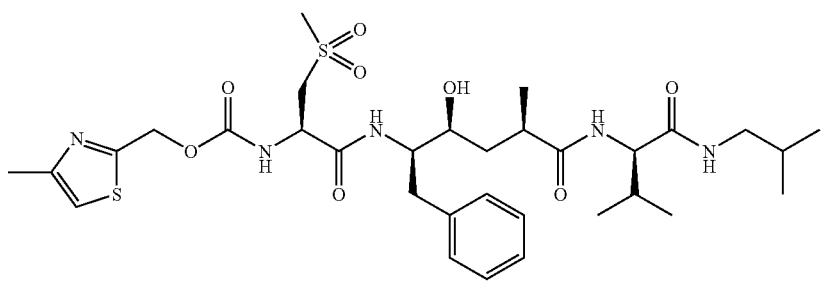
55

TABLE 1A-continued
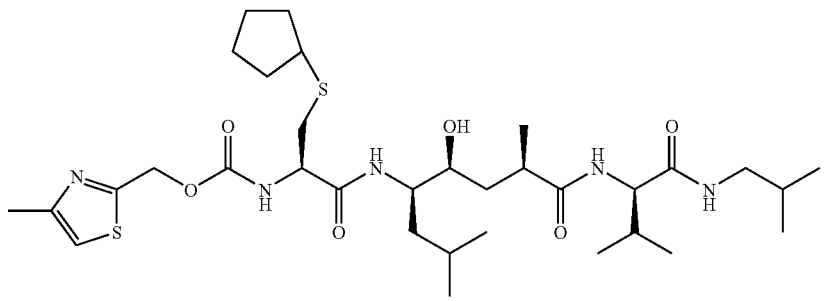
56
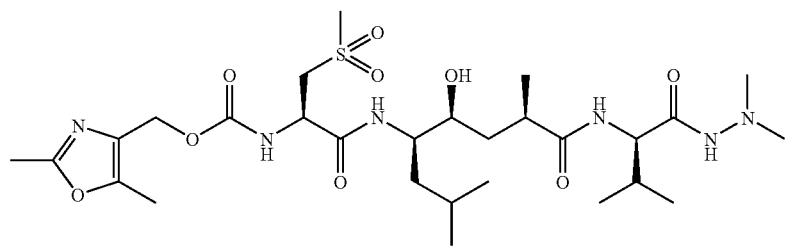
57
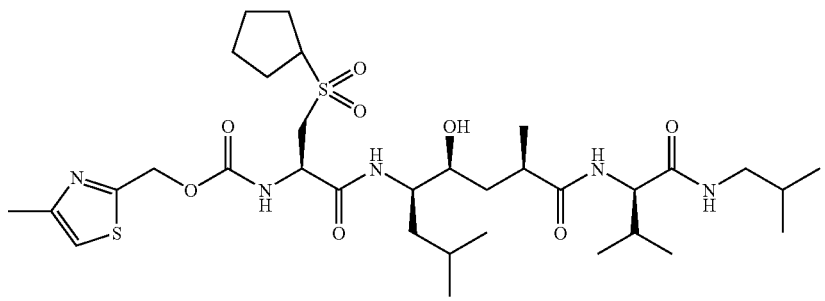
58
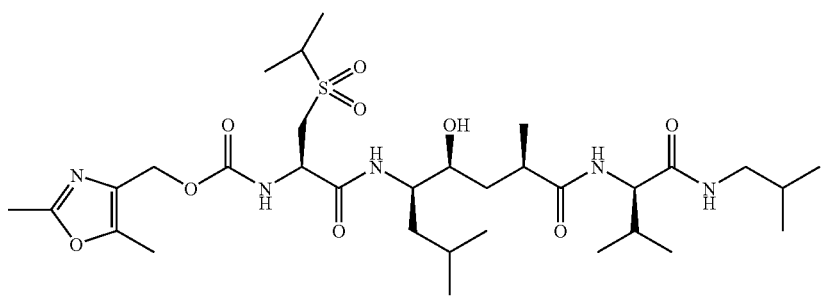
59

TABLE 1A-continued
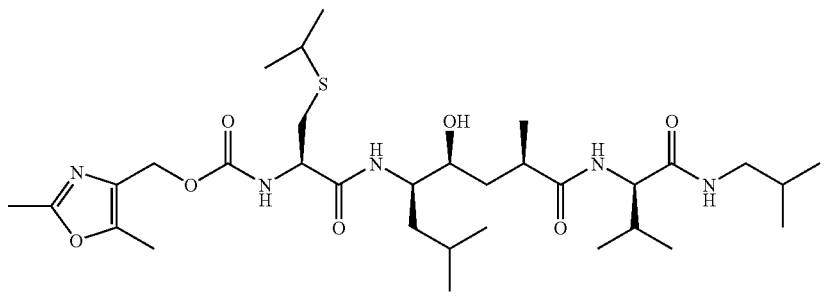
60
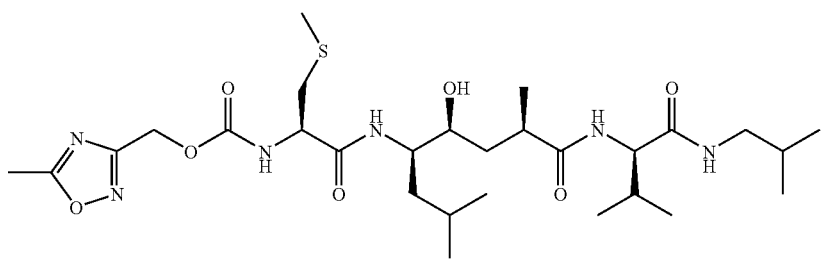
61
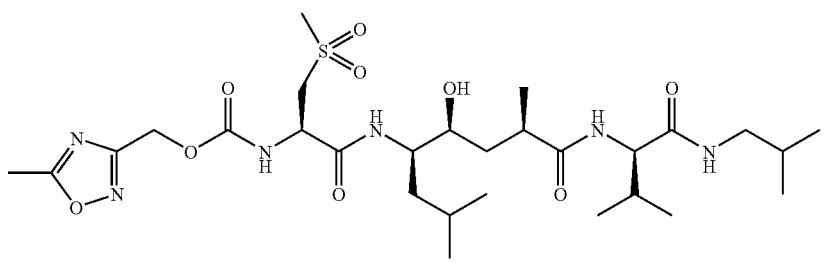
62
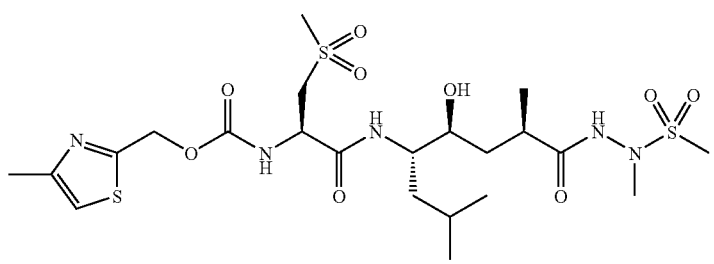
63
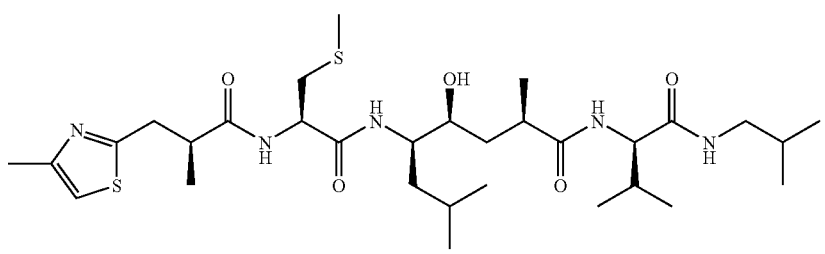
64

TABLE 1A-continued
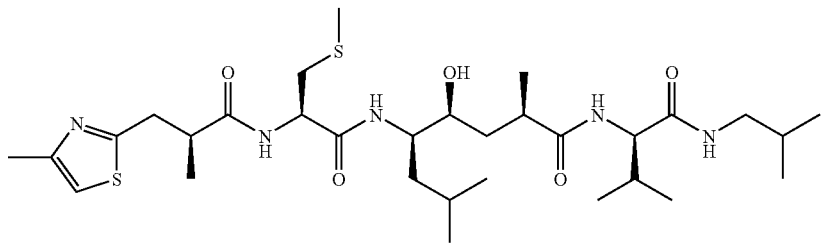
65
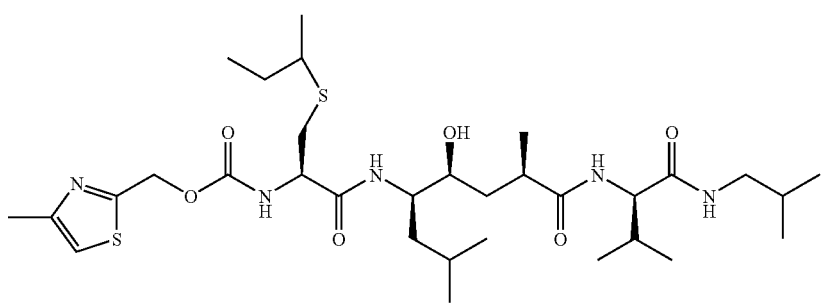
66
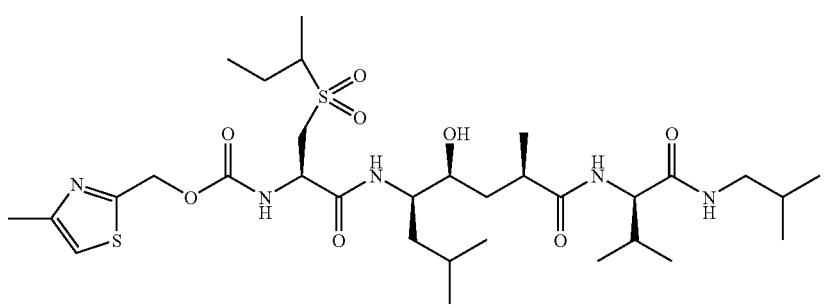
67
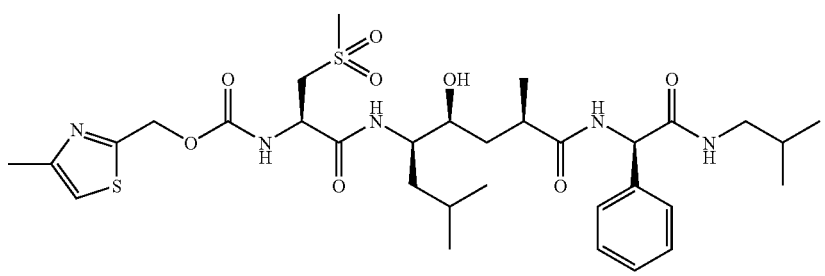
68
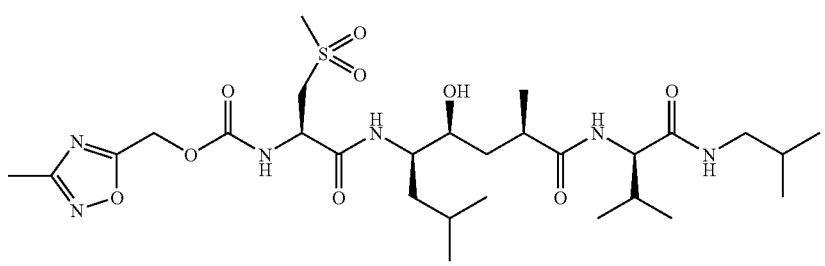
69

TABLE 1A-continued
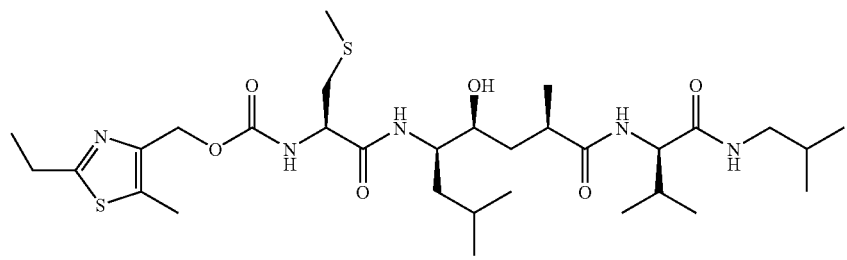
70
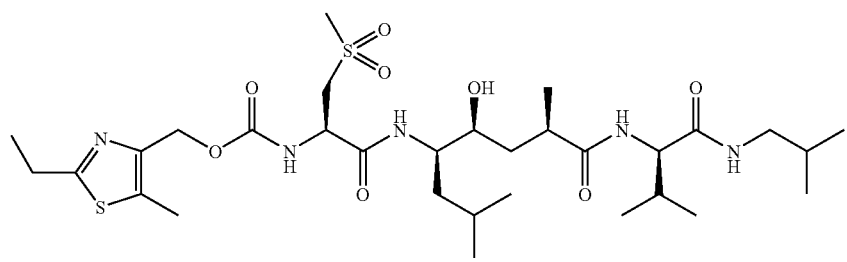
71
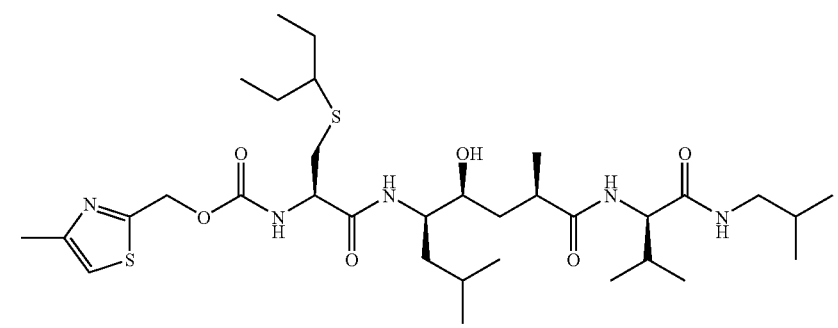
72
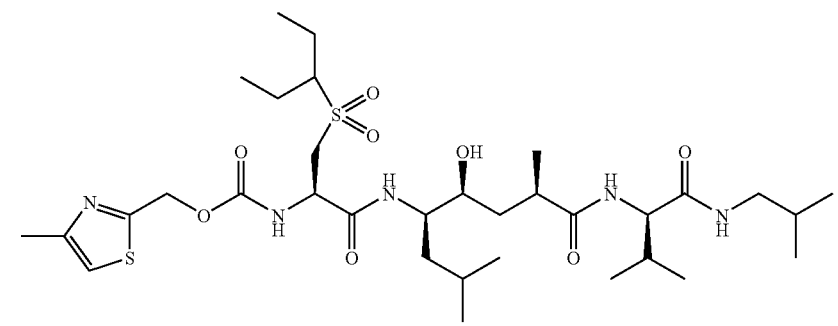
73

TABLE 1A-continued
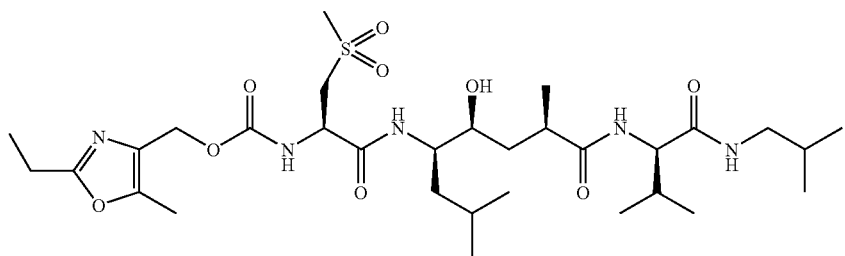
74
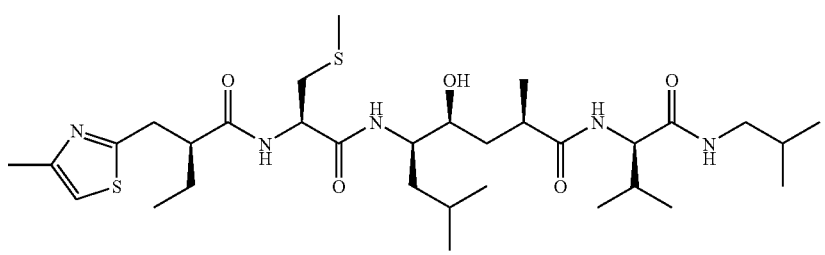
75
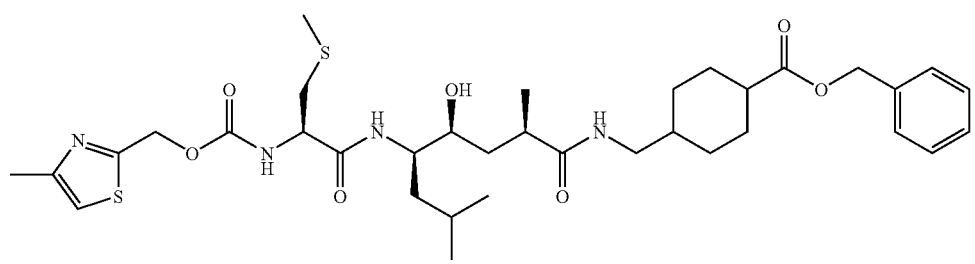
76
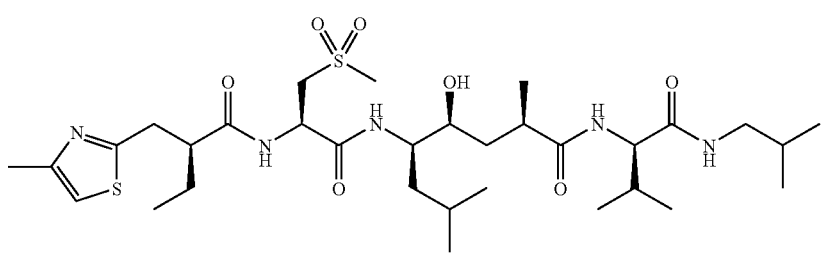
77
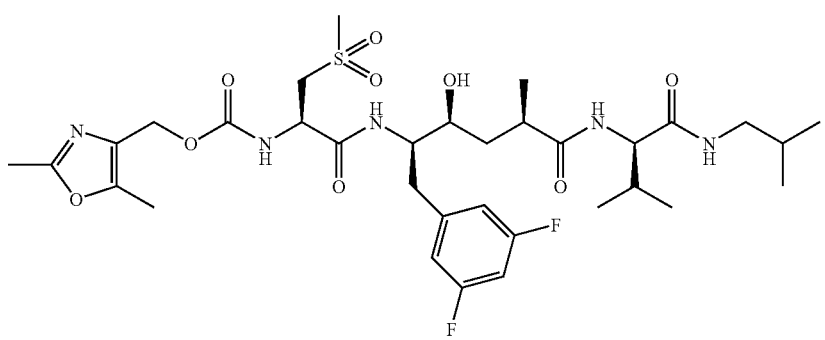
78

TABLE 1A-continued
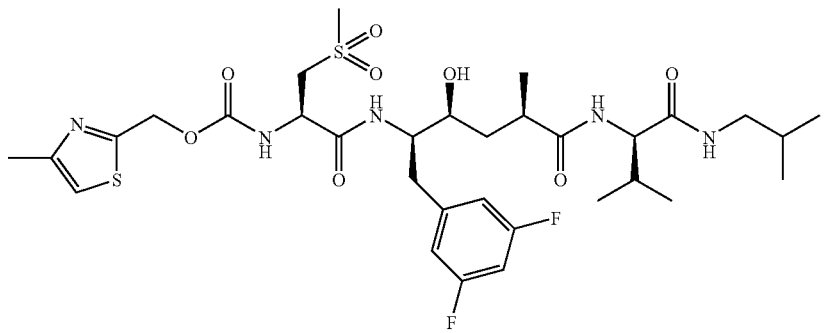
79
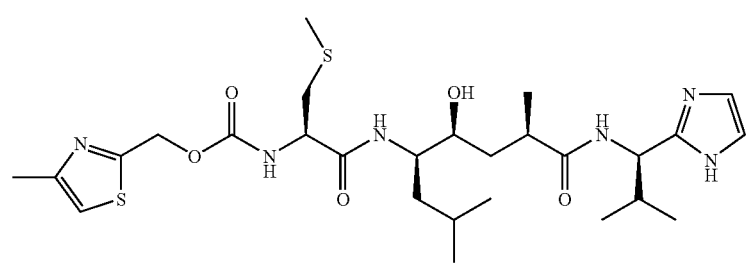
80
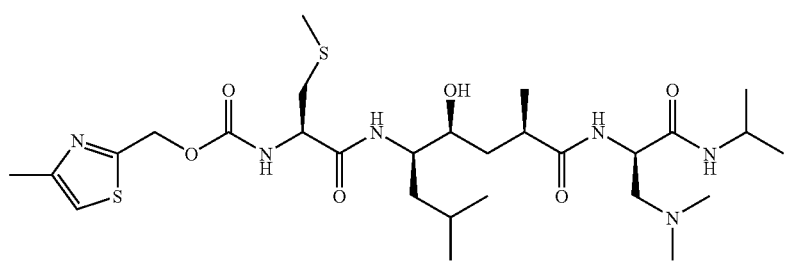
81
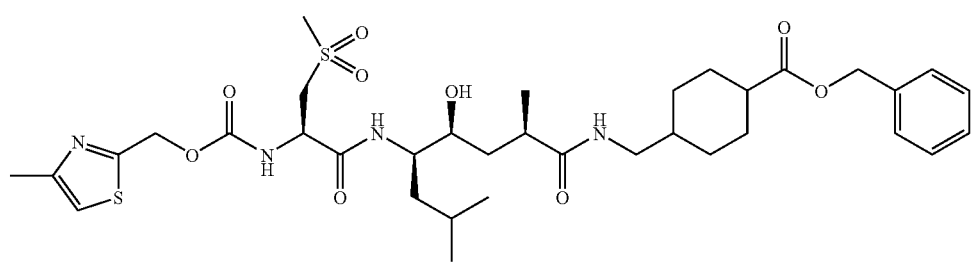
82
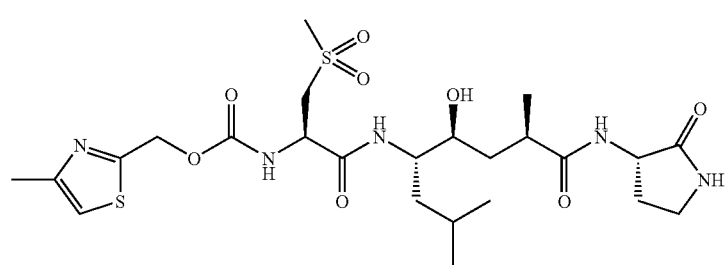
83

TABLE 1A-continued
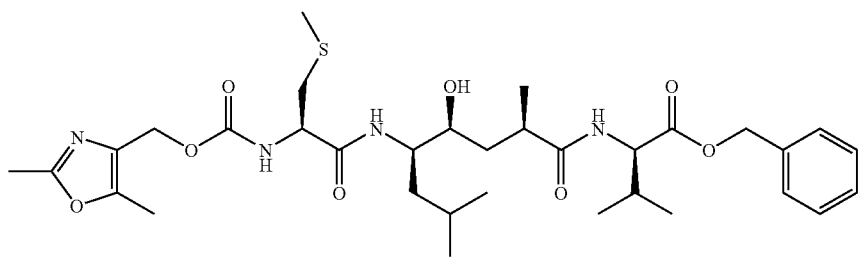
84
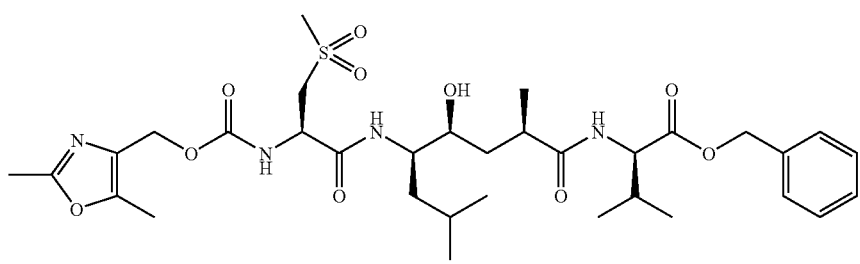
85
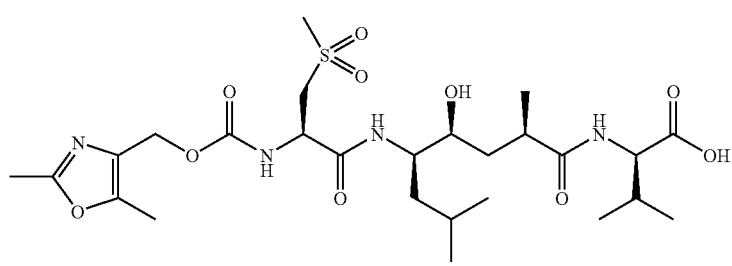
86
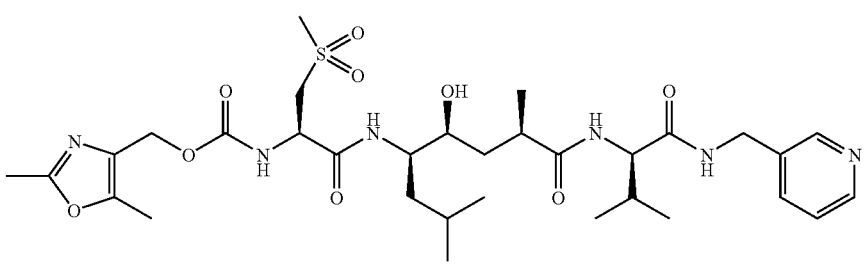
87
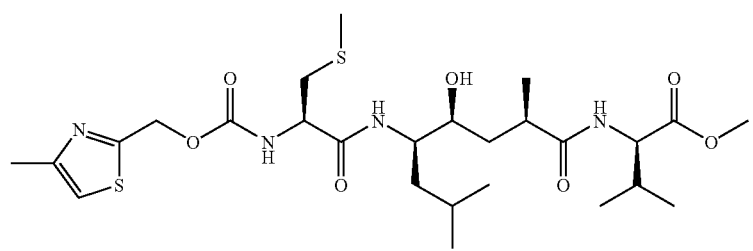
88

TABLE 1A-continued
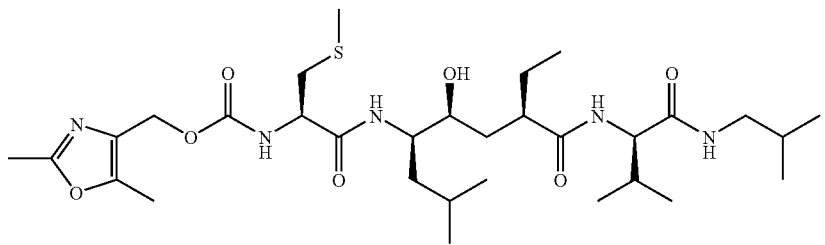
89
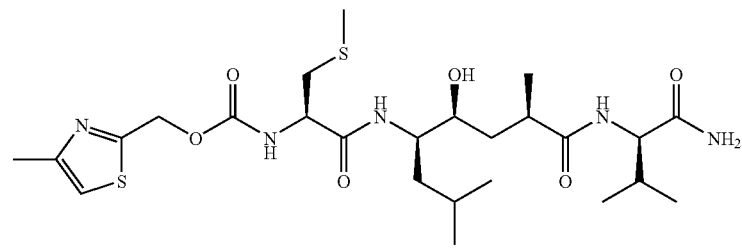
90
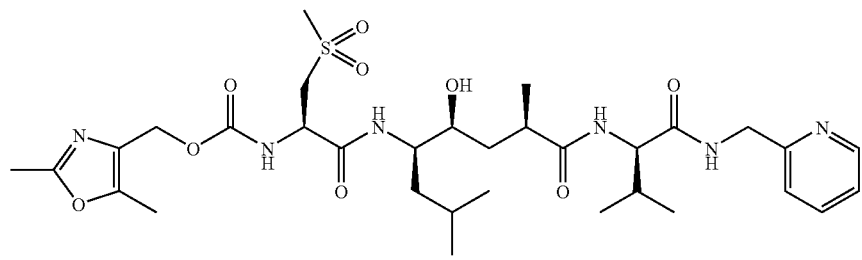
91
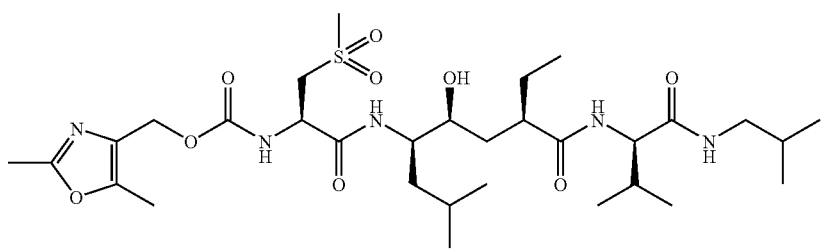
92
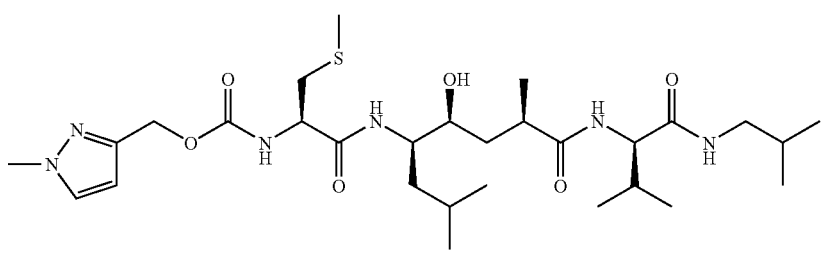
93

TABLE 1A-continued
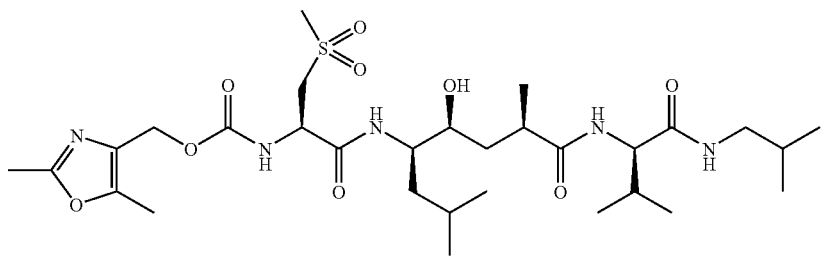
94
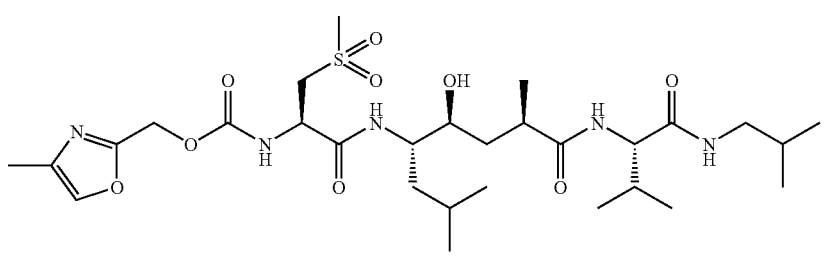
95
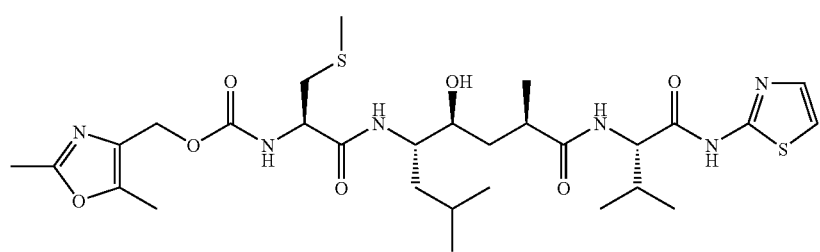
96
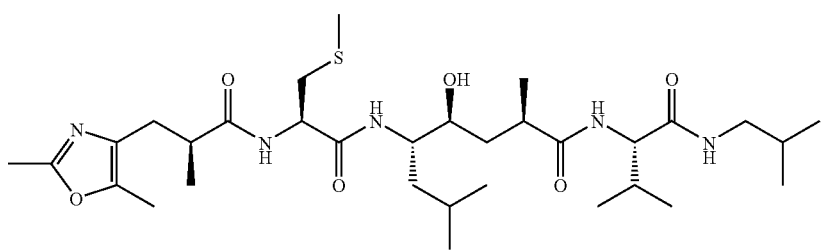
97
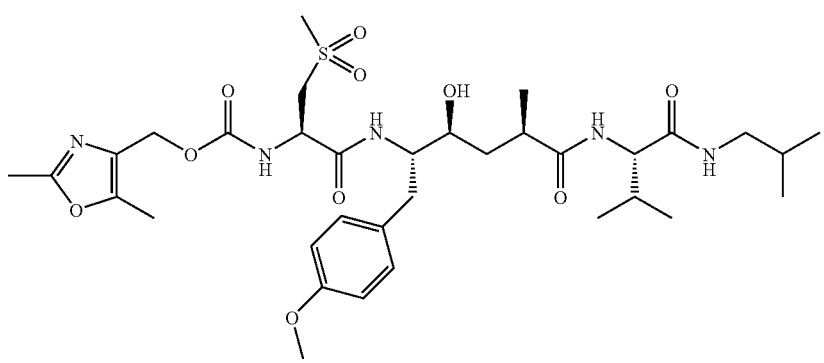
98

TABLE 1B

| Structure | M2 Ki (nM) | Cath D Ki (nM) | M1 Ki (nM) |
|---|---|---|---|
| 1 | ++ | + | + |
| 2 | ++ | + | + |
| 3 | ++ | ++ | + |
| 4 | + | ++ | + |
| 5 | ++ | + | + |
| 6 | − | + | ++ |
| 7 | ++ | ++ | ++ |
| 8 | ++ | + | ++ |
| 9 | ++ | + | ++ |
| 10 | ++ | ++ | ++ |
| 11 | − | ++ | + |
| 12 | − | + | + |
| 13 | + | − | ++ |
| 14 | ++ | ++ | ++ |
| 15 | + | + | + |
| 16 | ++ | + | + |
| 17 | ++ | ++ | + |
| 18 | ++ | ++ | ++ |
| 19 | ++ | ++ | ++ |
| 20 | + | + | + |
| 21 | + | ++ | + |
| 22 | ++ | + | + |
| 23 | ++ | ++ | + |
| 24 | − | ++ | + |
| 25 | + | + | ++ |
| 26 | + | + | + |
| 27 | + | ++ | + |
| 28 | + | + | + |
| 29 | ++ | ++ | + |
| 30 | ++ | + | + |
| 31 | ++ | + | + |
| 32 | ++ | ++ | + |
| 33 | + | − | + |
| 34 | ++ | ++ | + |
| 35 | ++ | + | + |
| 36 | ++ | ++ | ++ |
| 37 | ++ | + | + |
| 38 | ++ | + | + |
| 39 | ++ | ++ | + |
| 40 | ++ | + | + |
| 41 | ++ | ++ | + |
| 42 | − | ++ | − |
| 43 | ++ | ++ | + |
| 44 | ++ | + | ++ |
| 45 | + | + | − |
| 46 | ++ | + | + |
| 47 | ++ | ++ | + |
| 48 | ++ | + | + |
| 49 | ++ | + | ++ |
| 50 | + | ++ | ++ |
| 51 | ++ | ++ | ++ |
| 52 | ++ | ++ | + |
| 53 | ++ | ++ | ++ |
| 54 | ++ | + | ++ |
| 55 | ++ | ++ | ++ |
| 56 | ++ | ++ | + |
| 57 | ++ | + | + |
| 58 | ++ | + | + |
| 59 | ++ | + | + |
| 60 | ++ | ++ | + |
| 61 | + | ++ | − |
| 62 | − | + | − |
| 63 | − | − | − |
| 64 | + | ++ | + |
| 65 | ++ | ++ | ++ |
| 66 | ++ | ++ | + |
| 67 | ++ | + | + |
| 68 | ++ | + | + |
| 69 | + | + | + |
| 70 | ++ | ++ | ++ |
| 71 | ++ | + | + |
| 72 | ++ | ++ | + |
| 73 | ++ | + | + |
| 74 | ++ | + | + |
| 75 | ++ | ++ | + |
| 76 | − | ++ | − |
| 77 | ++ | ++ | + |
| 78 | + | ++ | ++ |
| 79 | ++ | ++ | ++ |
| 80 | − | + | − |
| 81 | − | − | − |
| 82 | − | ++ | − |
| 83 | − | − | − |
| 84 | − | + | − |
| 85 | + | + | + |
| 86 | + | − | + |
| 87 | ++ | + | ++ |
| 88 | − | + | − |
| 89 | ++ | ++ | + |
| 90 | − | NM | NM |
| 91 | ++ | NM | NM |
| 92 | NM | NM | NM |
| 93 | + | ++ | + |
| 94 | ++ | + | + |
| 95 | ++ | + | − |
| 96 | + | ++ | + |
| 97 | ++ | ++ | + |
| 98 | − | ++ | + |

In Table 1B, the symbol "++" represents a Ki of less than 100 nM; the symbol "+" represents a Ki of 100 to 1000 nM; the symbol "−" represents a Ki of greater than 1000 Nm; and "NM" means not measured.

Example 5

Inhibition of Memapsin 1 Beta-Secretase Activity and Cathepsin D Activity

A substrate peptide $NH_3$-ELDLAVEFWHDR-$CO_2$ was dissolved at 2 mg/ml in 10% glacial acetic acid and diluted into 0.009 M NaOH to obtain µM concentration at pH 4.1. After equilibration at 37 degrees C., the reactions were initiated by the addition of an aliquot of memapsin 2. Aliquots were removed at time intervals, and combined with an equal volume of MALDI-TOF matrix (α-hydroxycinnamic acid in acetone, 20 mg/ml) and immediately spotted in duplicate onto a stainless-steel MALDI sample plate. MALDI-TOF mass spectrometry was performed on a PE Biosystems Voyager DE instrument at the Molecular Biology Resource Center on campus. The instrument was operated at 25,000 accelerating volts in positive mode with a 150 ns delay. Ions with a mass-to-charge ratio (m/z) were detected in the range of 650-2000 atomic mass units. Data were analyzed by the Voyager Data Explorer module to obtain ion intensity data for mass species of substrates and corresponding products in a given mixture. Relative product formation was calculated as the ratio of signal intensity of the product to the sum of signal intensities of both product and the corresponding substrate. Relative product formed per unit time was obtained from non-linear regression analysis of the data representing the initial 15% formation of product using the model:

$$1 - e^{-kT},$$

where k is the relative hydrolytic rate constant and T is time in seconds. Initial rates were expressed relative to uninhibited controls and fit to a tight-binding model of competitive inhibition as above. Results are shown in Tables 1A and 1B above.

Example 6

Cellular Aβ IC50 Determinations

The potency of compounds against memapsin 2 activity was determined in a cellular assay of Aβ production. Compounds that successfully penetrate the cell membrane demonstrate their ability to inhibit memapsin 2 activity in endosomal compartments, thus blocking the production of Aβ. Chinese hamster ovary cells that over-express human APP695 with the London and Swedish mutations were seeded in multi-well plates at 10% confluency. Compounds were dissolved in DMSO to concentrations near 1 mM, and diluted into culture media to a final concentration near 4 μM (final 0.4% DMSO). Compounds were diluted serially and applied to cells in multi-well plates 48 h after seeding. Incubation was continued in 5% $CO_2$ at 37 degrees C. for 24 h. Aliquots were removed and assayed for $A\beta_{40}$ content using a sandwich ELISA (BioSource International). Amount of $A\beta_{40}$ over the range of concentration of compounds, relative to control incubations, were fit to a 4-parameter $IC_{50}$ model. Results are shown in Table 2 below.

TABLE 2

| Compound | IC50 | Compound | IC50 | Compound | IC50 |
|---|---|---|---|---|---|
| 30 | ++ | 66 | ++ | 4 | + |
| 60 | ++ | 32 | ++ | 38 | + |
| 92 | ++ | 88 | ++ | 55 | + |
| 94 | ++ | 48 | ++ | 68 | + |
| 9 | ++ | 2 | ++ | 93 | + |
| 90 | ++ | 57 | ++ | 39 | − |
| 36 | ++ | 8 | ++ | 86 | − |
| 64 | ++ | 22 | ++ | 37 | − |
| 72 | ++ | 54 | ++ | 40 | − |
| 79 | ++ | 47 | ++ | 5 | − |
| 75 | ++ | 34 | ++ | 71 | − |
| 77 | ++ | 46 | ++ | 18 | − |
| 58 | ++ | 53 | ++ | 7 | − |
| 3 | ++ | 43 | + | 91 | − |
| 74 | ++ | 50 | + | 56 | − |
| 58 | ++ | 59 | + | 49 | − |
| 3 | ++ | 31 | + | 35 | − |
| 74 | ++ | 16 | + | 19 | − |
| 67 | − | 73 | + | | |
| 29 | ++ | 17 | + | | |
| 95 | ++ | 78 | + | | |

In Table 2 above, the symbol "++" indicates an IC50 of less than 6 μM; "+" indicates an IC50 from 6 to 100 μM; and "−" indicates an IC50 of greater than 100 μM.

What is claimed is:

1. A compound represented by the following structural formula:

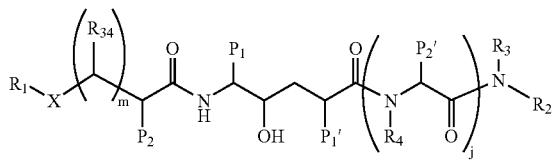

or optical isomers, diastereomers, or pharmaceutically acceptable salts thereof wherein:
X is —NH—C(O)—;
m is 0;
j is 1;
$P_1$ is a substituted or unsubstituted aliphatic, substituted or unsubstituted aralkyl, substituted or unsubstituted heteroalkyl, or substituted or unsubstituted heteroaralkyl;
$P_1'$, and $P_2'$ are each, independently, a substituted or unsubstituted aliphatic, substituted or unsubstituted heteroalkyl, substituted or unsubstituted aralkyl, or substituted or unsubstituted heteroaralkyl;
$R_1$ is —$C_{15}R_{16}$, or —$OR_{15}$;
wherein $R_{16}$ is hydrogen, aliphatic, —$NR_9R_{10}$, or —$OR_9$, wherein
$R_9$ and $R_{10}$ are each, independently, H, or aliphatic; and
$R_{15}$ is a $C_1$-$C_3$ alkylene substituted with a substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothienopyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisazolyl, or substituted or unsubstituted dimethyihydantoin;
$R_4$ is H, or substituted or unsubstituted aliphatic;
$R_2$ is H;
$R_3$ is an unsubstituted alkyl, unsubstituted pyridinyl, or pyridinyl substituted with an unsubstituted $C_1$-$C_5$ alkyl; and
$P_2$ is —$C(R_{35})(R_{36})$—$S(O)_t$-L-$R_{12}$, wherein
t is 0, 1, or 2,
L is a bond, and
$R_{12}$ is:
(a) aliphatic; heteroalkyl; heterocycle; aryl; heteroaryl;
(b) aliphatic substituted with an oxy, halogen, —CN, —OH, acetyl, aliphatic, heteroalkyl, heterocycle, aryl, or heteroaryl;
(c) heteroalkyl substituted with an oxy, halogen, —CN, —OH, acetyl, aliphatic, heteroalkyl, heterocycle, aryl, or heteroaryl;
(d) heterocycle substituted with an oxy, halogen, —CN, —OH, acetyl, aliphatic, heteroalkyl, heterocycle, aryl, or heteroaryl;
(e) aryl substituted with an oxy, halogen, —CN, —OH, acetyl, aliphatic, heteroalkyl, heterocycle, aryl, or heteroaryl; or
(f) heteroaryl substituted with an oxy, halogen, —CN, —OH, acetyl, aliphatic, heteroalkyl, heterocycle, aryl, or heteroaryl; and $R_{35}$ and $R_{36}$ are each, independently hydrogen, halogen, substituted or unsubstituted aliphatic, substituted or unsubstituted heteroalkyl, substituted or unsubstituted heterocycle, substituted or unsubstituted aryl, or substituted or unsubstituted heteroaryl.

2. The compound of claim 1, wherein each halogen is selected from fluorine or chlorine.

3. The compound of claim 1, wherein $R_{12}$ is:
(a) aliphatic; heteroalkyl; heterocycle; aryl; heteroaryl;
(b) aliphatic substituted with an oxy, acetyl, aliphatic, heteroalkyl, or alkylsulfonyl;
(c) heteroalkyl substituted with an oxy, —CN, aliphatic, or heteroalkyl;
(d) heterocycle substituted with an oxy, acetyl, aliphatic, heteroalkyl, or alkylsulfonyl;
(e) aryl substituted with an aliphatic, heteroalkyl, or alkylsulfonyl; or
(f) heteroaryl substituted with an aliphatic, heteroalkyl, or alkylsulfonyl.

4. The compound of claim 3, wherein $R_{12}$ is a polyether.

5. The compound of claim 4, wherein said polyether has the formula:

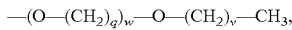

—(O—(CH$_2$)$_q$)$_w$—O—(CH$_2$)$_v$—CH$_3$, wherein,
q and v are each, independently, 1, 2, 3, 4, or 5; and
w is 1, 2, 3, 4, 5, 6, 7, 8, 9, or 10.

6. The compound of claim 5, wherein
q and v are each, independently 1 or 2; and
w is 1, 2, 3, 4, 5, 6, 7, or 8.

7. The compound of claim 1, wherein $P_1$ is a substituted or unsubstituted phenylalkyl, or substituted or unsubstituted pyridinylalkyl.

8. The compound of claim 1, wherein $P_1$ is $C_1$-$C_5$ alkyl substituted with:
(a) halogen; unsubstituted phenyl; unsubstituted pyridinyl;
(b) phenyl substituted with a halogen, an —OH, an alkoxy, or an aliphatic; or
(c) pyridinyl substituted with a halogen, an —OH, an alkoxy, or an aliphatic.

9. The compound of claim 1, wherein $P_1$ is methyl substituted with a halogen, phenyl, pyridinyl, 3,5-difluorophenyl, 4-hydroxyphenyl, 3-chloro-4-hydroxyphenyl, or 3-chloro-4-mehtoxyphenyl.

10. The compound of claim 1, wherein $P_1$ is a —CH$_2$—CH(CH$_3$)—CH$_3$.

11. The compound of claim 1, wherein $P_1$ is an arylalkyl substituted with a halogen.

12. The compound of claim 11, wherein the halogen of $P_1$ is fluorine.

13. The compound of claim 1, wherein $P_1'$ and $P_2'$ are each, independently, substituted or unsubstituted aliphatic, or substituted or unsubstituted arylalkyl.

14. The compound of claim 1, wherein $P_1'$ and $P_2'$ are each, independently, substituted or unsubstituted aliphatic.

15. The compound of claim 1, wherein $P_1'$ and $P_2'$ are each, independently, $C_1$-$C_5$ alkyl.

16. The compound of claim 1, wherein
$R_{15}$ is a $C_1$-$C_3$ alkylene substituted with a substituted or unsubstituted pyrazolyl, substituted or unsubstituted oxazolyl, substituted or unsubstituted thiazolyl, substituted or unsubstituted furanyl, or substituted or unsubstituted dimethyihydantoin.

17. The compound of claim 1, wherein
$R_{15}$ is a $C_1$-$C_3$ alkylene substituted with a substituted or unsubstituted 1-pyrazolyl, substituted or unsubstituted 4-oxazolyl, substituted or unsubstituted 2-oxazolyl, substituted or unsubstituted 2-thiazolyl, or substituted or unsubstituted 2-furanyl.

18. The compound of claim 1, wherein $R_{15}$ is a $C_1$-$C_3$ alkylene substituted with a
1-pyrazolyl substituted with an aliphatic, or heteroalkyl;
4-oxazolyl substituted with an aliphatic, or heteroalkyl;
2-oxazolyl substituted with an aliphatic, or heteroalkyl;
2-thiazolyl substituted with an aliphatic, or heteroalkyl; or
2-furanyl substituted with an aliphatic, or heteroalkyl.

19. The compound of claim 1, wherein $R_{15}$ is a $C_1$-$C_3$ alkylene substituted with a
1-pyrazolyl substituted with a $C_1$-$C_5$ alkyl, or 2 to 6 membered heteroalkyl;
4-oxazolyl substituted with a $C_1$-$C_5$ alkyl, or 2 to 6 membered heteroalkyl;
2-oxazolyl substituted with a $C_1$-$C_5$ alkyl, or 2 to 6 membered heteroalkyl;
2-thiazolyl substituted with a $C_1$-$C_5$ alkyl, or 2 to 6 membered heteroalkyl; or
2-furanyl substituted with a $C_1$-$C_5$ alkyl, or 2 to 6 membered heteroalkyl.

20. The compound of claim 1, wherein $R_{15}$ is a $C_1$-$C_3$ alkylene substituted with a
1-pyrazolyl substituted with a $C_1$-$C_5$ alkyl;
4-oxazolyl substituted with a $C_1$-$C_5$ alkyl;
2-oxazolyl substituted with a $C_1$-$C_5$ alkyl;
2-thiazolyl substituted with a $C_1$-$C_5$ alkyl; or
2-furanyl substituted with a $C_1$-$C_5$ alkyl.

21. The compound of claim 1, wherein $R_{15}$ is methylene substituted with:
(a) a 1-pyrazolyl substituted with a $C_1$-$C_5$ alkyl at the 3 position, the 5 position, or the 3 and 5 position;
(b) a 4-oxazolyl substituted with a $C_1$-$C_5$ alkyl at the 2 position, the 5 position, or the 2 and 5 position;
(c) a 2-oxazolyl substituted with a $C_1$-$C_5$ alkyl at the 4 position;
(d) a 2-thiazolyl substituted with a $C_1$-$C_5$ alkyl at the 4 position; or
(e) a 2-furanyl substituted with a $C_1$-$C_5$ alkyl at the 5 position.

22. The compound of claim 1, wherein
$R_2$ is H; and
$R_3$ is an unsubstituted $C_1$-$C_5$ alkyl, unsubstituted pyridinyl, or pyridinyl substituted with an unsubstituted $C_1$-$C_5$ alkyl.

23. The compound of claim 1, wherein $R_2$ and $R_3$ together with the nitrogen to which they are attached form a morpholino, piperazinyl, or piperidinyl, wherein the morpholino, piperazinyl and piperidinyl are optionally substituted with one or more aliphatics.

24. The compound of claim 1, wherein the compound is represented by the formula

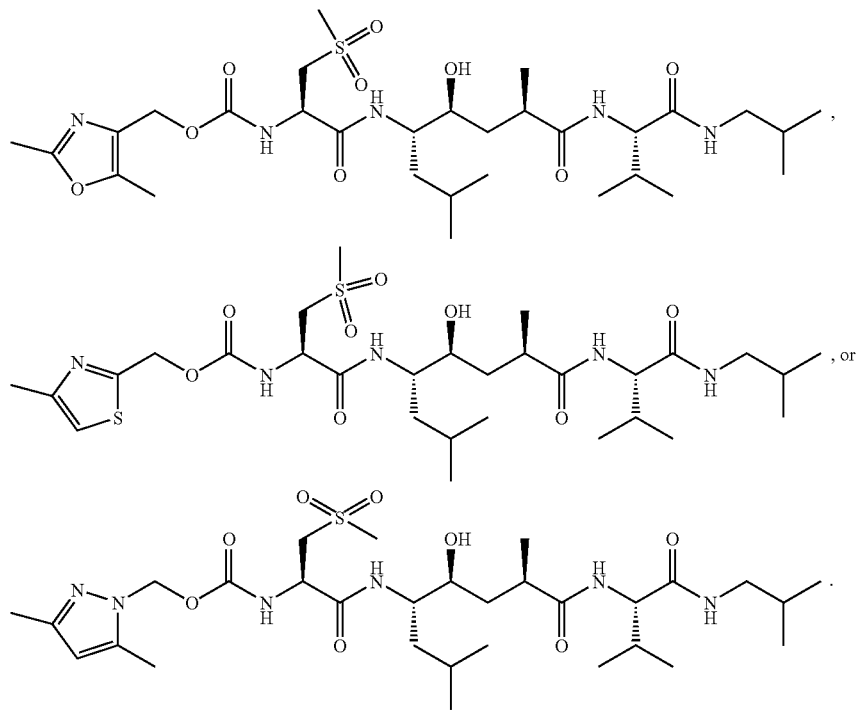
25. The compound of claim 1, wherein the compound is represented by the formula
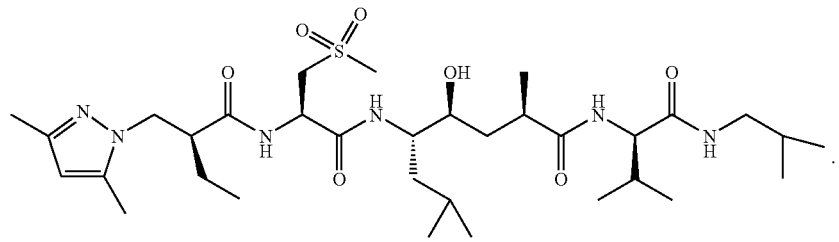
* * * * *

UNITED STATES PATENT AND TRADEMARK OFFICE
CERTIFICATE OF CORRECTION

PATENT NO.         : 7,335,632 B2
APPLICATION NO. : 10/944117
DATED                 : February 26, 2008
INVENTOR(S)       : Arun K. Ghosh et al.

It is certified that error appears in the above-identified patent and that said Letters Patent is hereby corrected as shown below:

- In column 1, line 30, please replace "inter alia" with --*inter alia*--

- In column 5, line 28, please replace "inlcude" with --include--

- In column 8, line 33, please replace "PCT/USO2/34324" with

--PCT/US02/34324--

- In column 9, line 12, please add after the formula, along the right margin --(I).--

- In column 14, line 1, please replace "$R^{15}$ and $R^{16}$" with --$R_{15}$ and $R_{16}$--

- In column 16, line 20, please replace "includes" with --include--

- In column 16, line 24, please replace "in vitro" with --*in vitro*--

- In column 16, line 26, please replace "in vitro" with --*in vitro*--

- In column 19, line 48, please replace "in vitro" with --*in vitro*--

- In column 19, line 55, please replace "in vitro" with --*in vitro*--

- In column 19, line 59, please replace "perforemd" with --performed--

- In column 20, line 52-53, please replace "in vitro" with --*in vitro*--

- In column 20, line 54-55, please replace "in vitro" with --*in vitro*--

- In column 24, line 24, please replace "inter alia" with --*inter alia*--

- In column 26, line 16, please replace "K" with --$K_i$--

- In column 26, line 66, please replace "α-amy-" with --β-amy- --

- In column 27, lines 6, 7, and 10, please replace "in vitro" with --*in vitro*--

- In column 28, line 40, please replace "groups" with --group--

- In column 29, line 21, please replace "Pat App No" with --Application No.--

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

- In column 32, line 20, please replace "he" with --The--

- In column 34, line 44, please replace "NaHCO3" with --$NaHCO_3$--

- In column 34, line 54, please replace "OH." with --OH--

- In column 34, line 60, please replace "resulting" with --resulting mixture--

- In column 37, line 10, please replace "and" with --an--

- In column 37, line 22, please replace "$^1$H NMR" with --$^1$H-NMR--

- In column 37, line 54, please replace "ours" with --hours--

- In column 38, line 37, please replace "$[a]^{D23}$" with --$[a]_D^{23}$--

- In column 39, line 24, please replace "DMSO-D" with --DMSO-$d^6$--

- In column 40, line 3 and 34, please replace "$^1$H NMR" with --$^1$H-NMR--

- In column 40, line 59, please replace "saturatedaque-" with --saturated aque--

- In column 40, line 63, please replace "waspurified" with --was purified--

- In column 41, line 58, please replace "acid 1e" with --acid 11e--

- In column 42, line 5 and 62, please replace "$^1$H NMR" with --$^1$H-NMR--

- In column 44, line 21, please replace "2.99 (m, 1H), 2.99 (m, 1H)" with --2.99 (m, 1H)--

- In column 44, the last structure, please replace

" 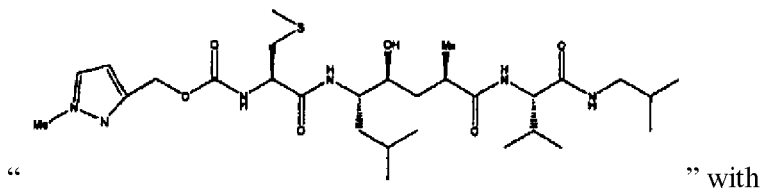 " with

UNITED STATES PATENT AND TRADEMARK OFFICE
CERTIFICATE OF CORRECTION

PATENT NO. : 7,335,632 B2  Page 3 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

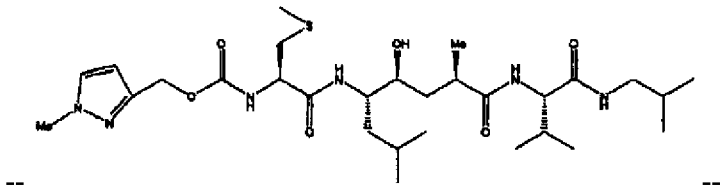

-- --

• In column 47, line 4-5, please replace "1.91 (m, 1H), 1.91 (m, 1H)" with --1.91 (m, 1H)--

• In column 51, line 39, please replace "M.p." with --m.p.--

• In column 60, line 21, please replace "experiment" with --experiments--

• In column 59-60, in Table 1A, structures 1 and 2, please replace

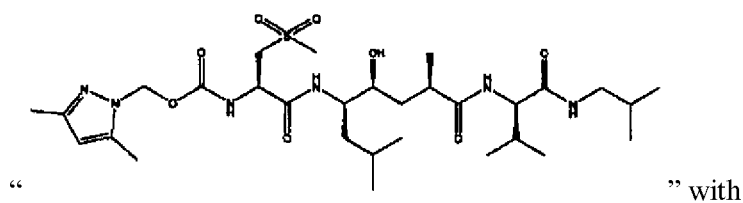

" with

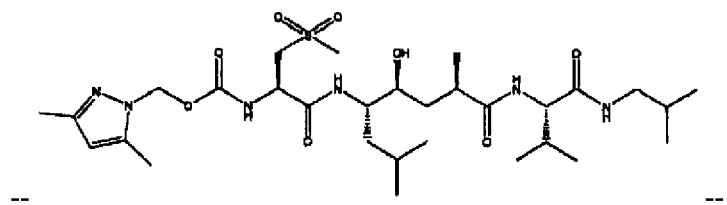

-- --

• In column 61-62, in Table 1A-continued, structure 3, please replace

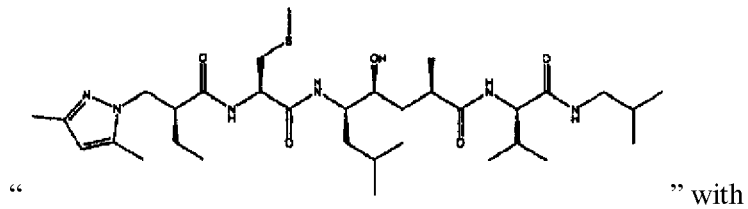

" with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

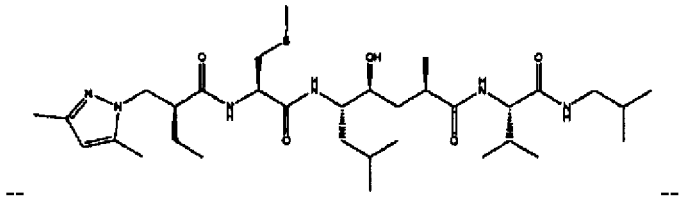
--  --

• In column 61-62, in Table 1A-continued, structure 4, please replace

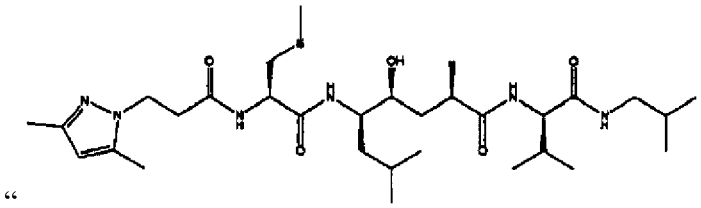
"  " with

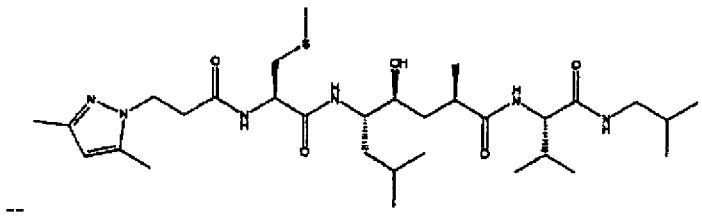
--  --

• In column 61-62, in Table 1A-continued, structure 5, please replace

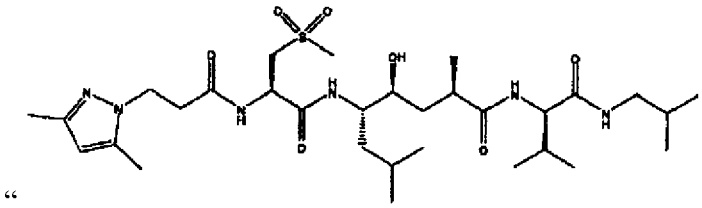
"  " with

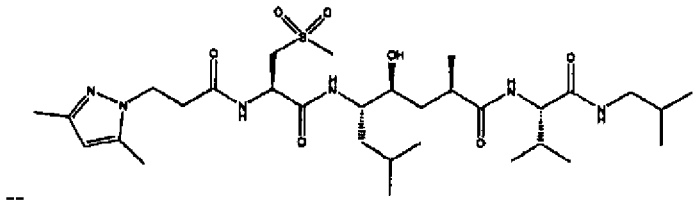
--  --

UNITED STATES PATENT AND TRADEMARK OFFICE
CERTIFICATE OF CORRECTION

PATENT NO. : 7,335,632 B2  Page 5 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

• In column 61-62, in Table 1A-continued, structure 6, please replace

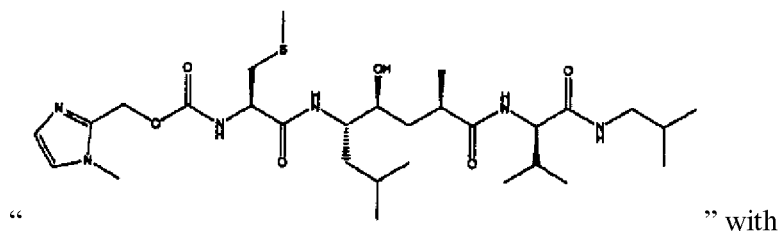

" " with

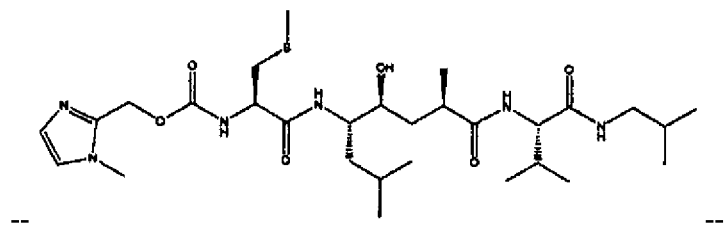

-- --

• In column 61-62, in Table 1A-continued, structure 7, please replace

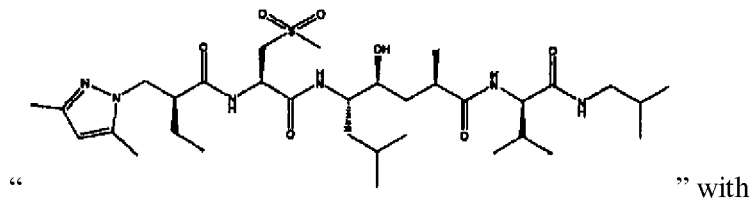

" " with

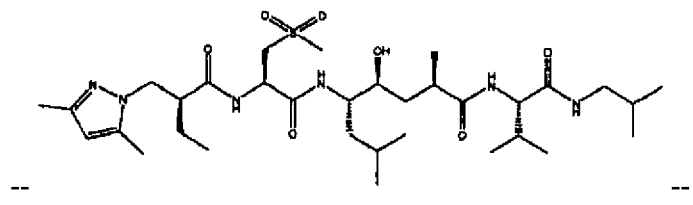

-- --

• In column 63-64, in Table 1A-continued, structure 8, please replace

UNITED STATES PATENT AND TRADEMARK OFFICE
CERTIFICATE OF CORRECTION

PATENT NO. : 7,335,632 B2 Page 6 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

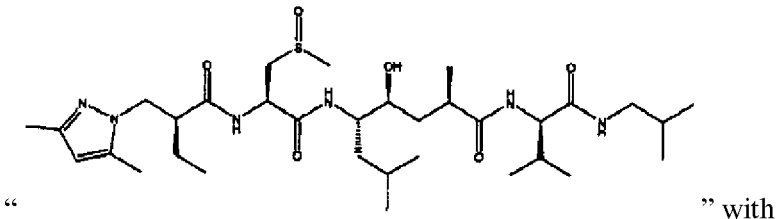

" 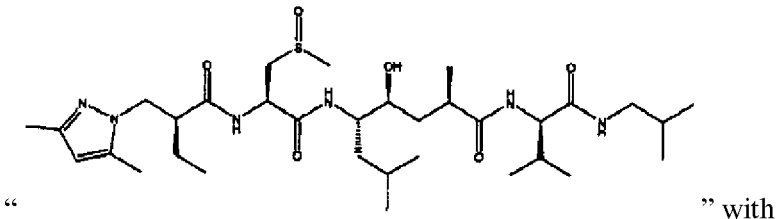 " with

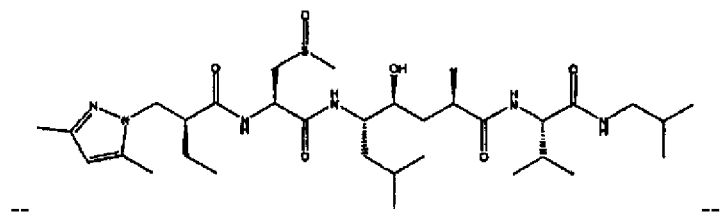

-- 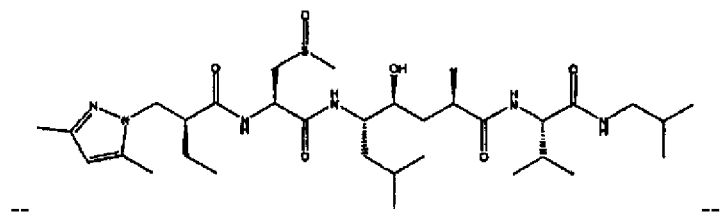 --

• In column 65-66, in Table 1A-continued, in structures 12 and 13, please replace

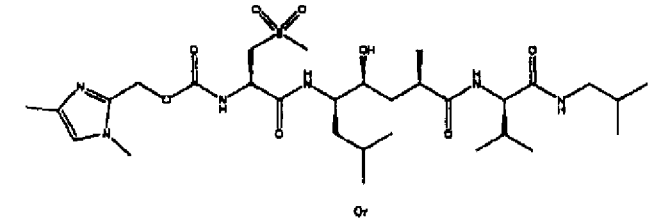

or

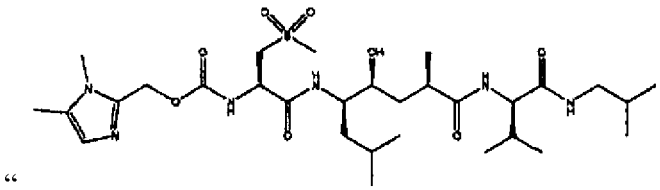

" 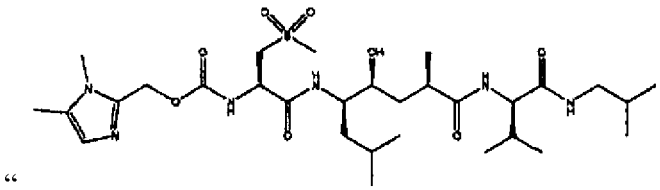 " with

UNITED STATES PATENT AND TRADEMARK OFFICE
CERTIFICATE OF CORRECTION

PATENT NO. : 7,335,632 B2  Page 7 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

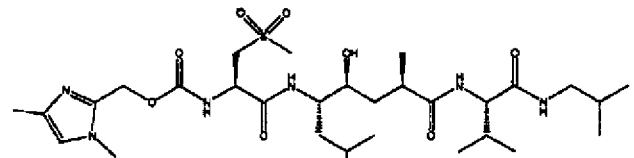

or

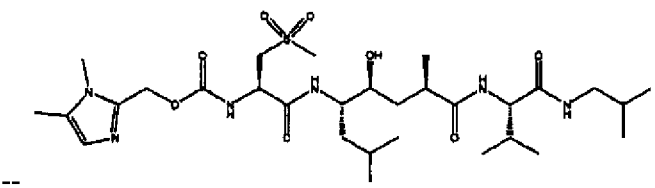

-- --

• In column 65-66, in Table 1A-continued, structure 14, please replace

"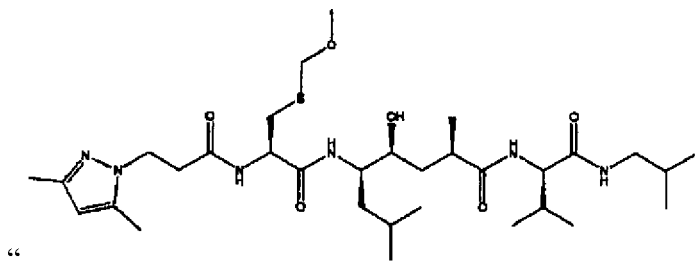" with

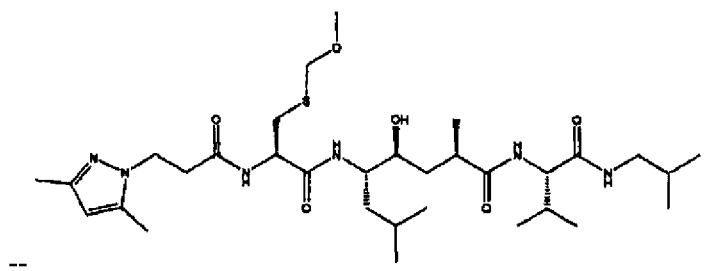

-- --

• In column 67-68, in Table 1A-continued, structure 15, please replace

UNITED STATES PATENT AND TRADEMARK OFFICE
CERTIFICATE OF CORRECTION

PATENT NO. : 7,335,632 B2  Page 8 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

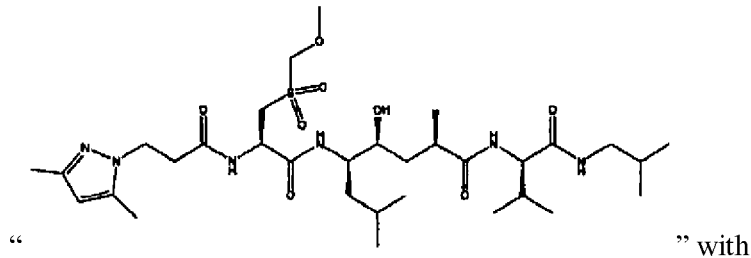

" " with

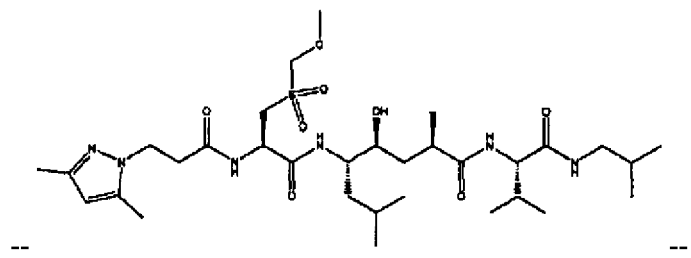

--   --

• In column 67-68, in Table 1A-continued, structure 16, please replace

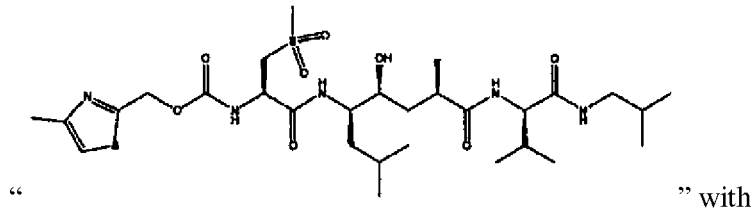

" " with

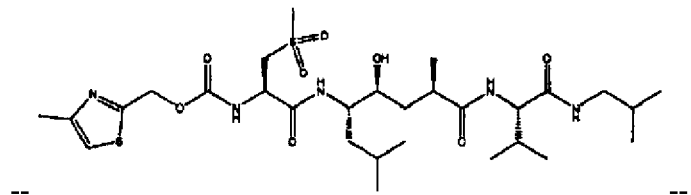

--   --

• In column 67-68, in Table 1A-continued, structure 17, please replace

UNITED STATES PATENT AND TRADEMARK OFFICE
CERTIFICATE OF CORRECTION

PATENT NO. : 7,335,632 B2  Page 9 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

"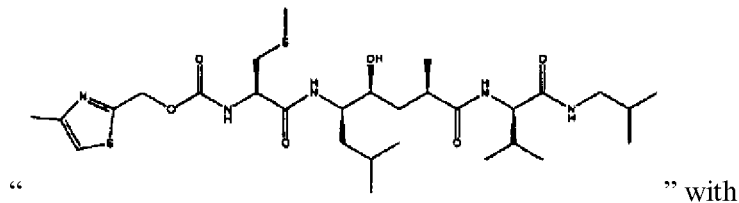" with

"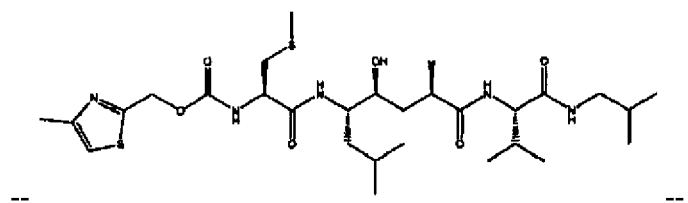" --

- In column 67-68, in Table 1A-continued, structure 18, please replace

"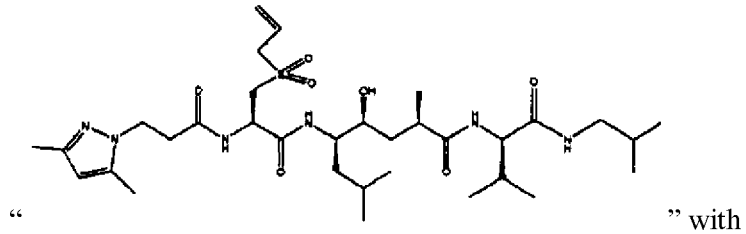" with

"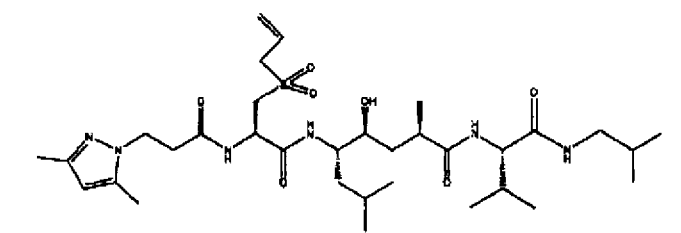" --

- In column 69-70, in Table 1A-continued, structure 19, please replace

UNITED STATES PATENT AND TRADEMARK OFFICE
CERTIFICATE OF CORRECTION

PATENT NO. : 7,335,632 B2  Page 10 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

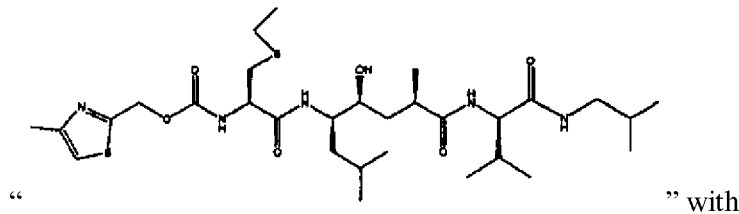
" " with

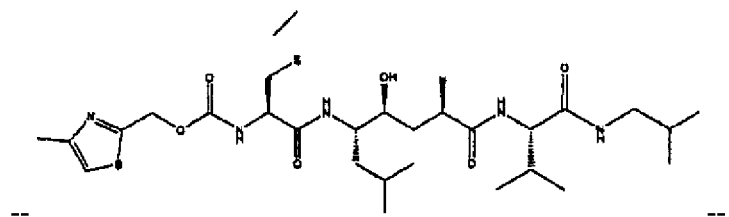
--  --

- In column 69-70, in Table 1A-continued, structure 20, please replace

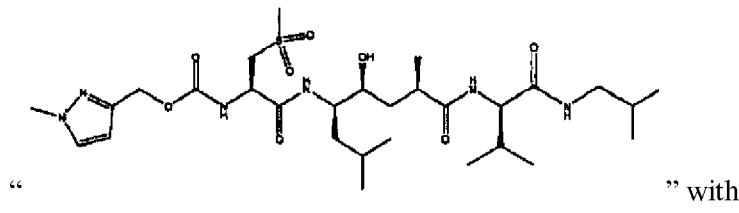
" " with

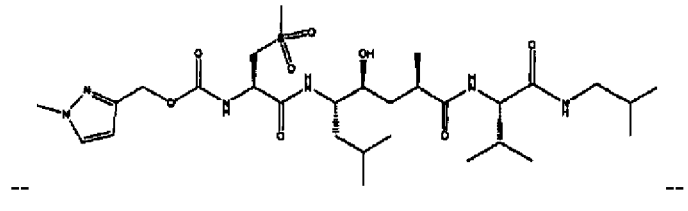
--  --

- In column 69-70, in Table 1A-continued, structure 21, please replace

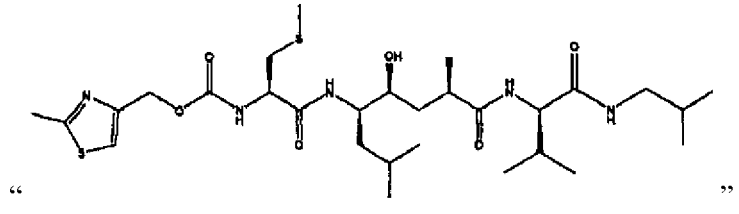
" " with

UNITED STATES PATENT AND TRADEMARK OFFICE
CERTIFICATE OF CORRECTION

PATENT NO.        : 7,335,632 B2
APPLICATION NO.   : 10/944117
DATED             : February 26, 2008
INVENTOR(S)       : Arun K. Ghosh et al.

It is certified that error appears in the above-identified patent and that said Letters Patent is hereby corrected as shown below:

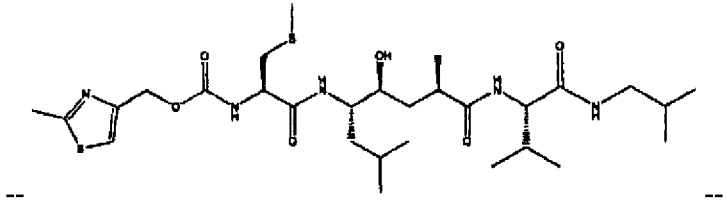
--                                                                   --

• In column 69-70, in Table 1A-continued, structure 22, please replace

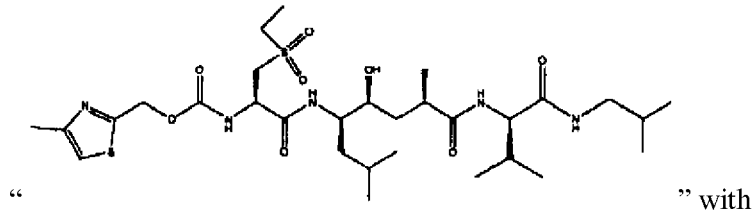
"                                                                   " with

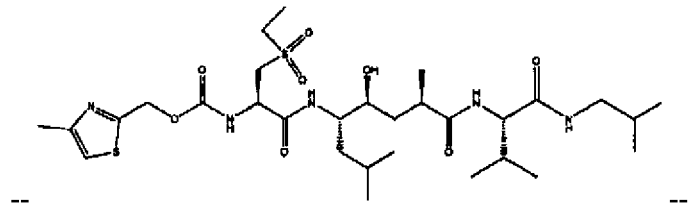
--                                                                   --

• In column 69-70, in Table 1A-continued, structure 23, please replace

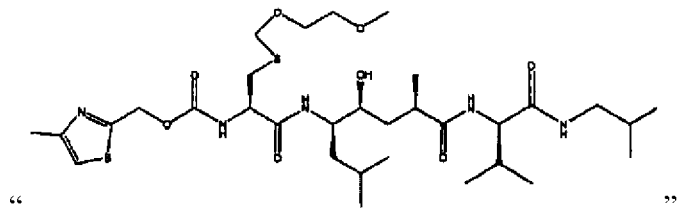
"                                                                   " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

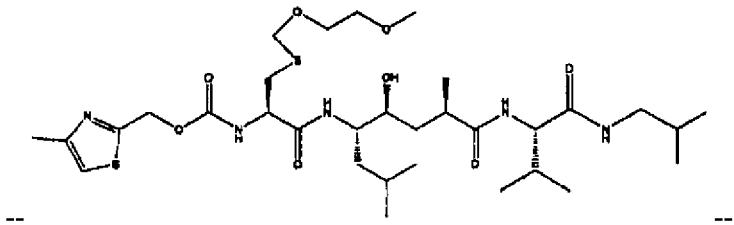

• In column 71-72, in Table 1A-continued, structure 24, please replace

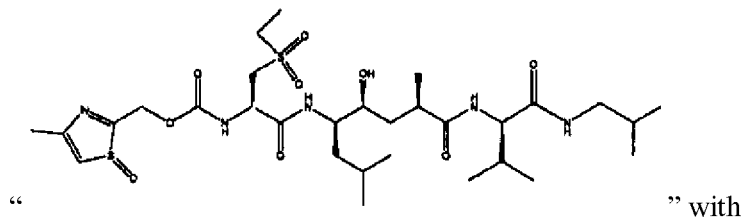

" " with

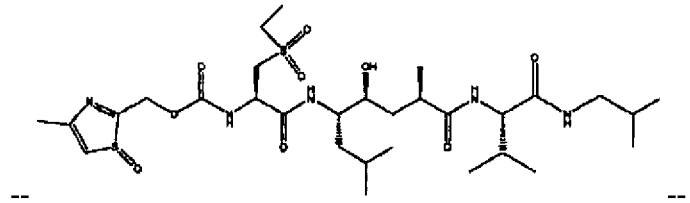

• In column 71-72, in Table 1A-continued, in structures 25 and 26, please replace

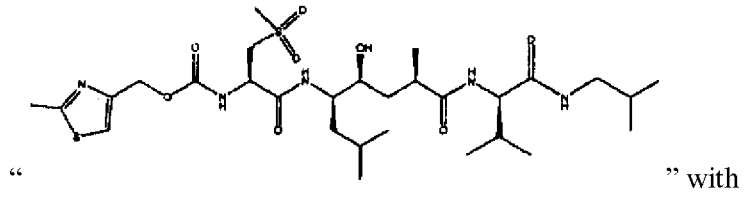

" " with

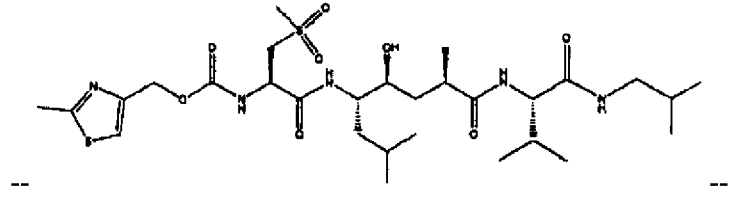

UNITED STATES PATENT AND TRADEMARK OFFICE
CERTIFICATE OF CORRECTION

PATENT NO. : 7,335,632 B2  Page 13 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

• In column 71-72, in Table 1A-continued, structure 27, please replace

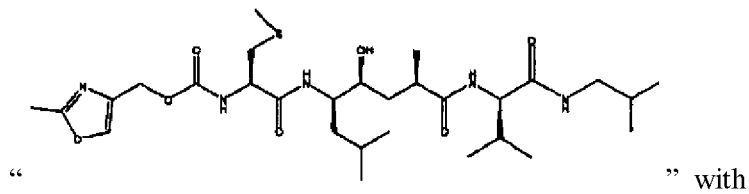

" " with

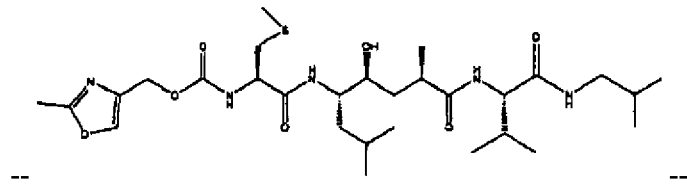

-- --

• In column 71-72, in Table 1A-continued, structure 28, please replace

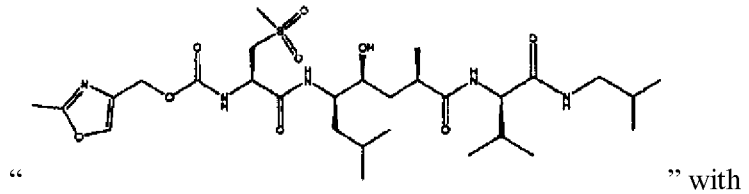

" " with

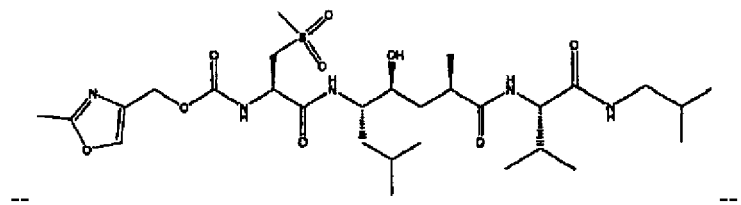

-- --

• In column 73-74, in Table 1A-continued, structure 29, please replace

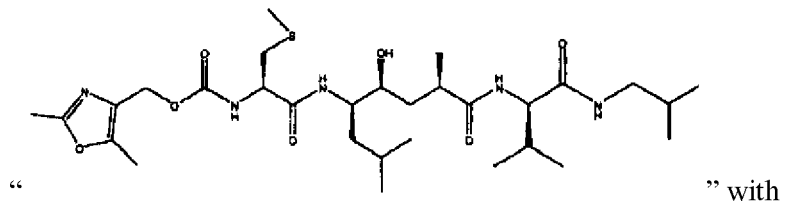

" " with

UNITED STATES PATENT AND TRADEMARK OFFICE
CERTIFICATE OF CORRECTION

PATENT NO. : 7,335,632 B2  Page 14 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

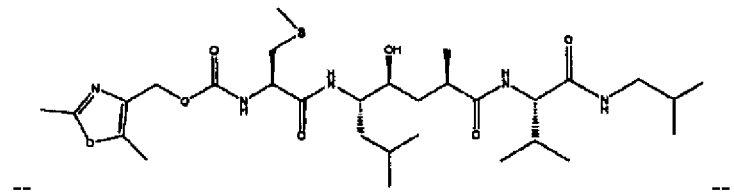

-- --

• In column 73-74, in Table 1A-continued, structure 30, please replace

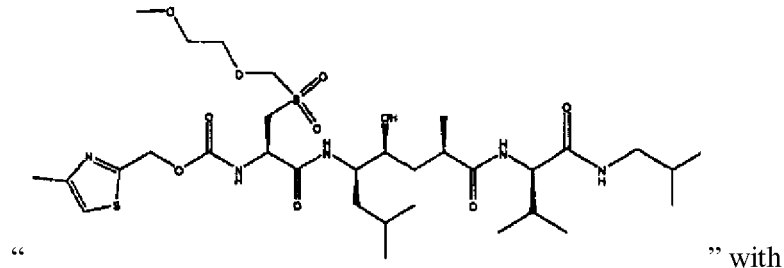

" " with

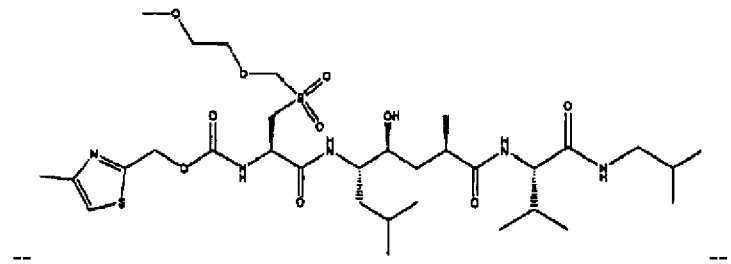

-- --

• In column 73-74, in Table 1A-continued, structure 31, please replace

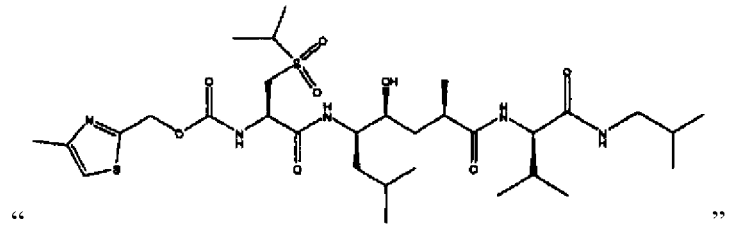

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

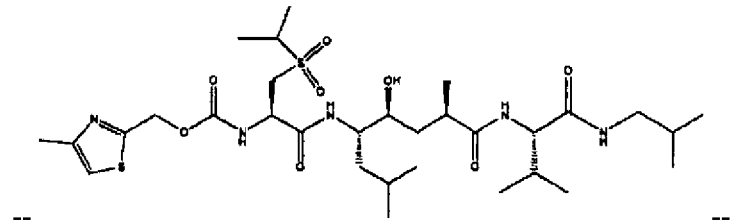

--                                                                                                      --

• In column 73-74, in Table 1A-continued, structure 32, please replace

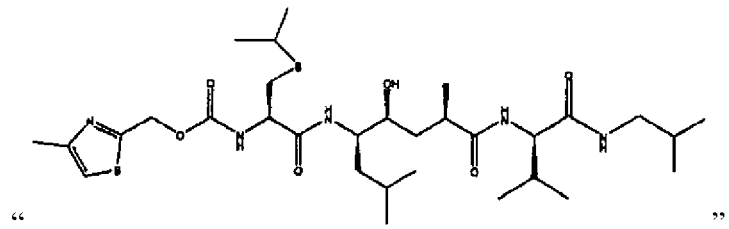

"                                                                                                      " with

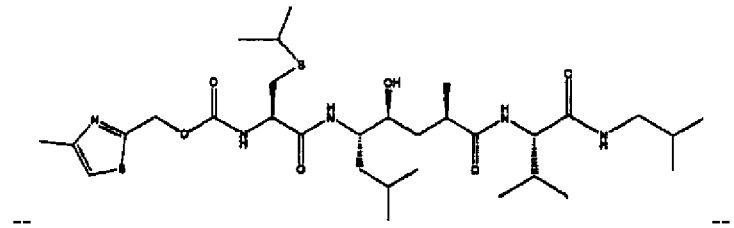

--                                                                                                      --

• In column 75-76, in Table 1A-continued, structure 33, please replace

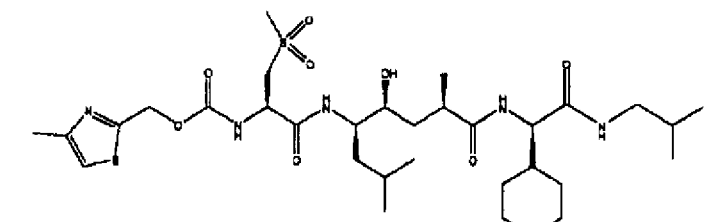

"                                                                                                      " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

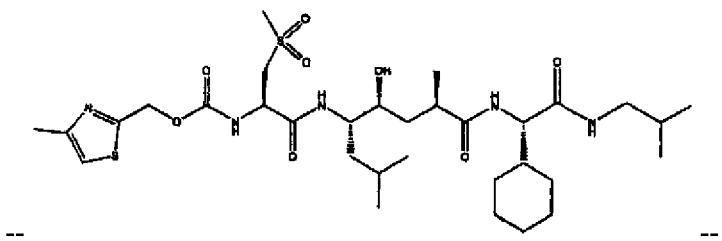

-- --

• In column 75-76, in Table 1A-continued, structure 34, please replace

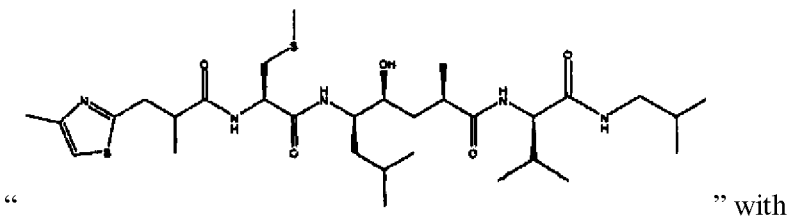

" " with

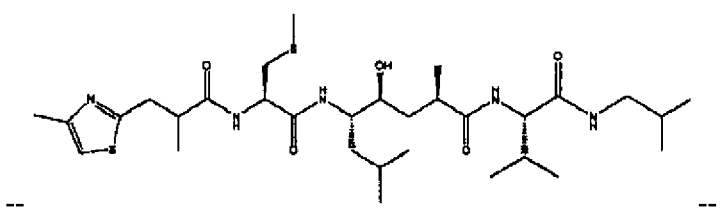

-- --

• In column 75-76, in Table 1A-continued, structure 35, please replace

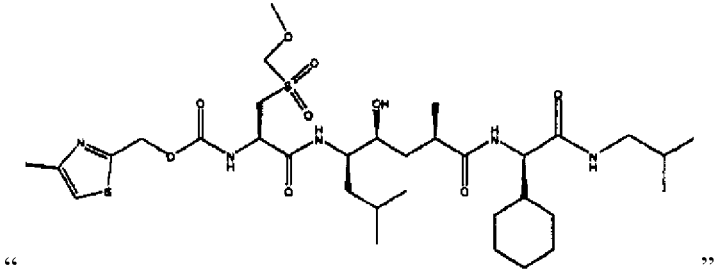

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

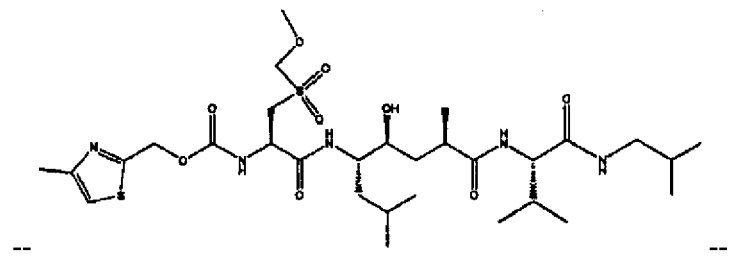

• In column 75-76, in Table 1A-continued, structure 36, please replace

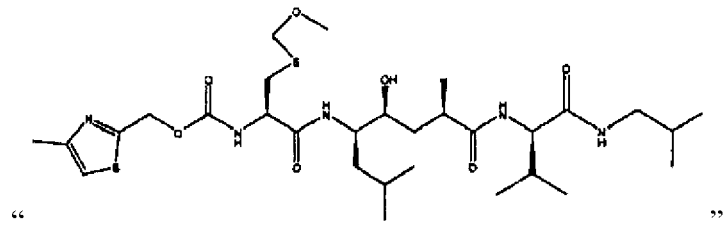

" " with

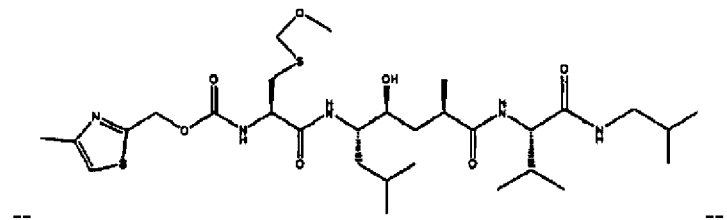

• In column 77-78, in Table 1A-continued, structure 37, please replace

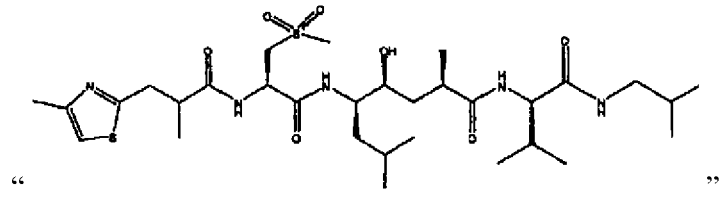

" " with

UNITED STATES PATENT AND TRADEMARK OFFICE
CERTIFICATE OF CORRECTION

PATENT NO. : 7,335,632 B2  Page 18 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

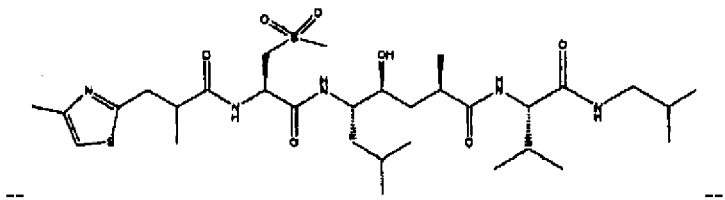

• In column 77-78, in Table 1A-continued, structure 38, please replace

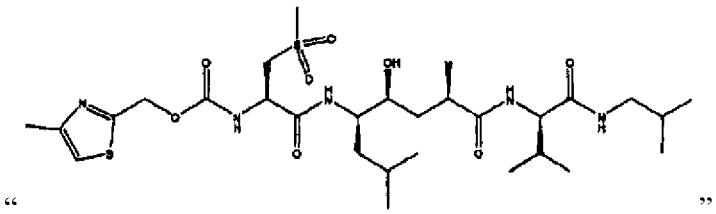

" with

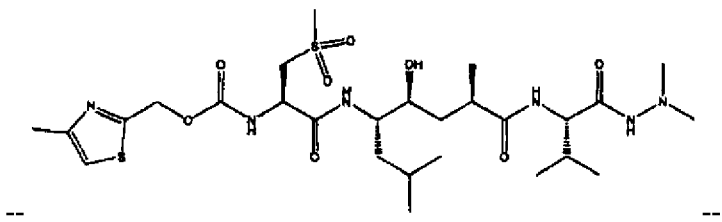

--

• In column 77-78, in Table 1A-continued, structure 39, please replace

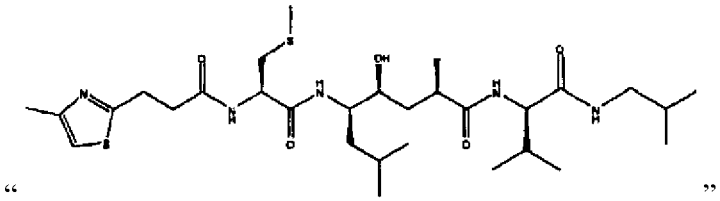

" with

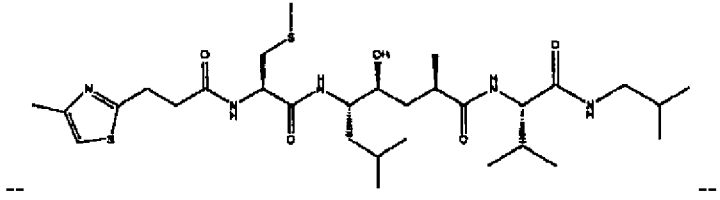

--

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

• In column 77-78, in Table 1A-continued, structure 40, please replace

"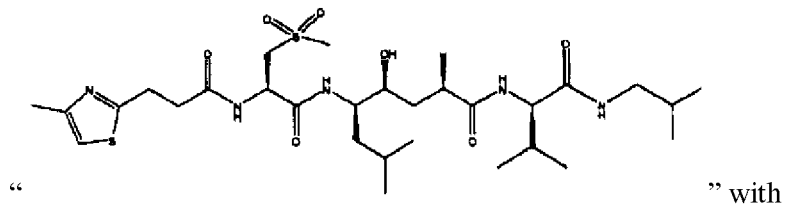" with

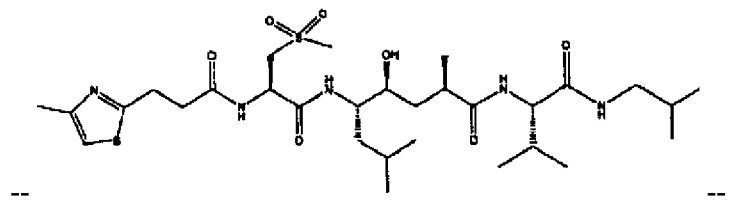
--                                                                --

• In column 77-78, in Table 1A-continued, structure 41, please replace

"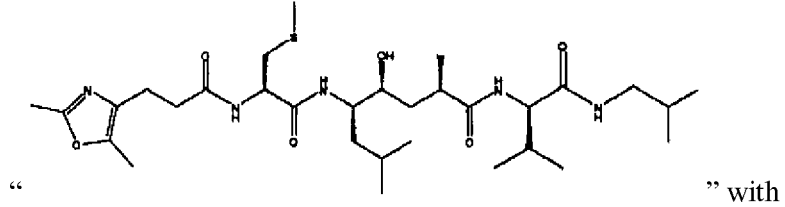" with

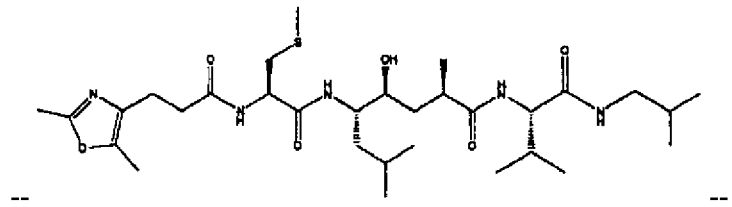
--                                                                --

• In column 79-80, in Table 1A-continued, structure 42, please replace

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

" 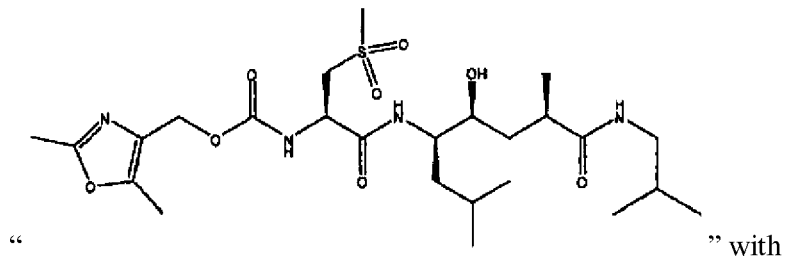 " with

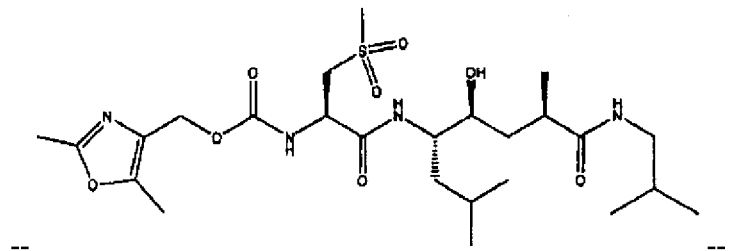

--  --

• In column 79-80, in Table 1A-continued, structure 43, please replace

" 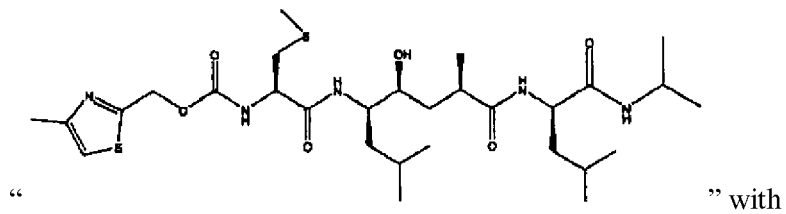 " with

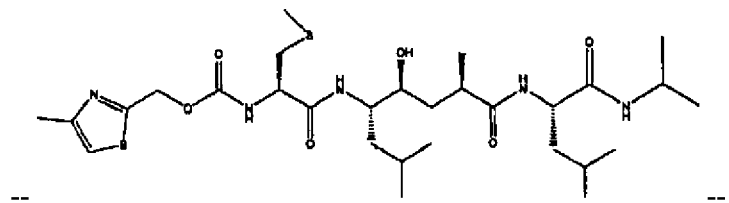

--  --

• In column 79-80, in Table 1A-continued, structure 44, please replace

UNITED STATES PATENT AND TRADEMARK OFFICE
CERTIFICATE OF CORRECTION

PATENT NO. : 7,335,632 B2 Page 21 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

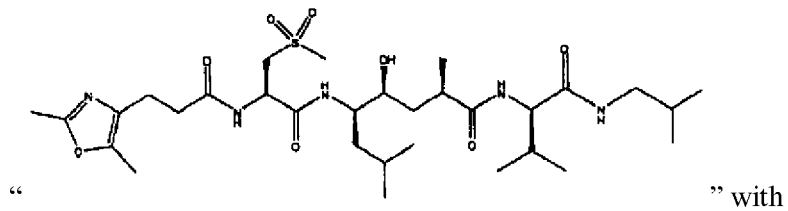

" " with

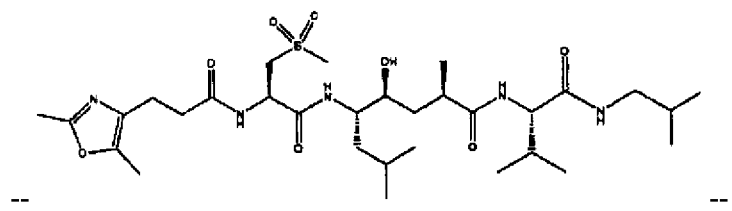

-- --

• In column 79-80, in Table 1A-continued, structure 45, please replace

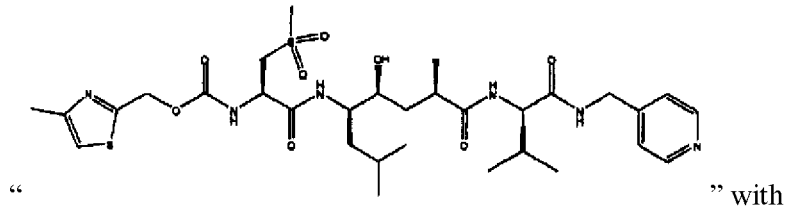

" " with

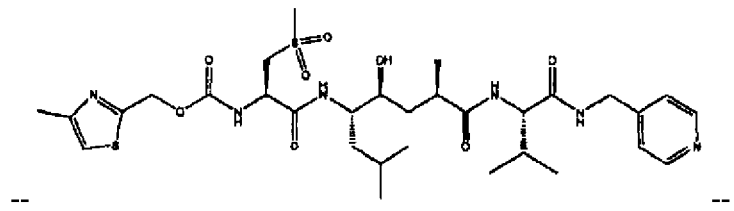

-- --

• In column 79-80, in Table 1A-continued, structure 46, please replace

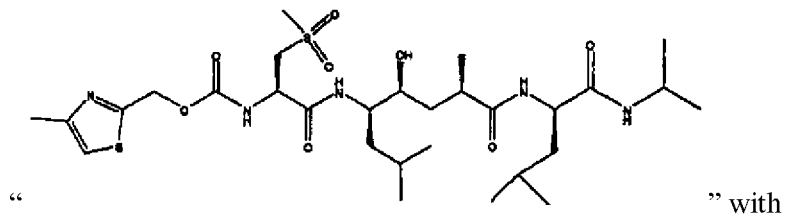

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

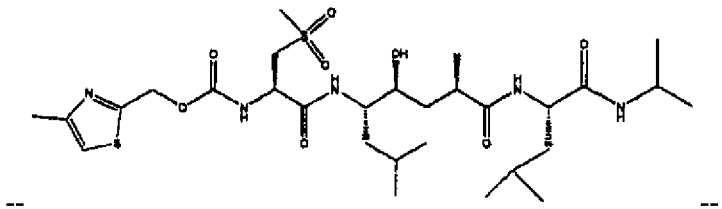

• In column 81-82, in Table 1A-continued, structure 47, please replace

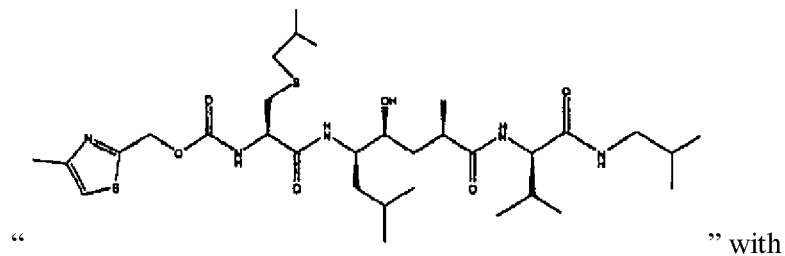

" " with

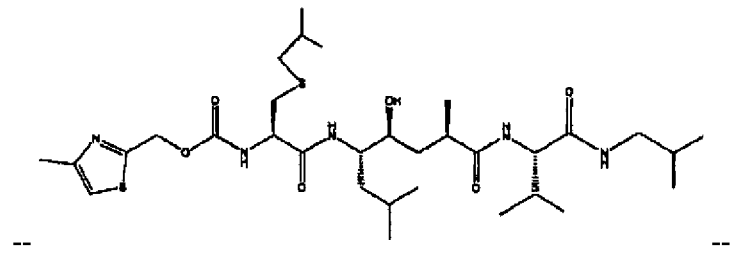

• In column 81-82, in Table 1A-continued, structure 48, please replace

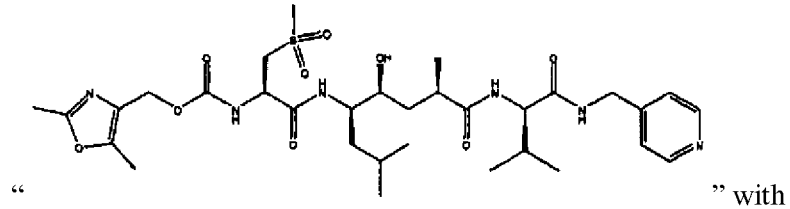

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

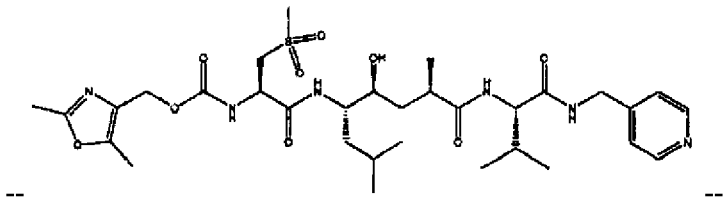
--                                                                                        --

• In column 81-82, in Table 1A-continued, structure 49, please replace

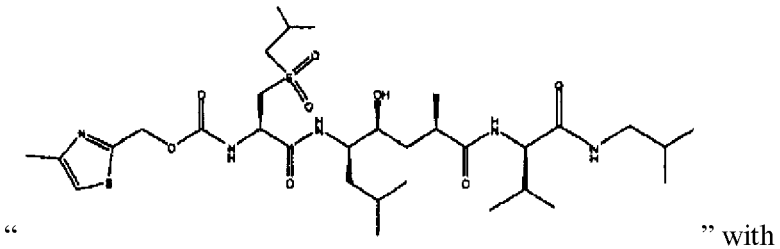
"                                                                                        " with

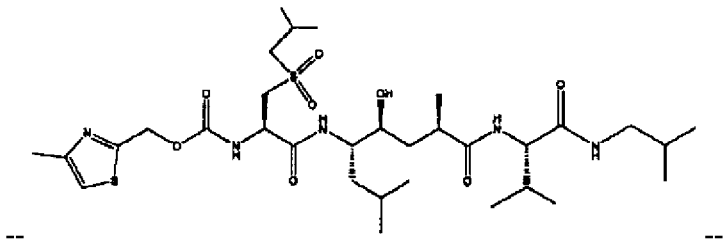
--                                                                                        --

• In column 81-82, in Table 1A-continued, structure 50, please replace

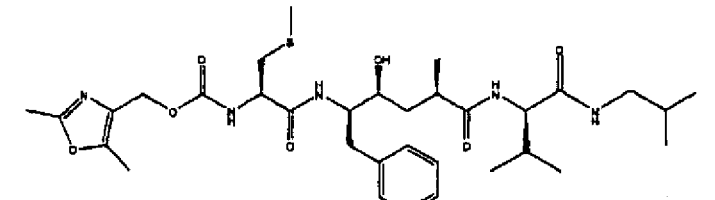
"                                                                                        " with

UNITED STATES PATENT AND TRADEMARK OFFICE
CERTIFICATE OF CORRECTION

PATENT NO.       : 7,335,632 B2                    Page 24 of 44
APPLICATION NO.  : 10/944117
DATED            : February 26, 2008
INVENTOR(S)      : Arun K. Ghosh et al.

It is certified that error appears in the above-identified patent and that said Letters Patent is hereby corrected as shown below:

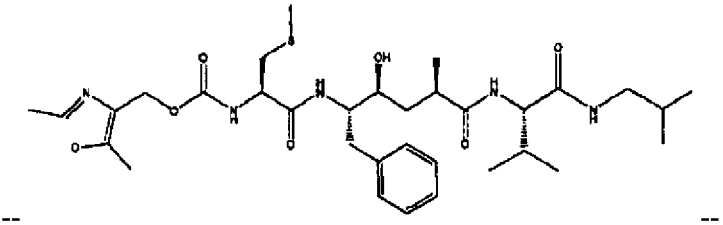

-- --

• In column 83-84, in Table 1A-continued, structure 51, please replace

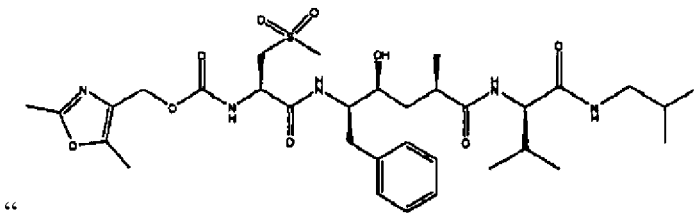

" " with

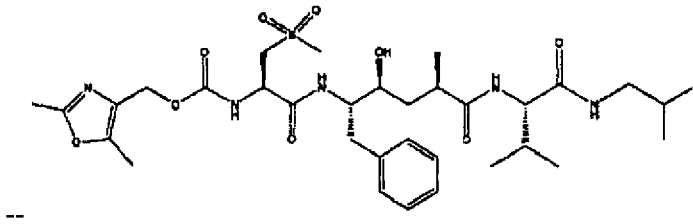

-- --

• In column 83-84, in Table 1A-continued, structure 52, please replace

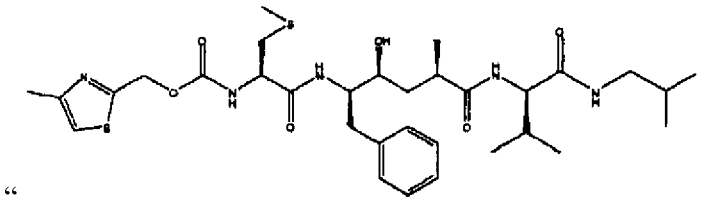

" " with

UNITED STATES PATENT AND TRADEMARK OFFICE
CERTIFICATE OF CORRECTION

PATENT NO.       : 7,335,632 B2
APPLICATION NO.  : 10/944117
DATED            : February 26, 2008
INVENTOR(S)      : Arun K. Ghosh et al.

It is certified that error appears in the above-identified patent and that said Letters Patent is hereby corrected as shown below:

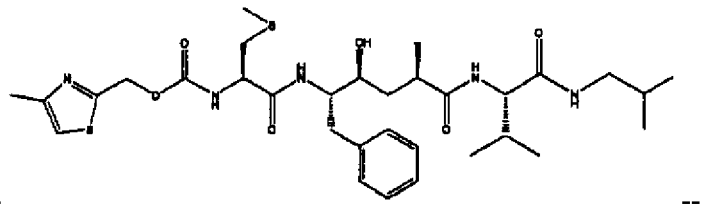

-- --

• In column 83-84, in Table 1A-continued, structure 53, please replace

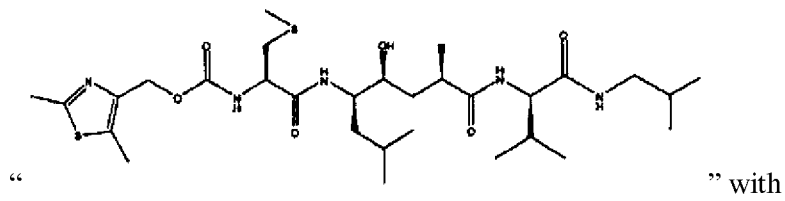

" " with

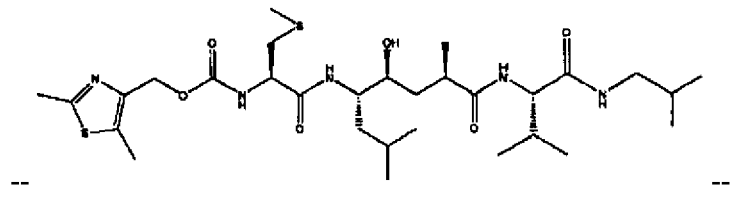

-- --

• In column 83-84, in Table 1A-continued, structure 54, please replace

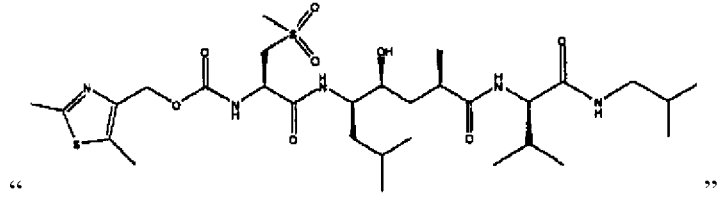

" " with

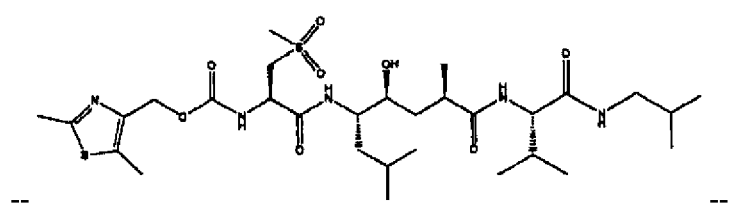

-- --

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

• In column 83-84, in Table 1A-continued, structure 55, please replace

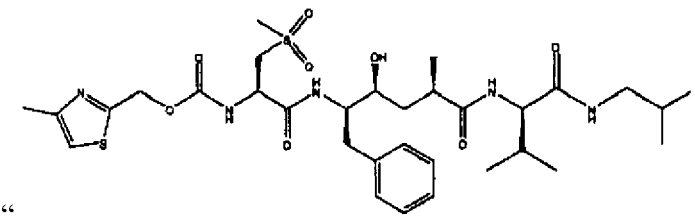

" " with

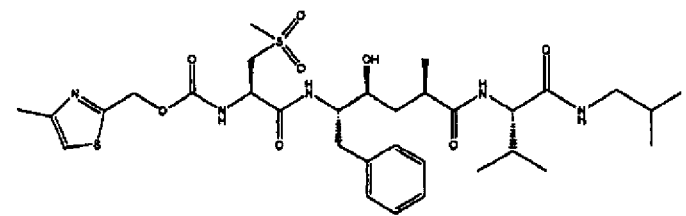

-- --

• In column 85-86, in Table 1A-continued, structure 56, please replace

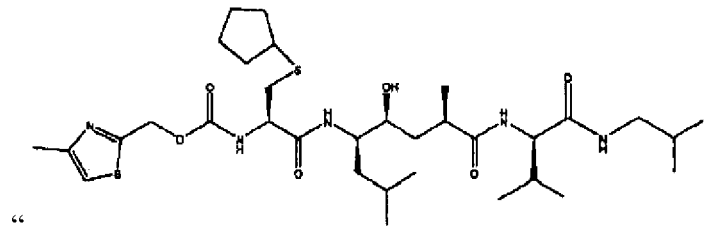

" " with

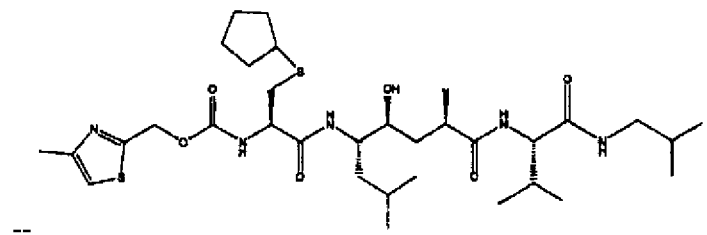

-- --

• In column 85-86, in Table 1A-continued, structure 57, please replace

UNITED STATES PATENT AND TRADEMARK OFFICE
CERTIFICATE OF CORRECTION

PATENT NO. : 7,335,632 B2 Page 27 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

" 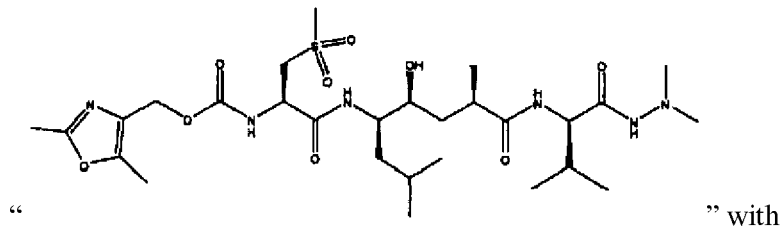 " with

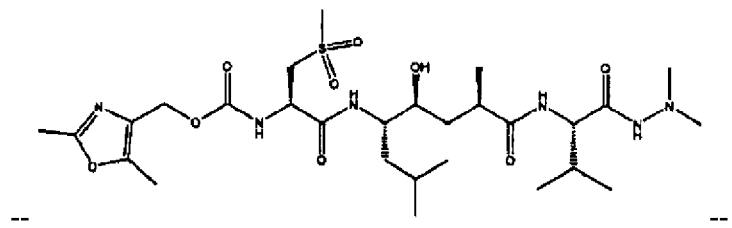

-- --

• In column 85-86, in Table 1A-continued, structure 58, please replace

" 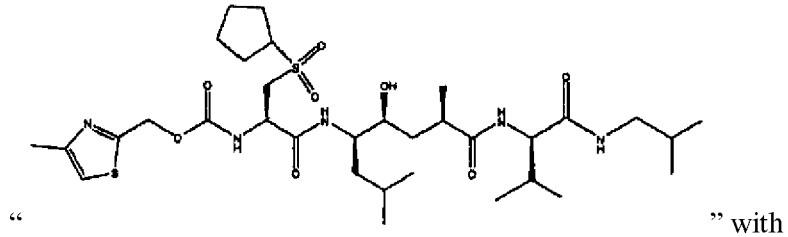 " with

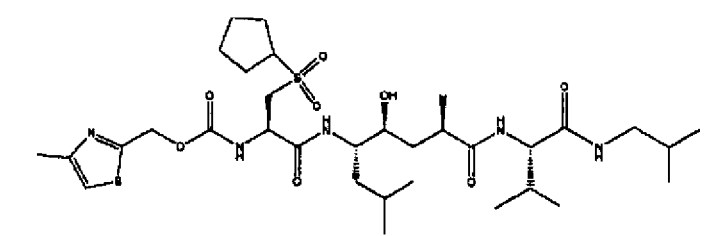

-- --

• In column 85-86, in Table 1A-continued, structure 59, please replace

UNITED STATES PATENT AND TRADEMARK OFFICE
CERTIFICATE OF CORRECTION

PATENT NO. : 7,335,632 B2 Page 28 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

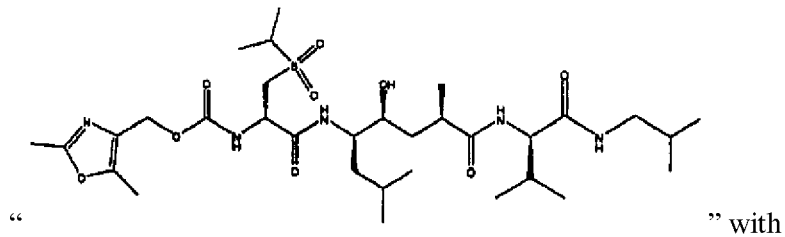

"                                                                    " with

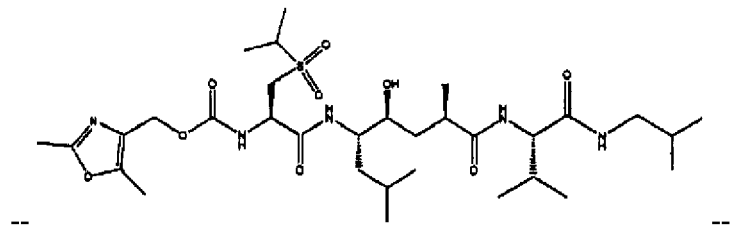

--                                                                        --

• In column 87-88, in Table 1A-continued, structure 60, please replace

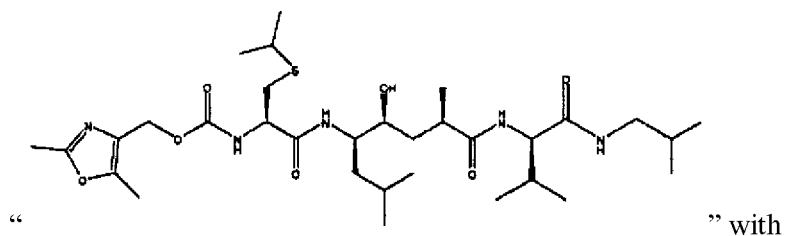

"                                                                    " with

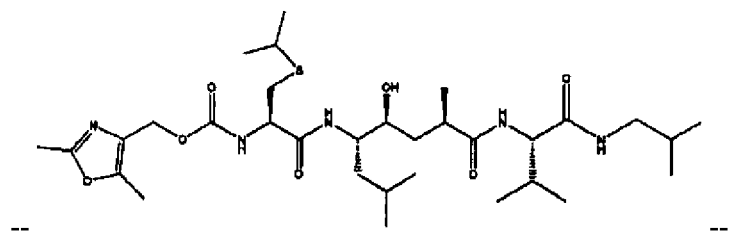

--                                                                        --

• In column 87-88, in Table 1A-continued, structure 61, please replace

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

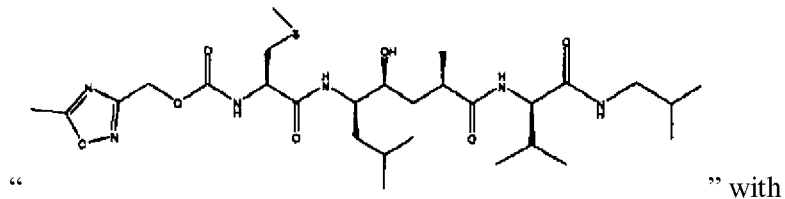

" " with

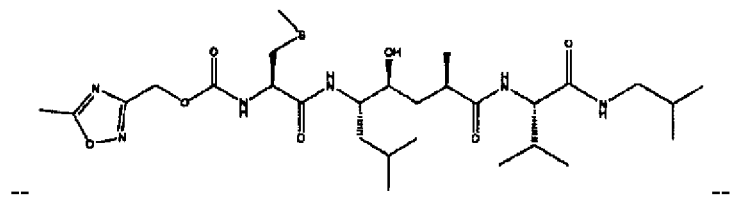

-- --

• In column 87-88, in Table 1A-continued, structure 62, please replace

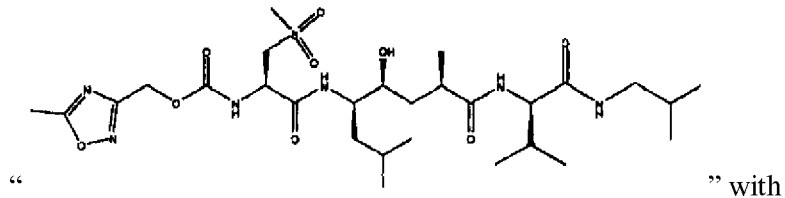

" " with

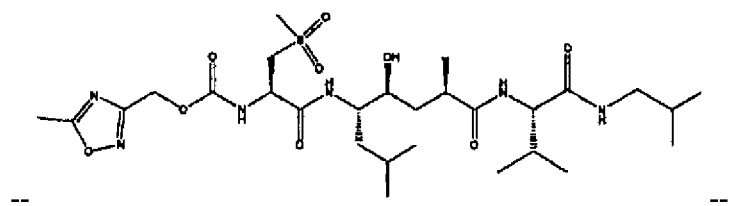

-- --

• In column 87-88, in Table 1A-continued, structure 64, please replace

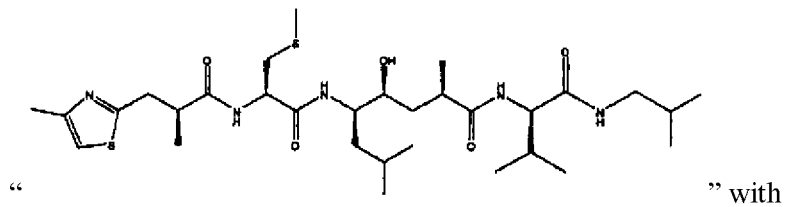

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

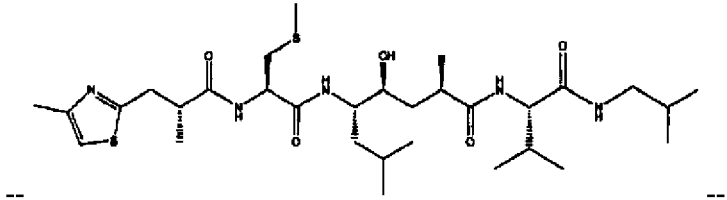
--                                                                                 --

• In column 89-90, in Table 1A-continued, structure 65, please replace

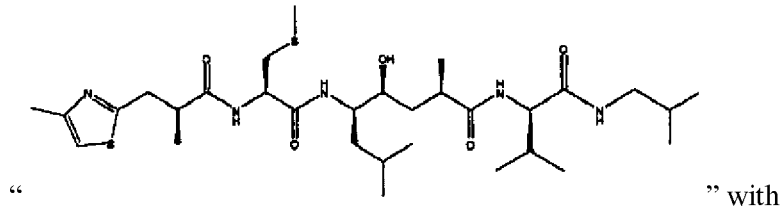
"                                                                                 " with

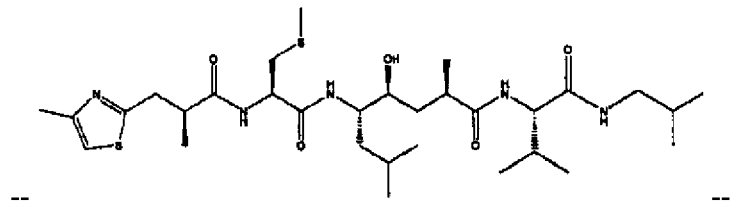
--                                                                                 --

• In column 89-90, in Table 1A-continued, structure 66, please replace

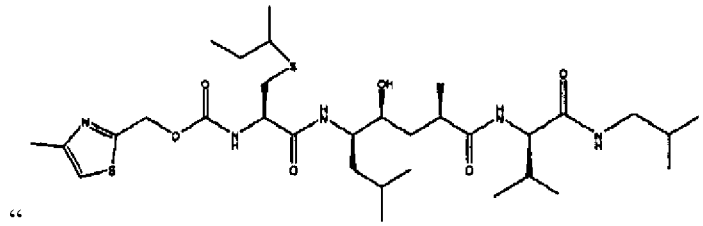
"                                                                                 " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

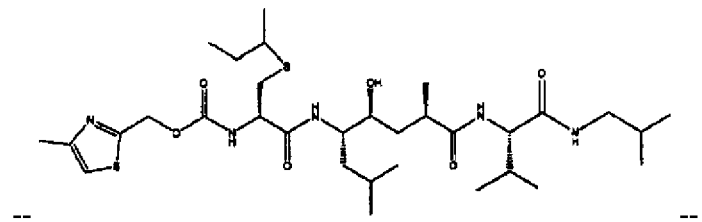

• In column 89-90, in Table 1A-continued, structure 67, please replace

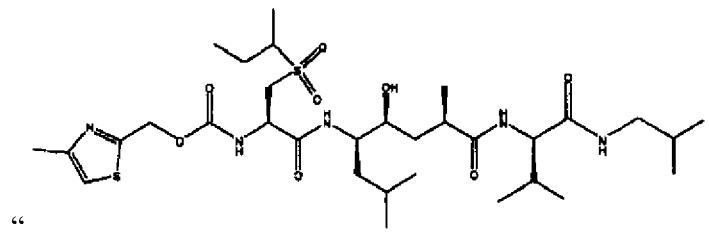

" with

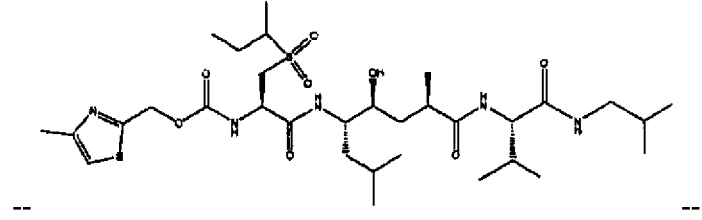

• In column 89-90, in Table 1A-continued, structure 68, please replace

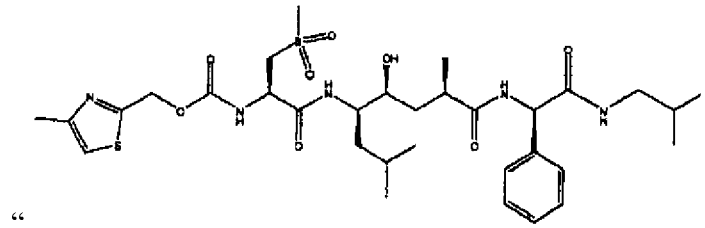

" with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

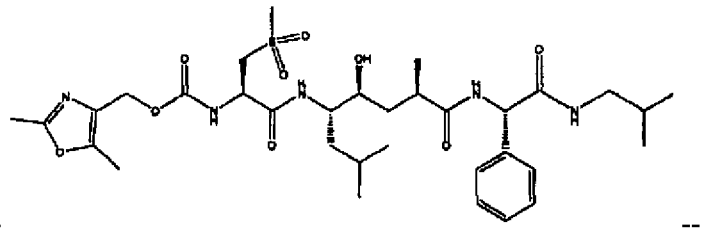

--                                                                      --

• In column 89-90, in Table 1A-continued, structure 69, please replace

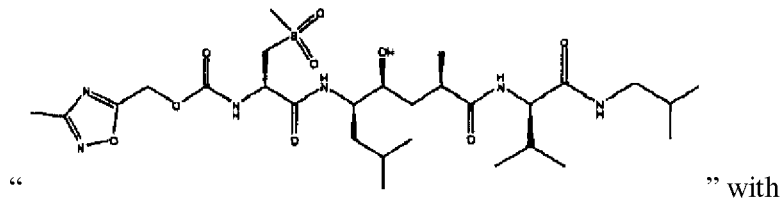

"                                                                      " with

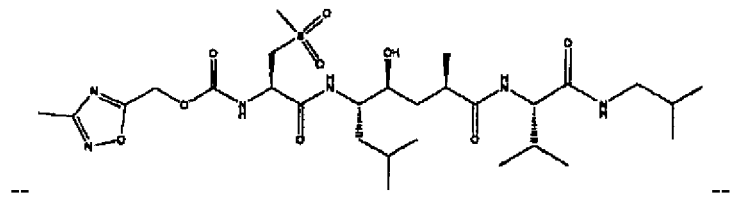

--                                                                      --

• In column 91-92, in Table 1A-continued, structure 70, please replace

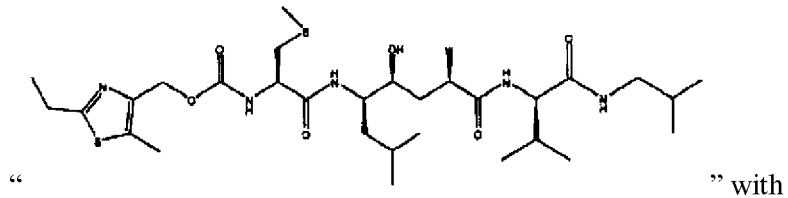

"                                                                      " with

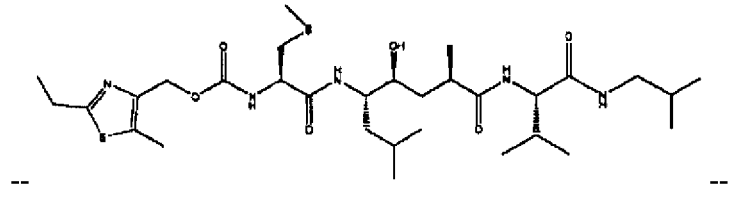

--                                                                      --

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

• In column 91-92, in Table 1A-continued, structure 71, please replace

"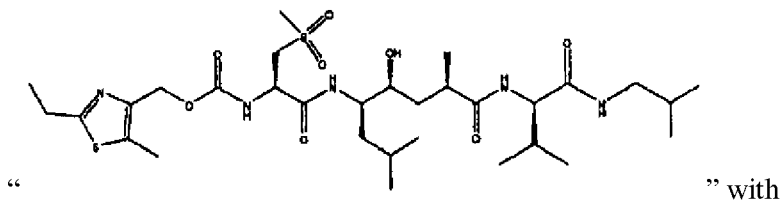" with

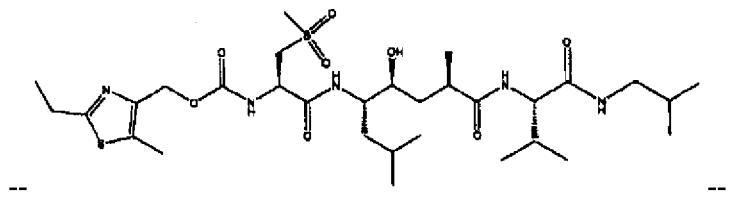

• In column 91-92, in Table 1A-continued, structure 72, please replace

"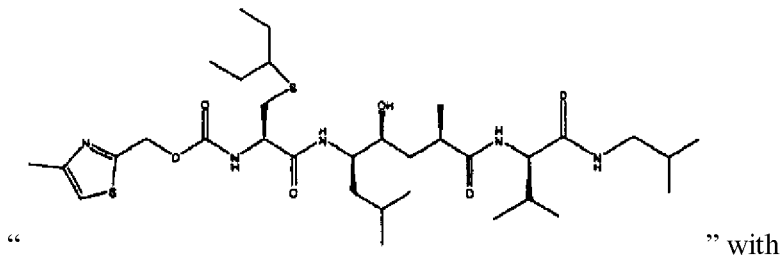" with

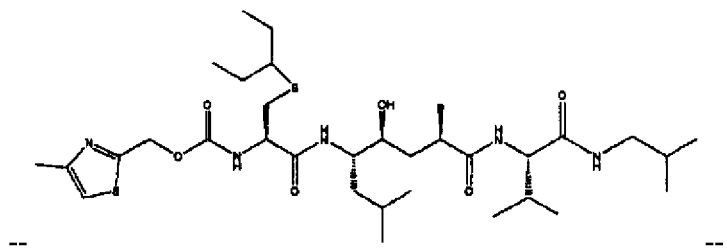

• In column 91-92, in Table 1A-continued, structure 73, please replace

UNITED STATES PATENT AND TRADEMARK OFFICE
CERTIFICATE OF CORRECTION

PATENT NO. : 7,335,632 B2 Page 34 of 44
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

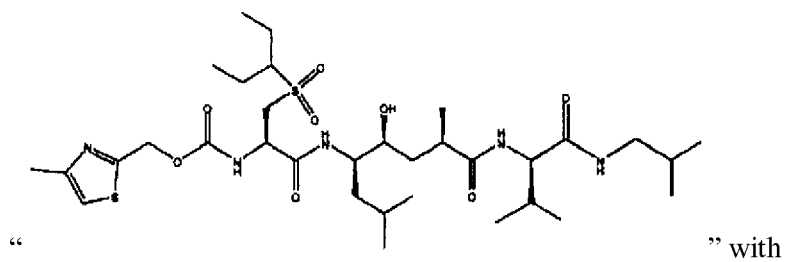

" " with

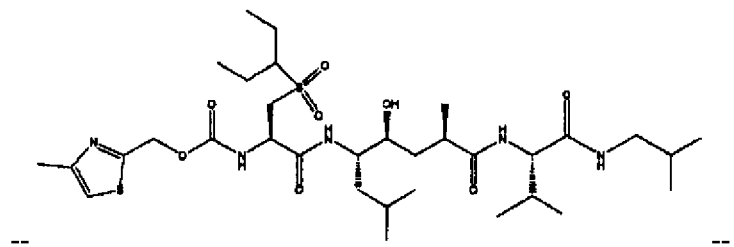

--  --

• In column 93-94, in Table 1A-continued, structure 74, please replace

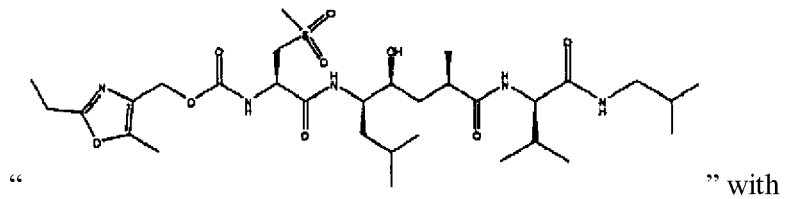

" " with

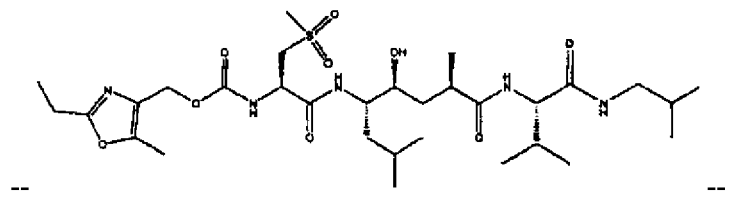

--  --

• In column 93-94, in Table 1A-continued, structure 75, please replace

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

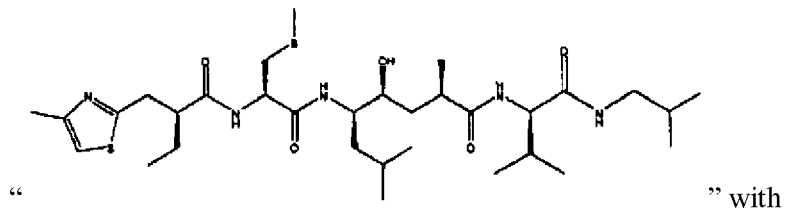

" " with

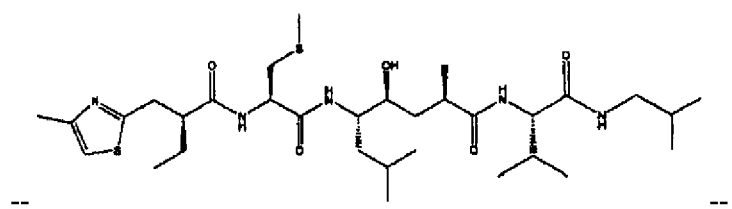

-- --

• In column 93-94, in Table 1A-continued, structure 76, please replace

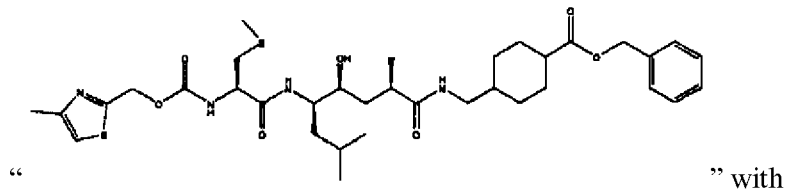

" " with

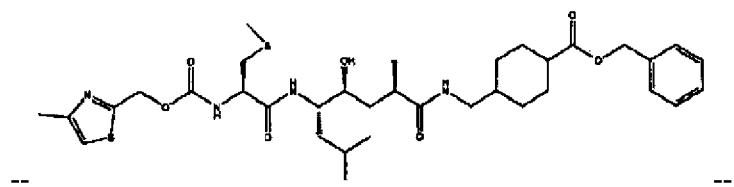

-- --

• In column 93-94, in Table 1A-continued, structure 77, please replace

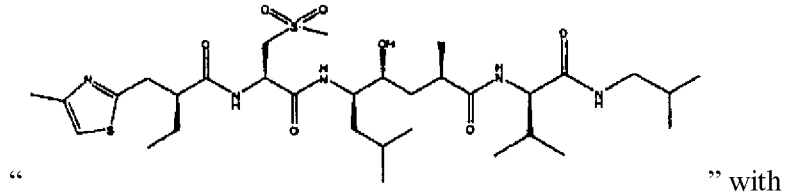

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

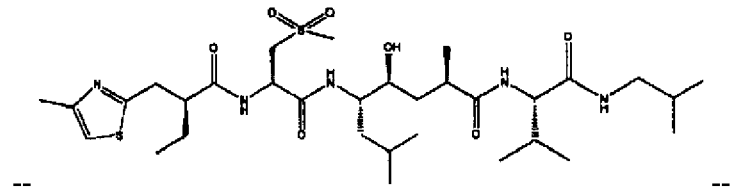

-- --

• In column 93-94, in Table 1A-continued, structure 78, please replace

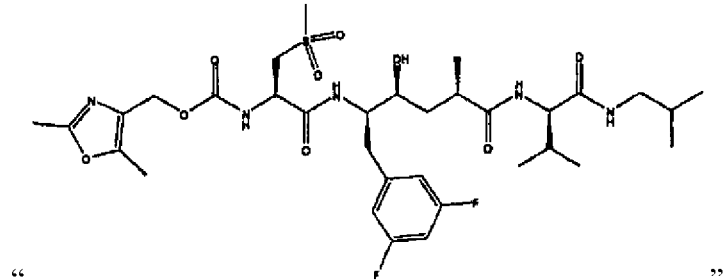

" " with

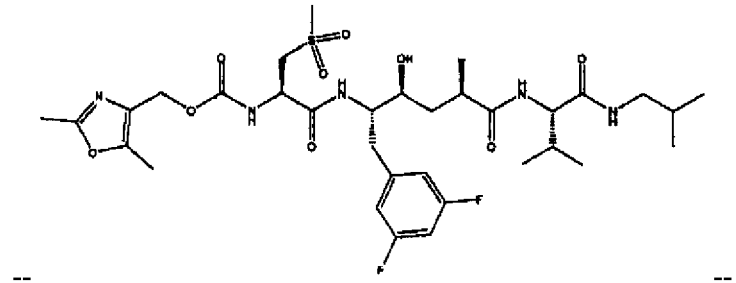

-- --

• In column 95-96, in Table 1A-continued, structure 79, please replace

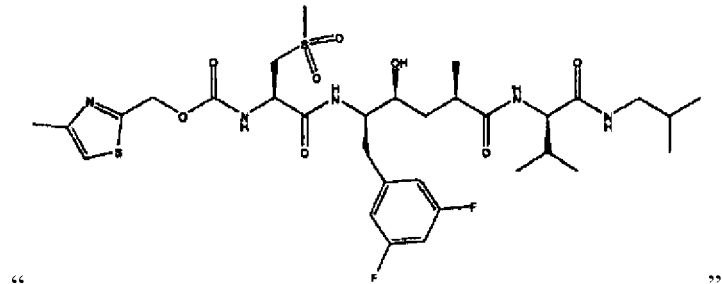

" " with

UNITED STATES PATENT AND TRADEMARK OFFICE
CERTIFICATE OF CORRECTION

PATENT NO.         : 7,335,632 B2                              Page 37 of 44
APPLICATION NO.    : 10/944117
DATED              : February 26, 2008
INVENTOR(S)        : Arun K. Ghosh et al.

It is certified that error appears in the above-identified patent and that said Letters Patent is hereby corrected as shown below:

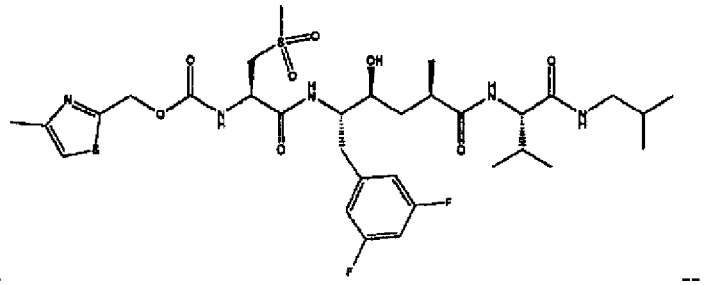

-- --

• In column 95-96, in Table 1A-continued, structure 80, please replace

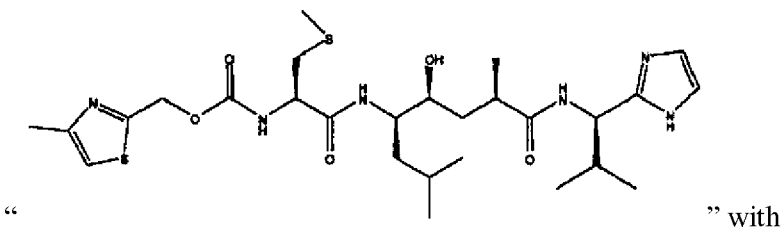

" " with

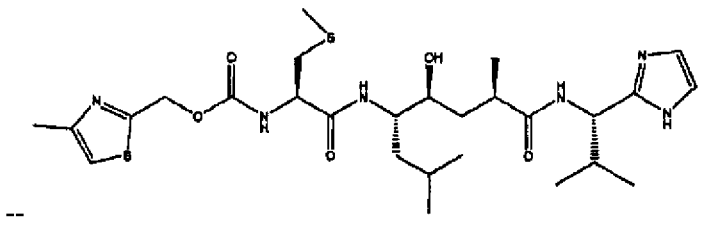

-- --

• In column 95-96, in Table 1A-continued, structure 81, please replace

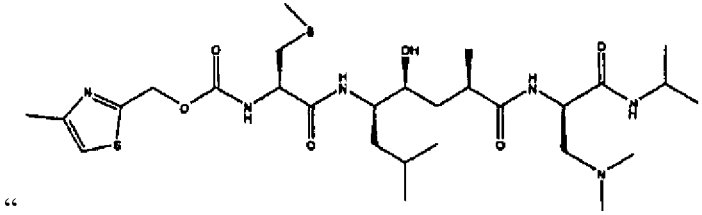

" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

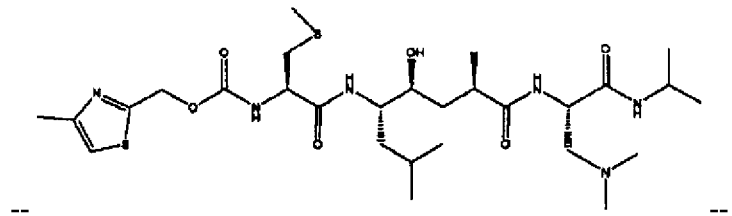

-- --

• In column 95-96, in Table 1A-continued, structure 82, please replace

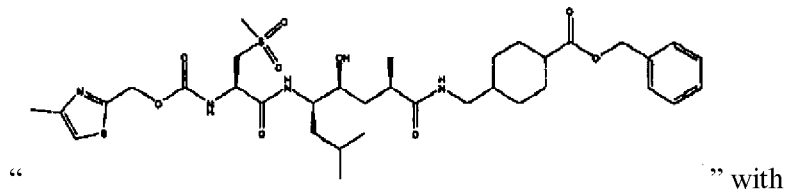

" " with

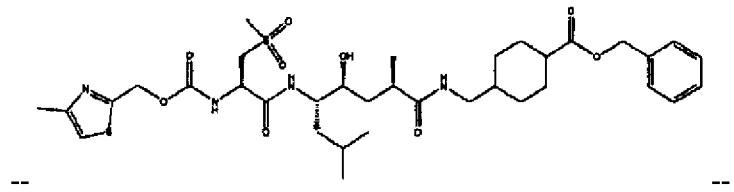

-- --

• In column 97-98, in Table 1A-continued, structure 84, please replace

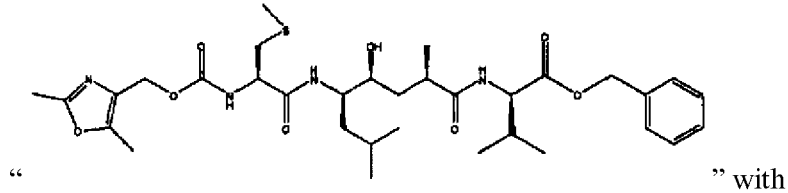

" " with

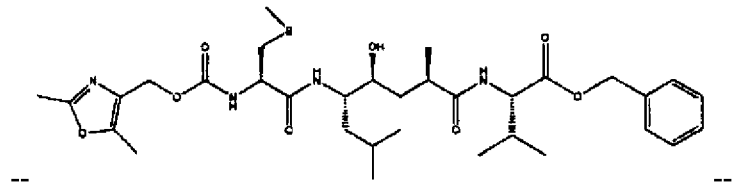

-- --

• In column 97-98, in Table 1A-continued, structure 85, please replace

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

Page 39 of 44

It is certified that error appears in the above-identified patent and that said Letters Patent is hereby corrected as shown below:

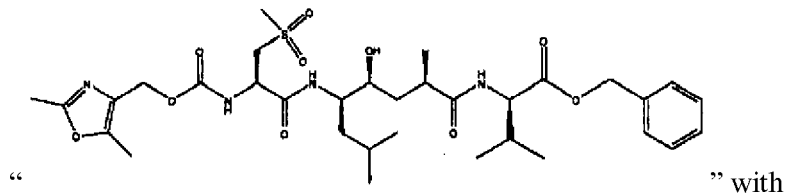
" " with

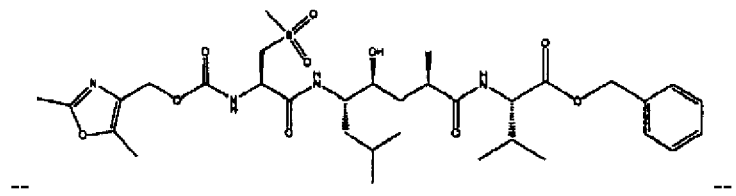
-- --

• In column 97-98, in Table 1A-continued, structure 86, please replace

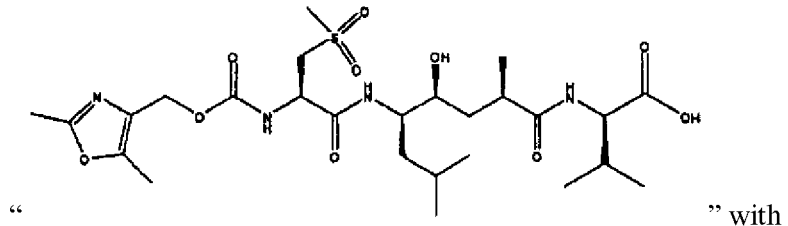
" " with

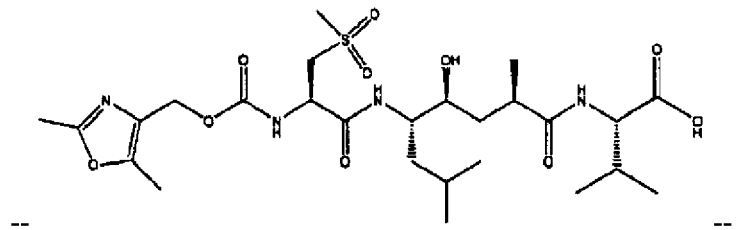
-- --

• In column 97-98, in Table 1A-continued, structure 87, please replace

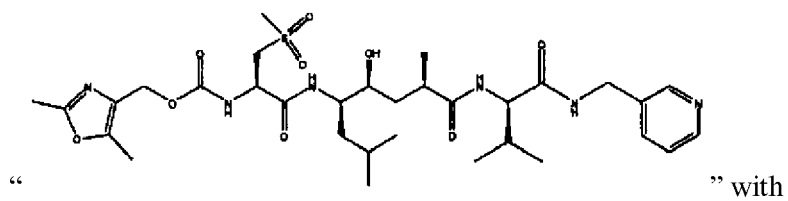
" " with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

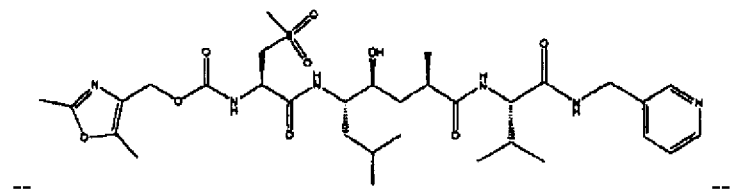

• In column 97-98, in Table 1A-continued, structure 88, please replace

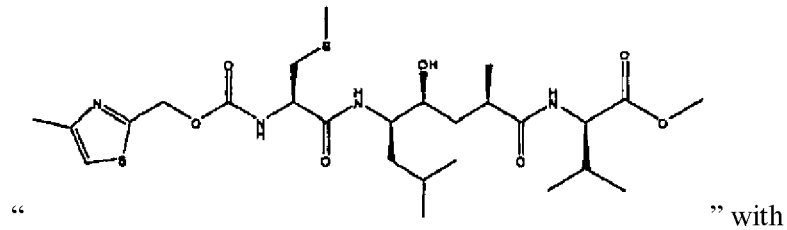

" with

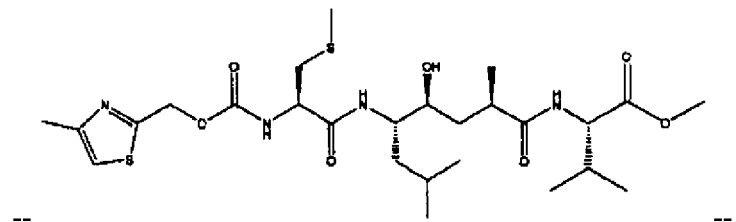

"

• In column 99-100, in Table 1A-continued, structure 89, please replace

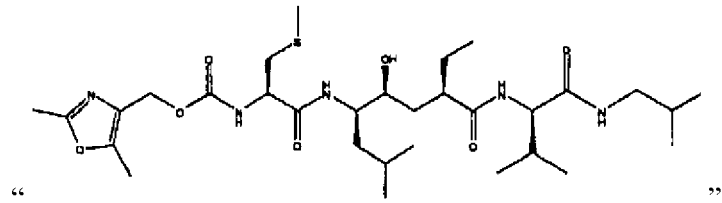

" with

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

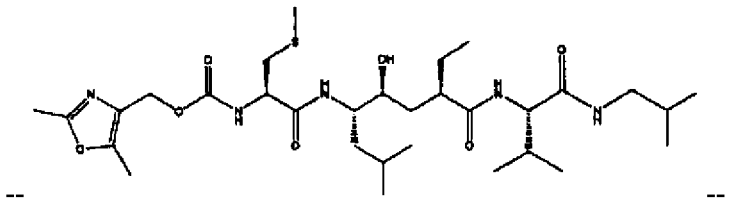

--  --

• In column 99-100, in Table 1A-continued, structure 90, please replace

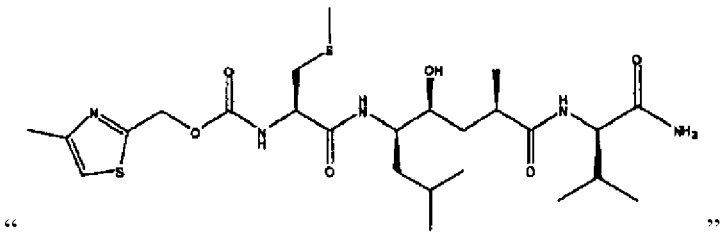

"  " with

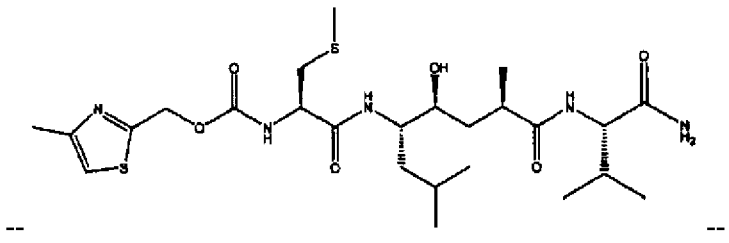

--  --

• In column 99-100, in Table 1A-continued, structure 91, please replace

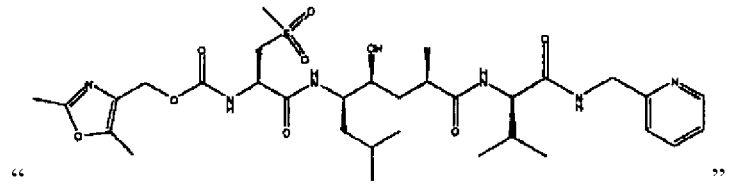

"  " with

UNITED STATES PATENT AND TRADEMARK OFFICE
CERTIFICATE OF CORRECTION

PATENT NO.       : 7,335,632 B2                                      Page 42 of 44
APPLICATION NO. : 10/944117
DATED            : February 26, 2008
INVENTOR(S)      : Arun K. Ghosh et al.

It is certified that error appears in the above-identified patent and that said Letters Patent is hereby corrected as shown below:

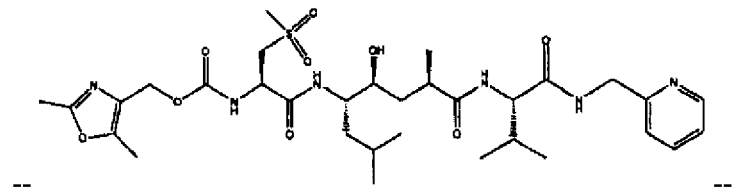

-- --

• In column 99-100, in Table 1A-continued, structure 92, please replace

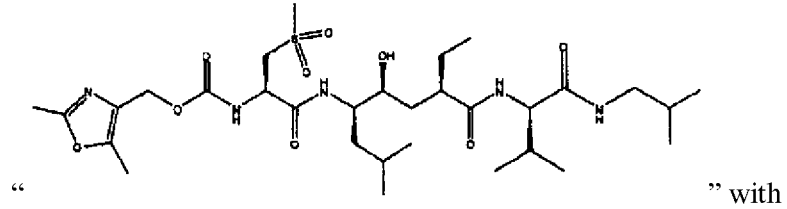

" " with

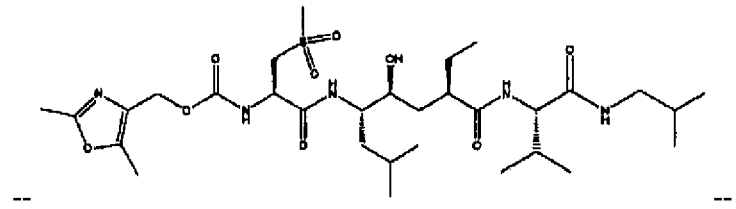

-- --

• In column 99-100, in Table 1A-continued, structure 93, please replace

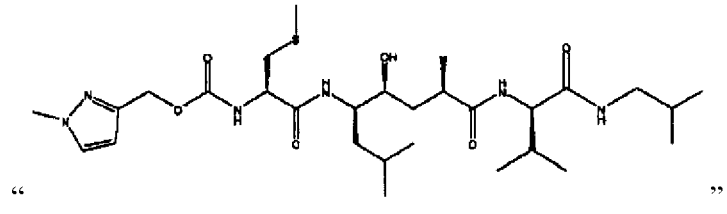

" " with

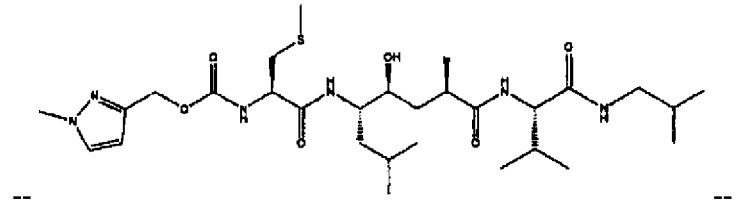

-- --

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

• In column 101-102, in Table 1A-continued, structure 94, please replace

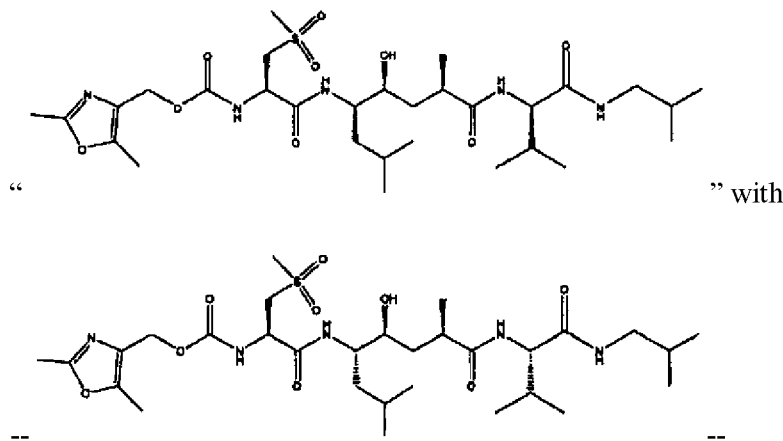

" " with " " --  --

*In the Claims*

• In Claim 1, column 106, line 6, please replace "$R_1$ is -$C_{15}R_{16}$, or -$OR_{15}$;" with --$R_1$ is -$CR_{15}R_{16}$, or -$OR_{15}$,--

• In Claim 1, column 106, line 8, please replace "$R_9$ and $R_{10}$ are each, independently, H, or aliphatic; and" with --$R_9$ and $R_{10}$ are each, independently, H, or an aliphatic; and--

• In Claim 1 column 106, line 36, please replace "dimethyi-" with --dimethyl- --

• In Claim 1, column 106, line 48, please replace "$R_{12}$is" with --$R_{12}$ is--

• In Claim 16, column 108, line 3, please replace "dimethyihydantoin" with --dimethylhydantoin--

• In Claim 25, column 109, please replace the following structure

UNITED STATES PATENT AND TRADEMARK OFFICE
CERTIFICATE OF CORRECTION

PATENT NO. : 7,335,632 B2
APPLICATION NO. : 10/944117
DATED : February 26, 2008
INVENTOR(S) : Arun K. Ghosh et al.

It is certified that error appears in the above-identified patent and that said Letters Patent is hereby corrected as shown below:

" 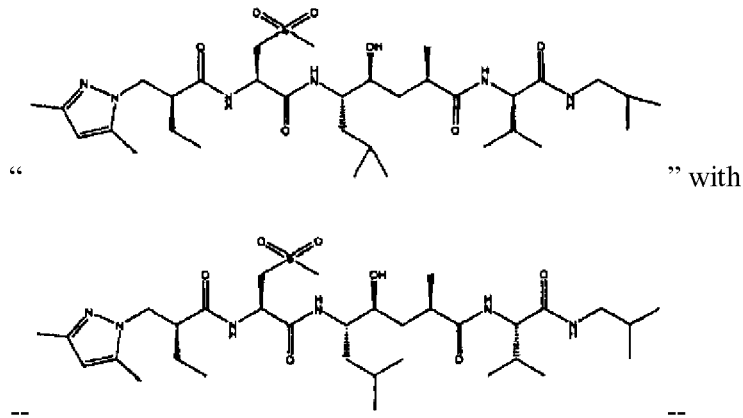 " with

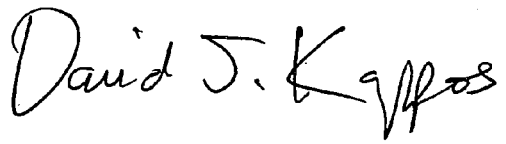

-- --

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,335,632 B2 |
| APPLICATION NO. | : 10/944117 |
| DATED | : February 26, 2008 |
| INVENTOR(S) | : Arun K. Ghosh et al. |

It is certified that error appears in the above-identified patent and that said Letters Patent is hereby corrected as shown below:

On page 1, section (73) please replace:

"CoMentis, Inc., South San Francisco, CA (US)" with

-- CoMentis, Inc., South San Francisco, CA (US);
The Board of Trustees of the University of Illinois, Urbana, IL (US); and
Oklahoma Medical Research Foundation, Oklahoma, OK (US) --

Signed and Sealed this

First Day of December, 2009

David J. Kappos
*Director of the United States Patent and Trademark Office*